US012582704B2

(12) United States Patent
Kwon

(10) Patent No.: US 12,582,704 B2
(45) Date of Patent: *Mar. 24, 2026

(54) FOOD COMPOSITION FOR IMPROVING BEHAVIORAL AND MOTOR FUNCTION CONTAINING ALDEHYDE DEHYDROGENASE FOR REDUCING ALDEHYDES PRODUCED BY OXIDATION OF ALCOHOL

(71) Applicant: PICOENTECH Co., LTD., Seongnam-Si (KR)

(72) Inventor: Hung Taeck Kwon, Seoul (KR)

(73) Assignee: PICOENTECH Co., LTD., Seongnam-Si (KR)

( * ) Notice: Subject to any disclaimer, the term of this patent is extended or adjusted under 35 U.S.C. 154(b) by 11 days.

This patent is subject to a terminal disclaimer.

(21) Appl. No.: 18/799,019

(22) Filed: Aug. 9, 2024

(65) Prior Publication Data

US 2024/0390466 A1 Nov. 28, 2024

Related U.S. Application Data

(63) Continuation of application No. 18/519,523, filed on Nov. 27, 2023.

(30) Foreign Application Priority Data

Dec. 1, 2022 (KR) ........................ 10-2022-0165810
Nov. 7, 2023 (KR) ........................ 10-2023-0153047

(51) Int. Cl.
*A61K 38/44* (2006.01)
*A61K 9/00* (2006.01)
(Continued)

(52) U.S. Cl.
CPC ............ *A61K 38/44* (2013.01); *A61K 9/0056* (2013.01); *A61K 36/064* (2013.01); *A61P 25/28* (2018.01);
(Continued)

(58) Field of Classification Search
CPC .................................................. A61K 2236/19
See application file for complete search history.

(56) References Cited

U.S. PATENT DOCUMENTS 9,988,650 B2 6/2018 Shaw, IV et al.

FOREIGN PATENT DOCUMENTS

KR 10-2016-0147709 A 12/2016
KR 10-2021-0105194 A 8/2021
(Continued)

OTHER PUBLICATIONS

International Search Report issued on Mar. 5, 2024, in corresponding International Application No. PCT/KR2023/019181, 9 pages.
(Continued)

*Primary Examiner* — Suzanne M Noakes
*Assistant Examiner* — Qing Xu
(74) *Attorney, Agent, or Firm* — Maier & Maier, PLLC

(57) ABSTRACT

Food or pharmaceutical compositions for improving behavior and motor function and to pharmaceutical composition for inhibiting or preventing Parkinson's disease, containing an aldehyde dehydrogenase encoded by a gene having more than 98% homology to the gene of SEQ ID NO: 1, encoded by the gene of SEQ ID NO: 1 including SEQ ID NO: 2, which is contained in lysate of any one or a mixture thereof selected from *Saccharomyces cerevisiae*, KCTC13925BP, KCTC14122BP, KCTC14123BP, KCTC14983BP, KCTC14984BP and KCTC14985BP.

5 Claims, 31 Drawing Sheets

Specification includes a Sequence Listing.

(51) Int. Cl.
    *A61K 36/064*     (2006.01)
    *A61K 36/64*     (2006.01)
    *A61P 25/28*     (2006.01)
    *C12N 9/02*     (2006.01)

(52) U.S. Cl.
    CPC .... *C12N 9/0008* (2013.01); *C12Y 102/01003*
                                            (2013.01)

(56)                     References Cited

FOREIGN PATENT DOCUMENTS

| | | | |
|---|---|---|---|
| KR | 10-2022-0117742 A | | 8/2022 |
| KR | 20220117742 A | * | 8/2022 |
| WO | WO 2021167309 A1 | * | 8/2021 |

OTHER PUBLICATIONS

Grünblatt, E. et al., "Aldehyde dehydrogenase (ALDH) in Alzheimer's and Parkinson's disease", Journal of Neural Transmission, 2016, vol. 123, pp. 83-90, 9 pages.

* cited by examiner

【Figure 1】
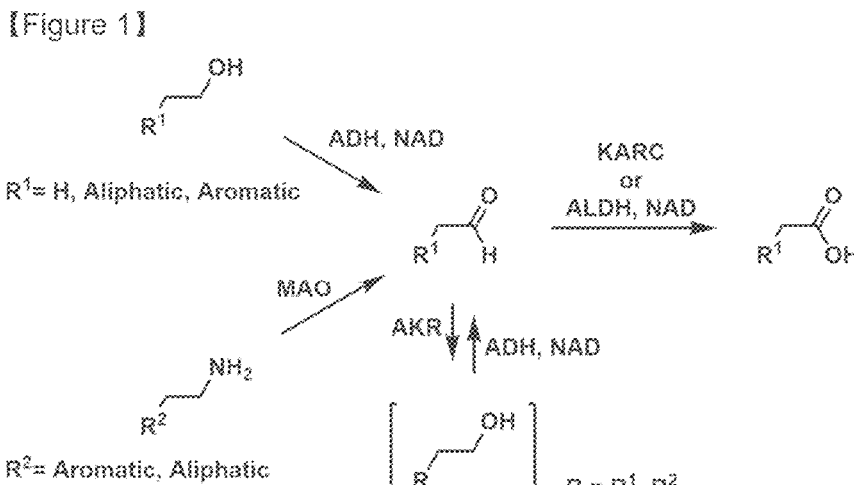
【Figure 2】
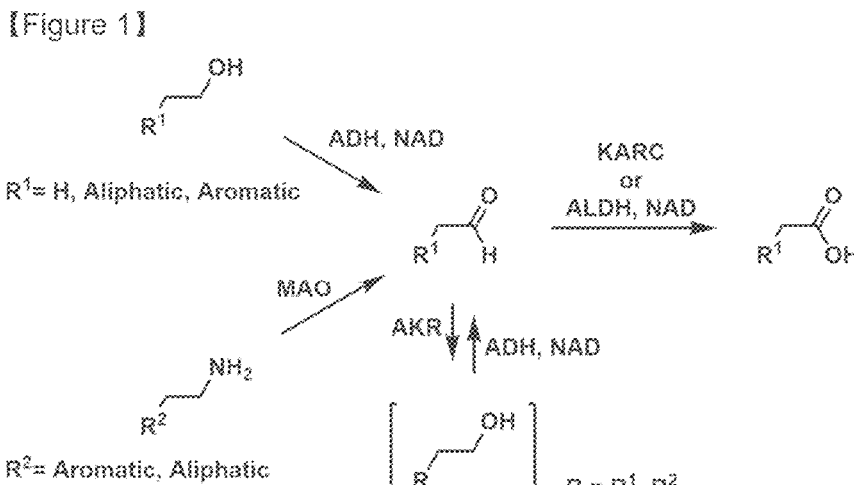

【Figure 3】
【Figure 4】
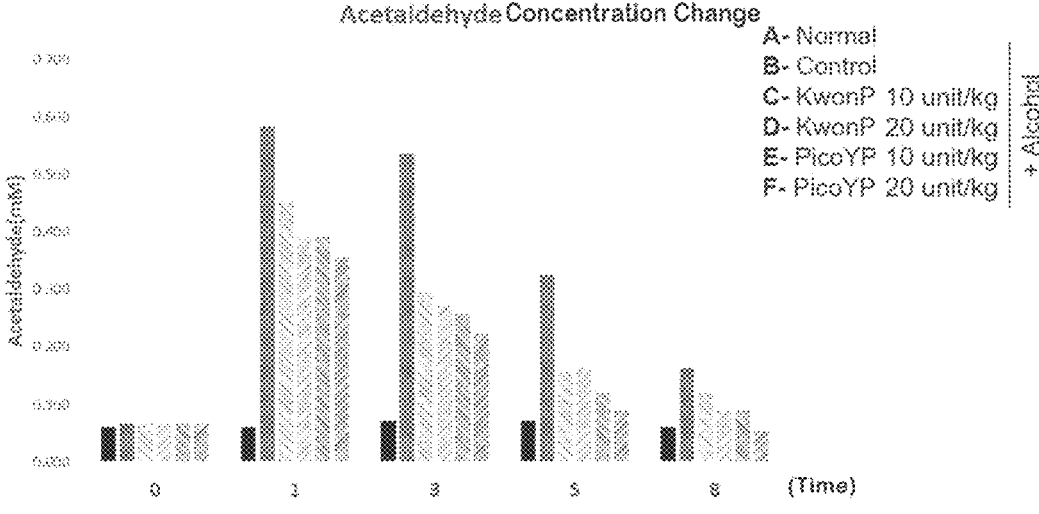

[Figure 5]
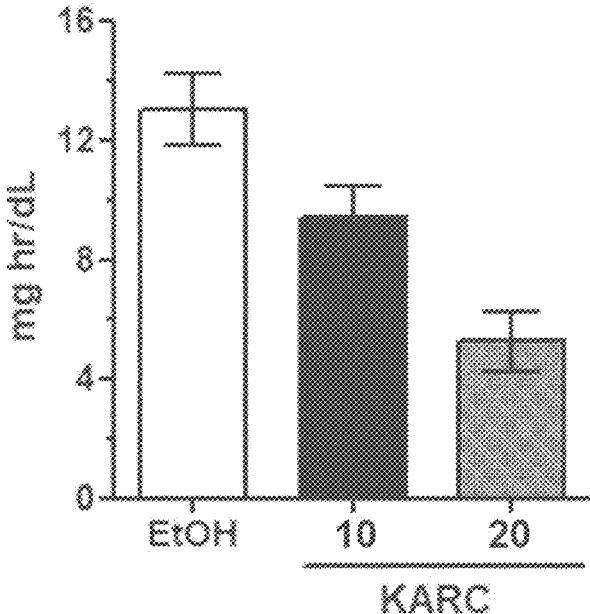
[Figure 6]
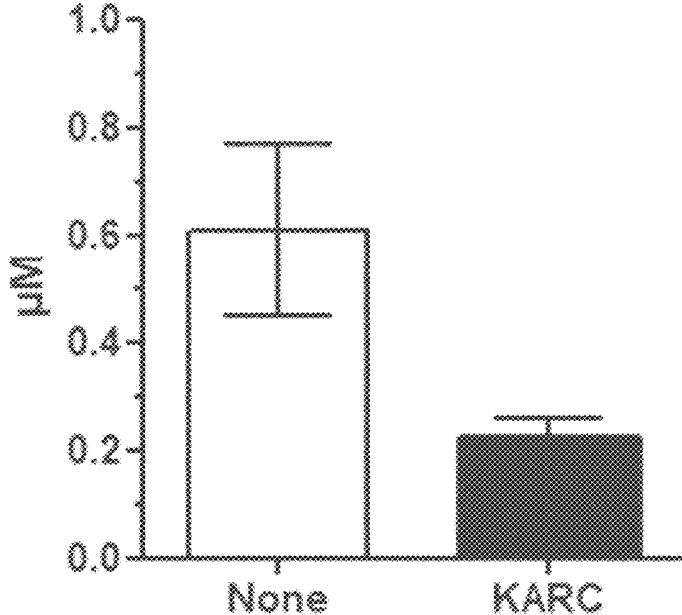

【Figure 7】
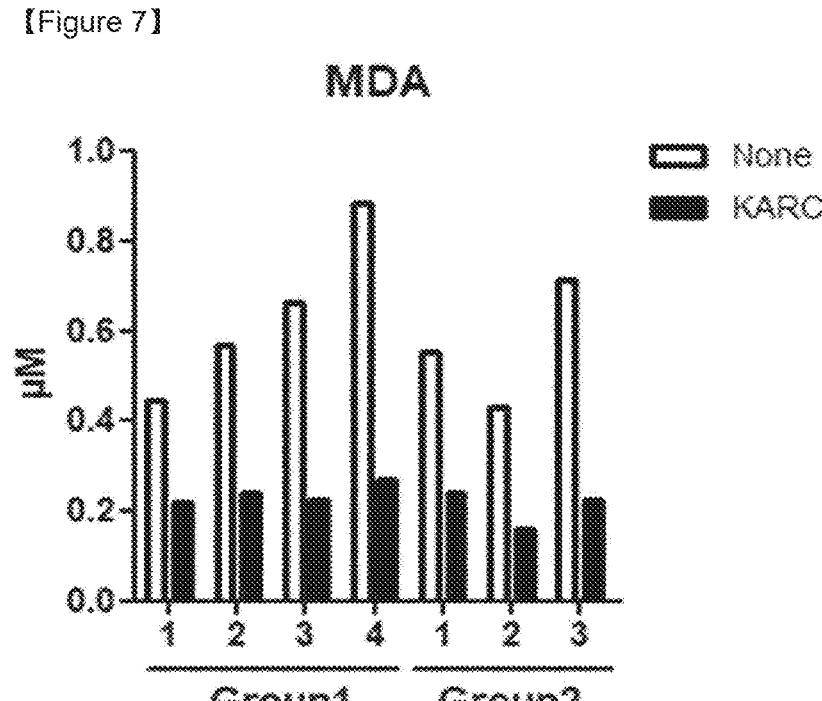
【Figure 8】
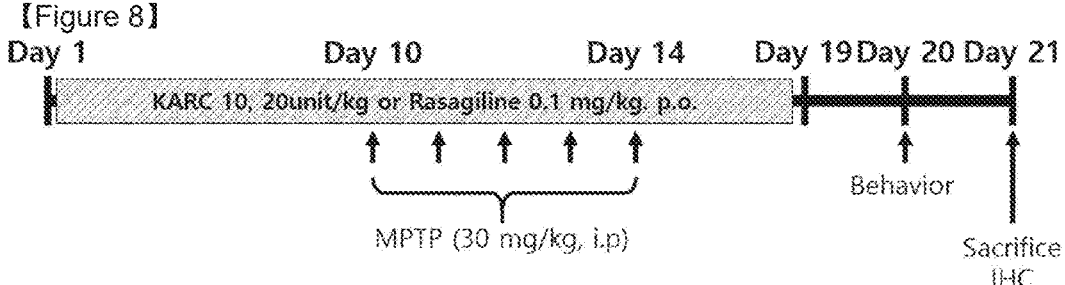

【Figure 9】
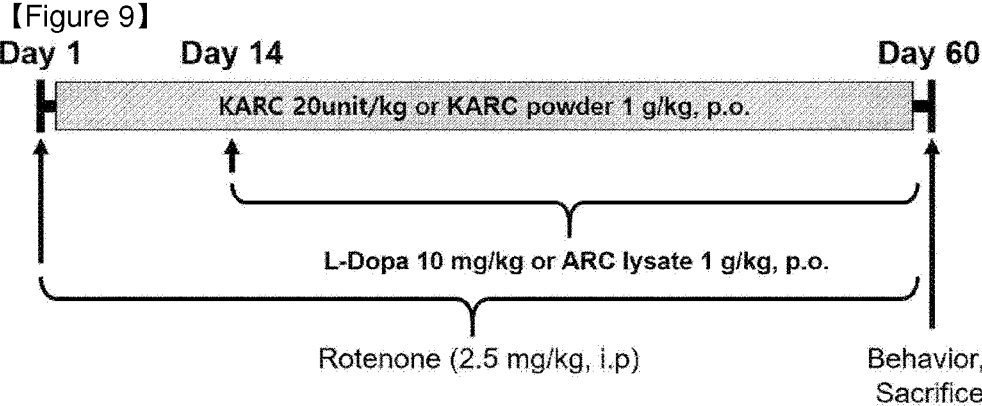
【Figure 10】
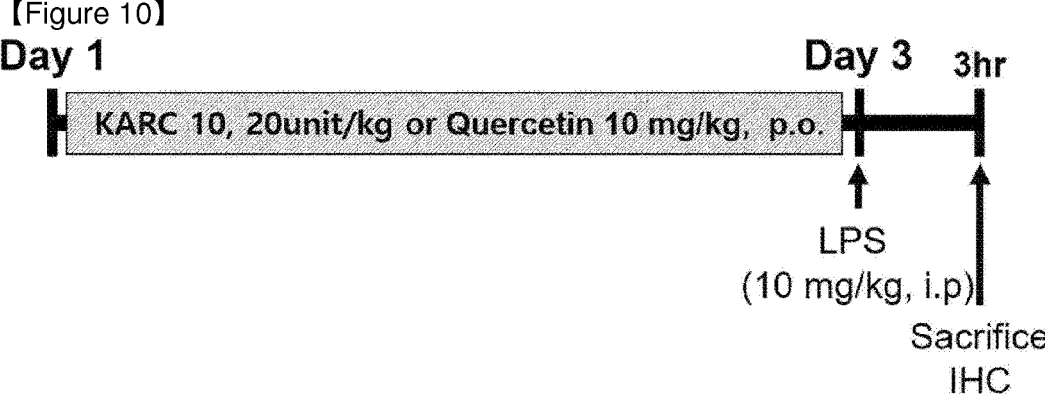
【Figure 11】
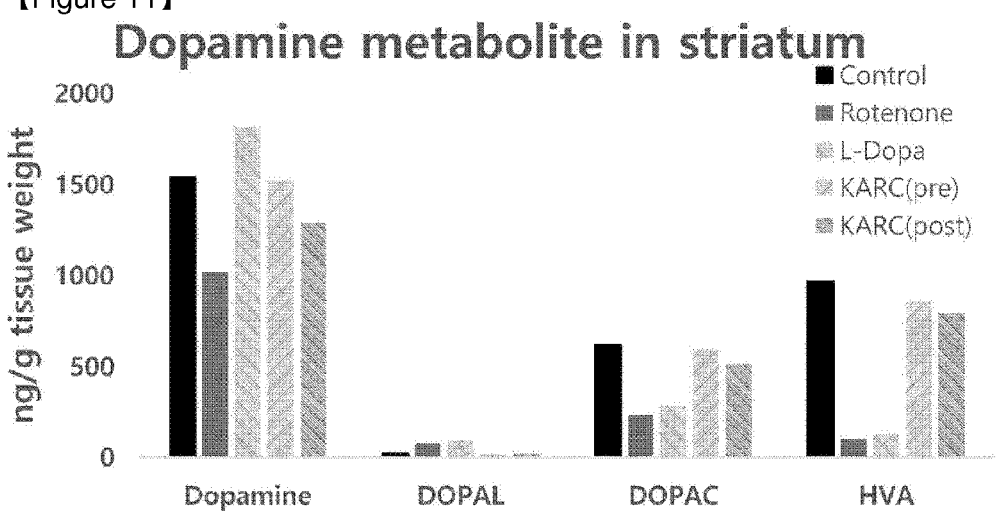

【Figure 12】
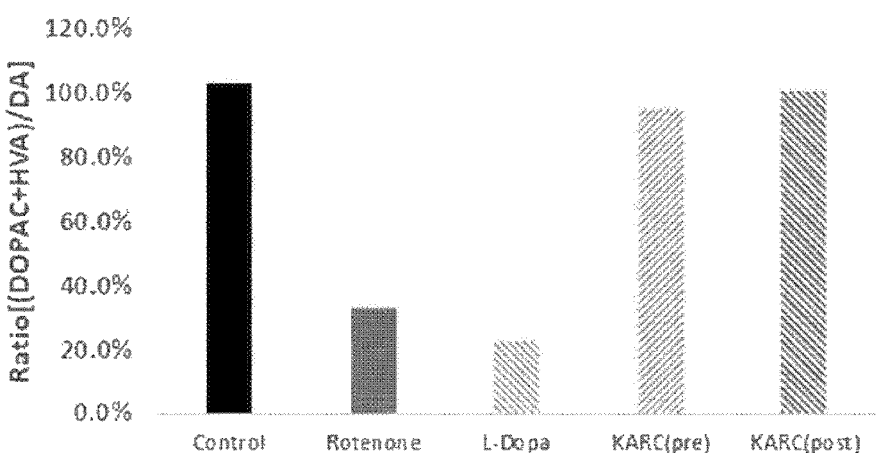
【Figure 13】
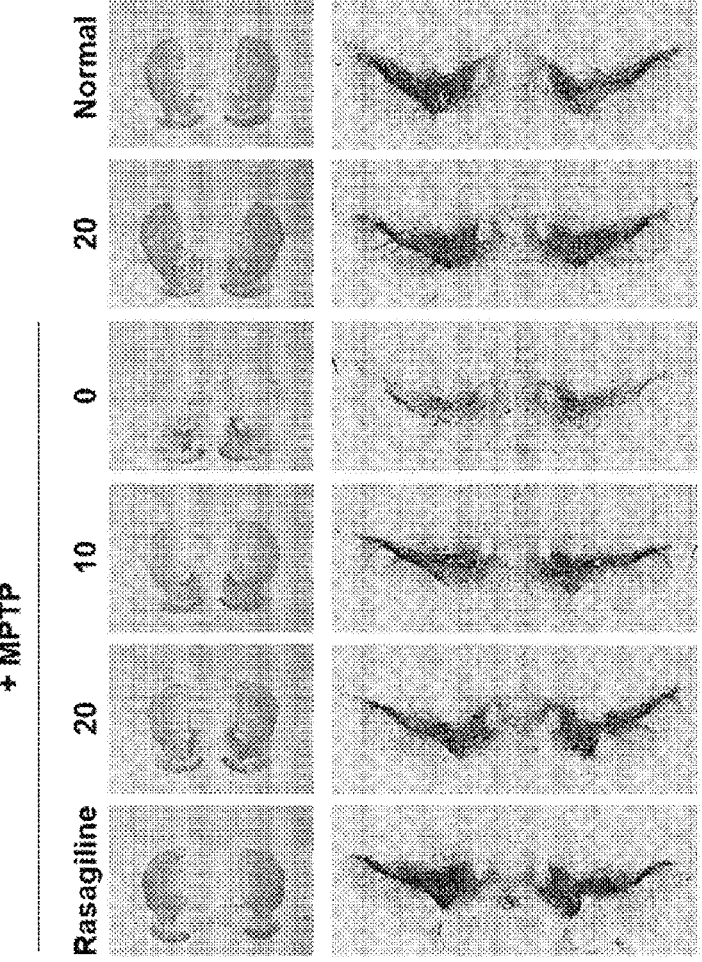

【Figure 14】
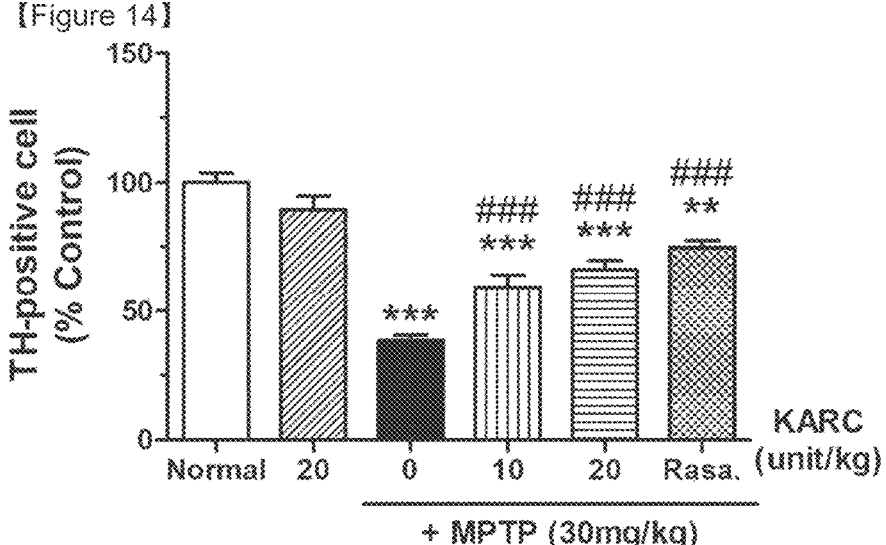
【Figure 15】
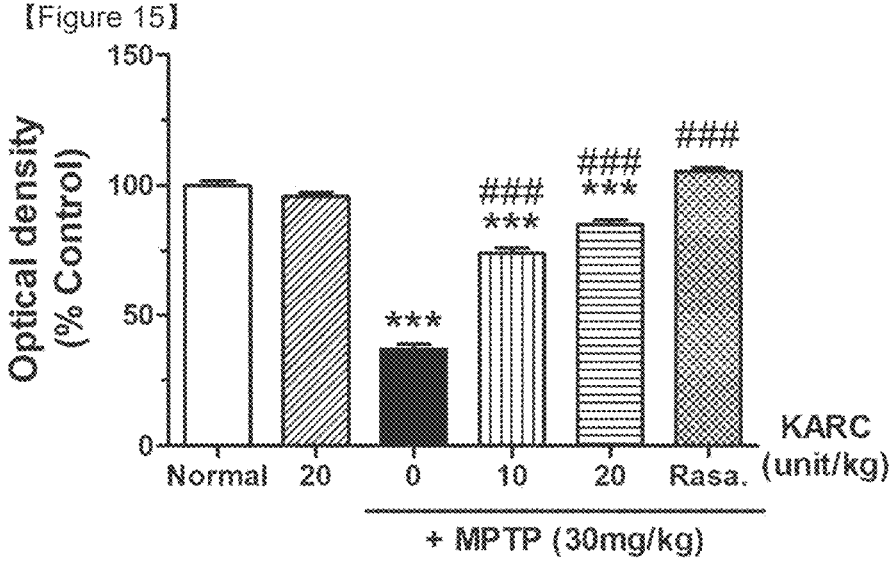

[Figure 16]

[Figure 17]
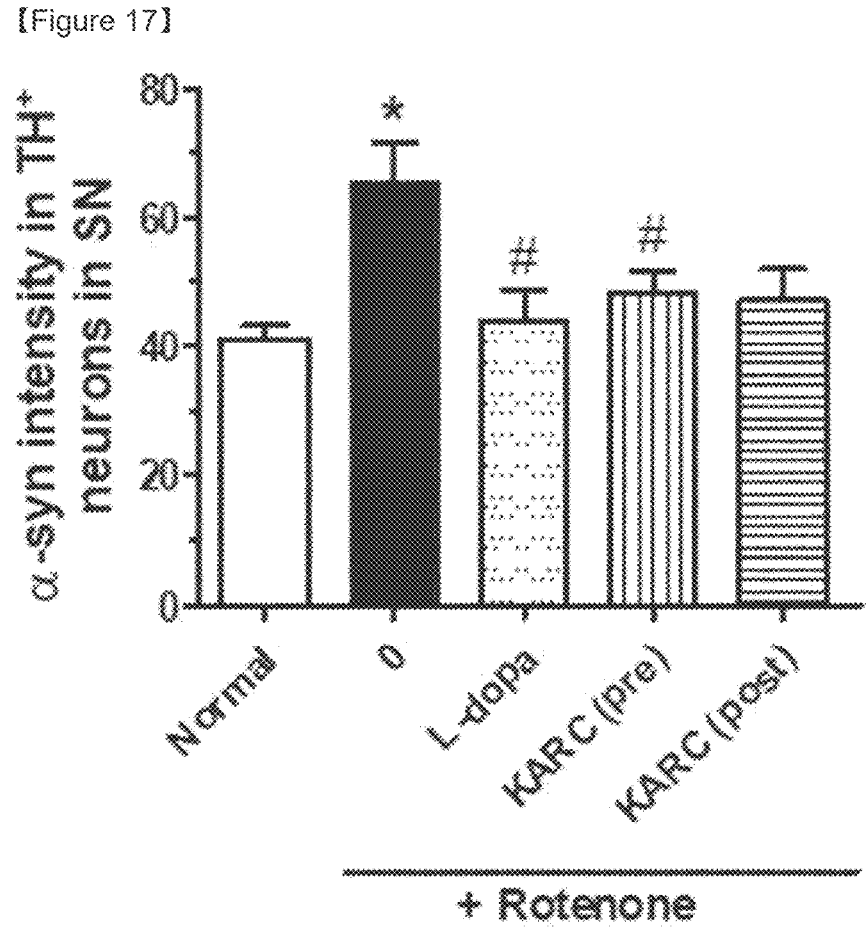
[Figure 18]
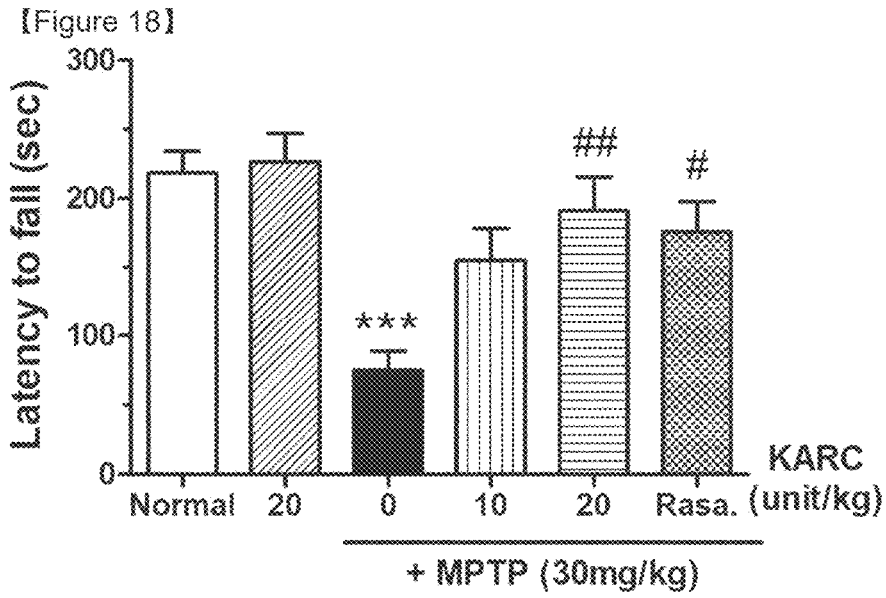

【Figure 19】
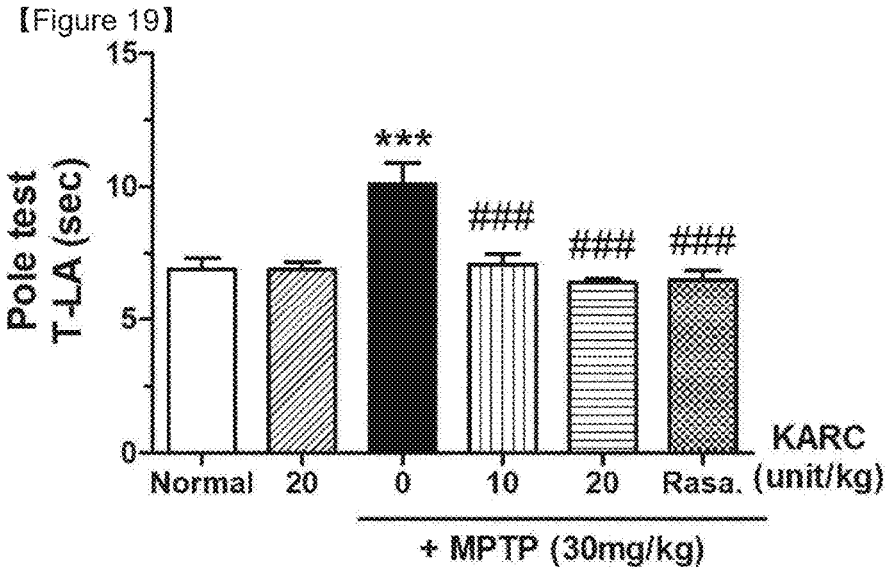
【Figure 20】
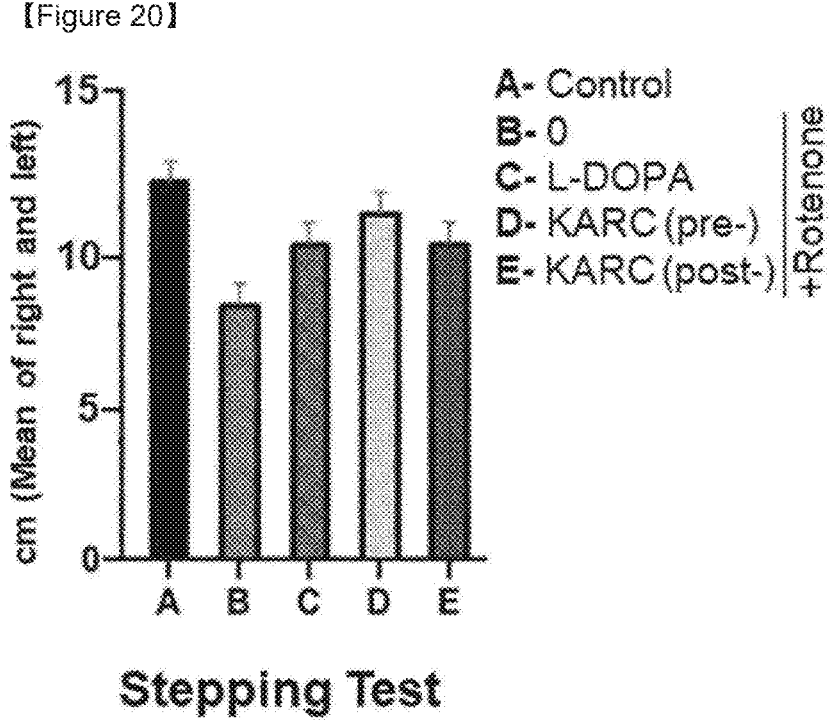
Stepping Test

【Figure 21】
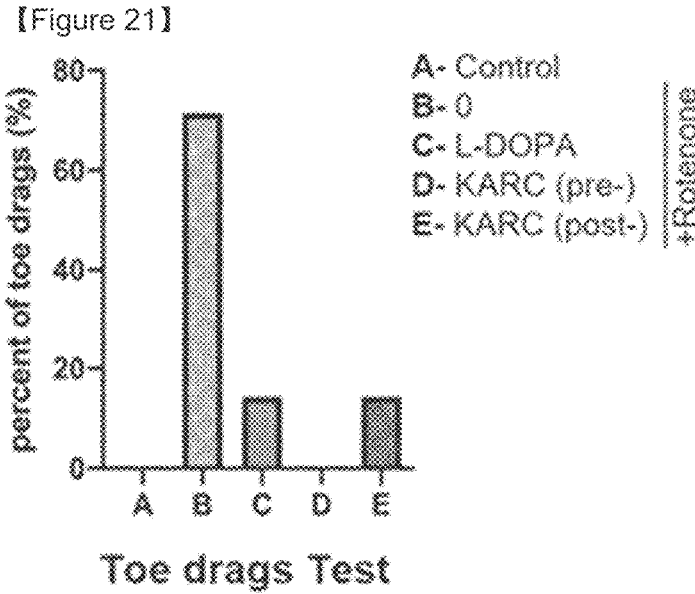
Toe drags Test
【Figure 22】
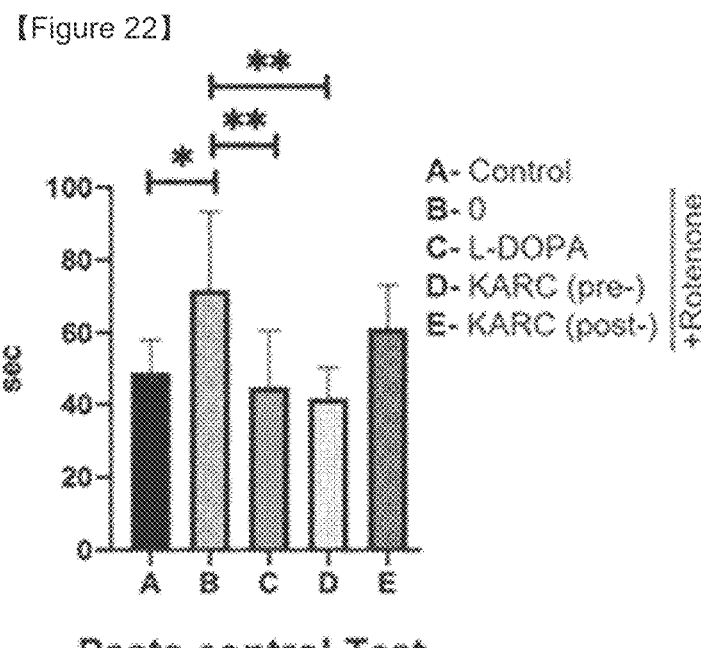
Pasta control Test

[Figure 23]
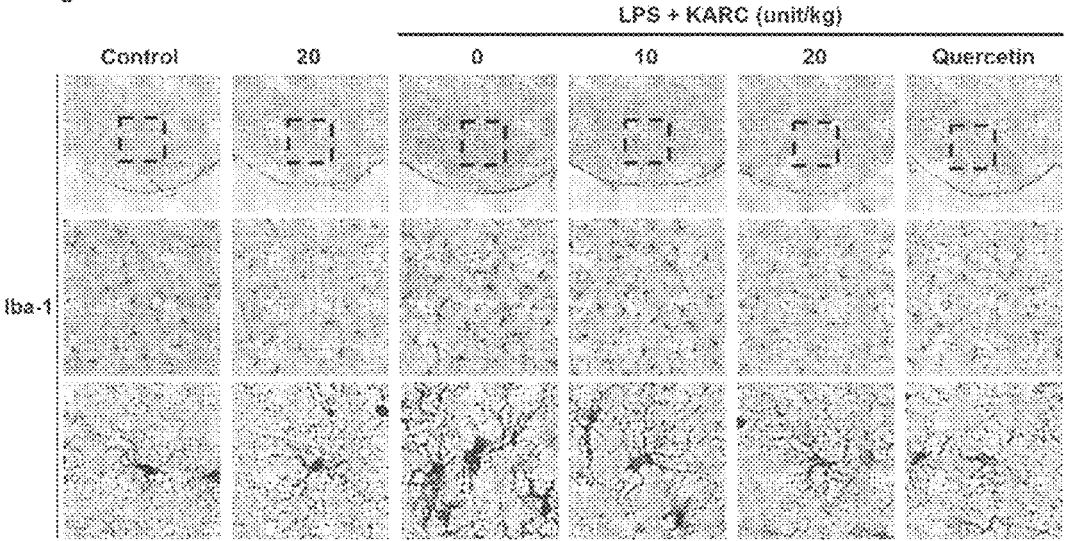
[Figure 24]
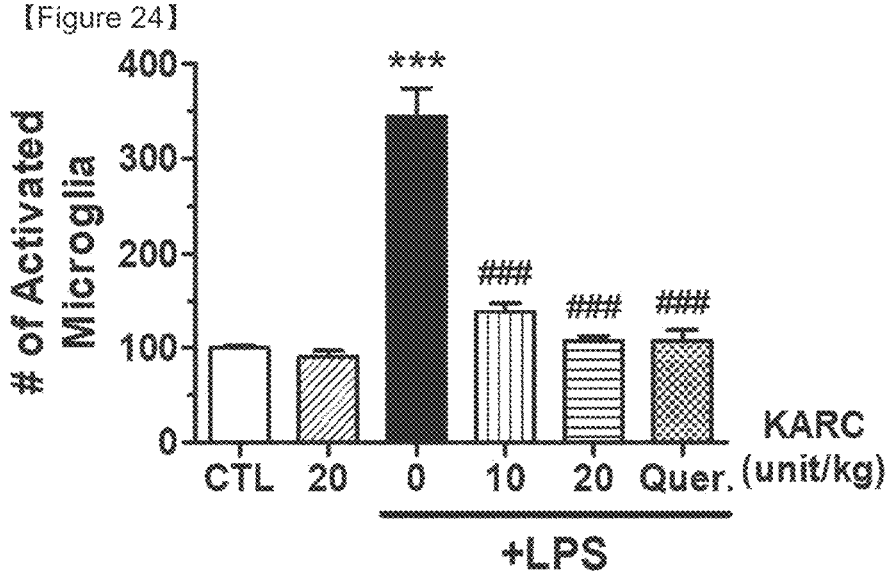

【Figure 25】
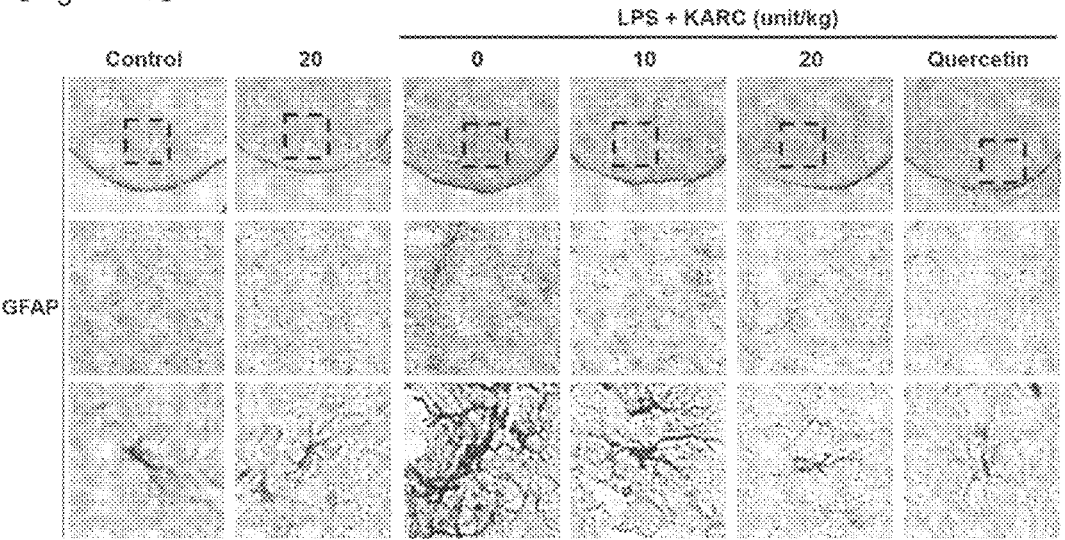
【Figure 26】
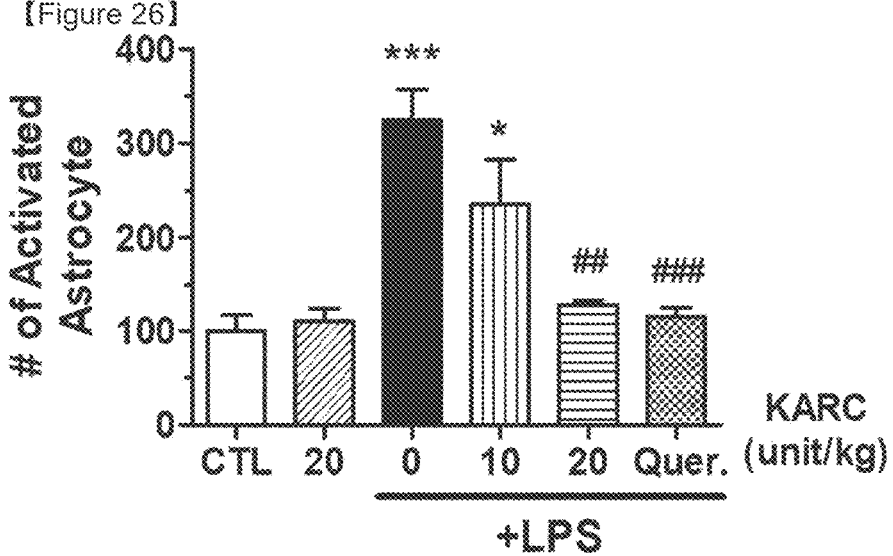

【Figure 27】
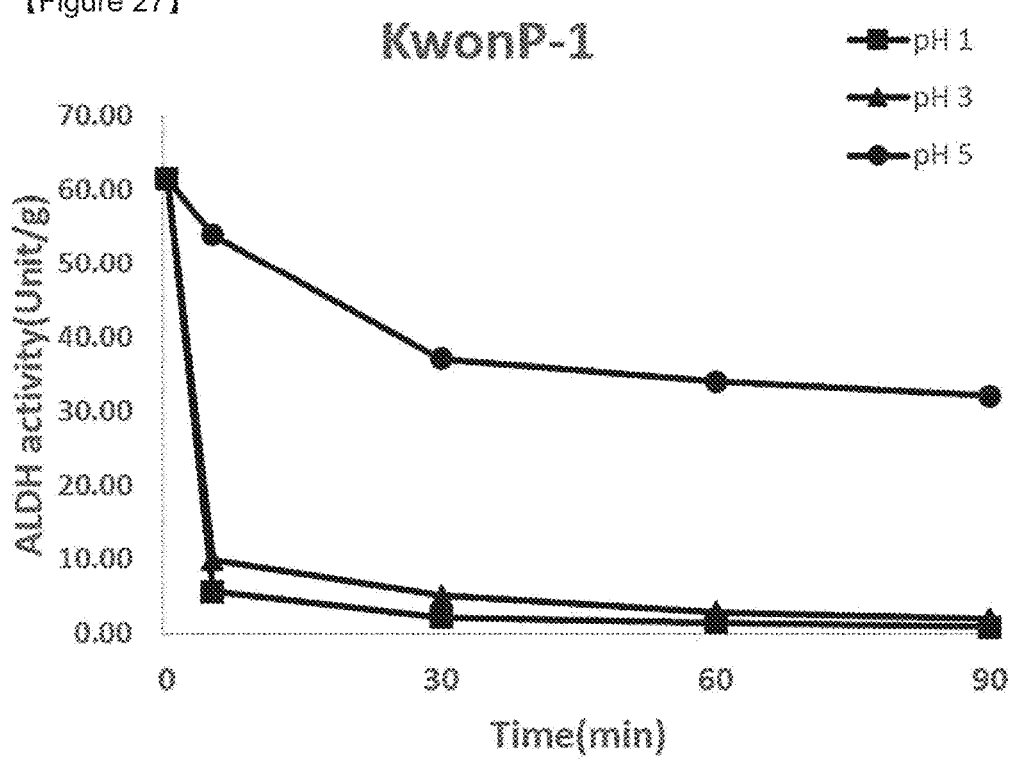

【Figure 28】
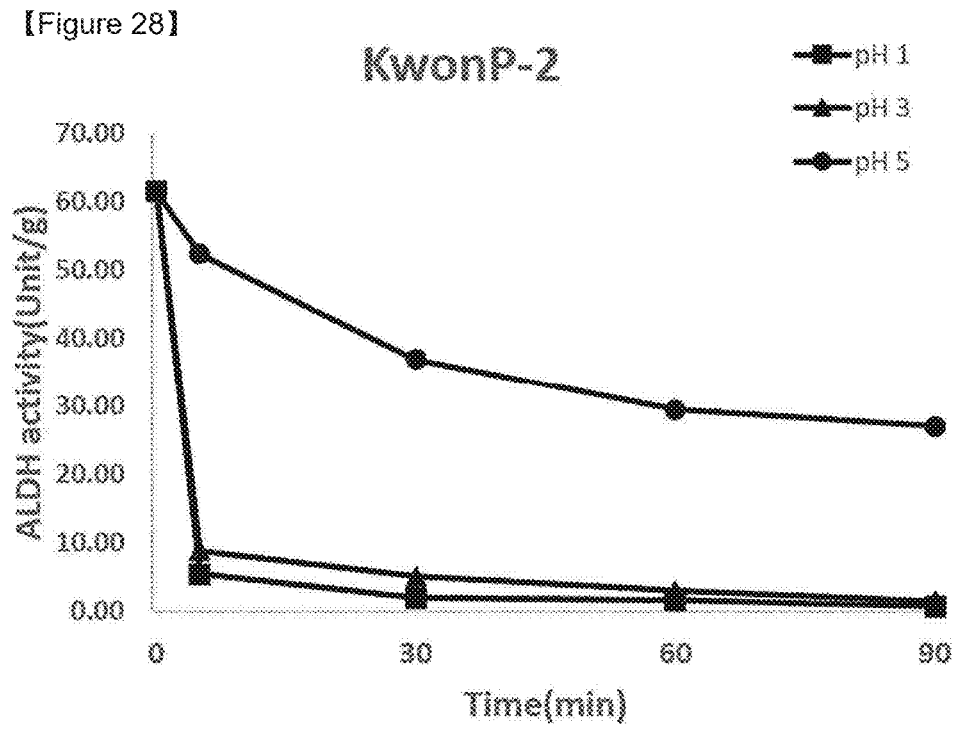
【Figure 29】
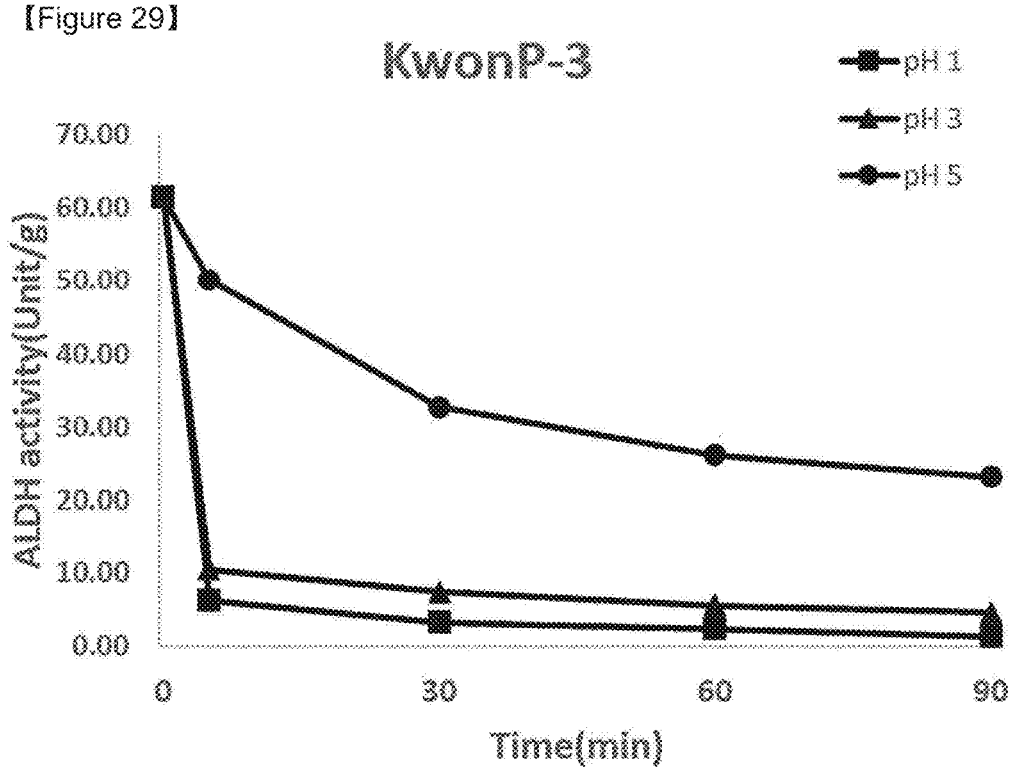

【Figure 30】
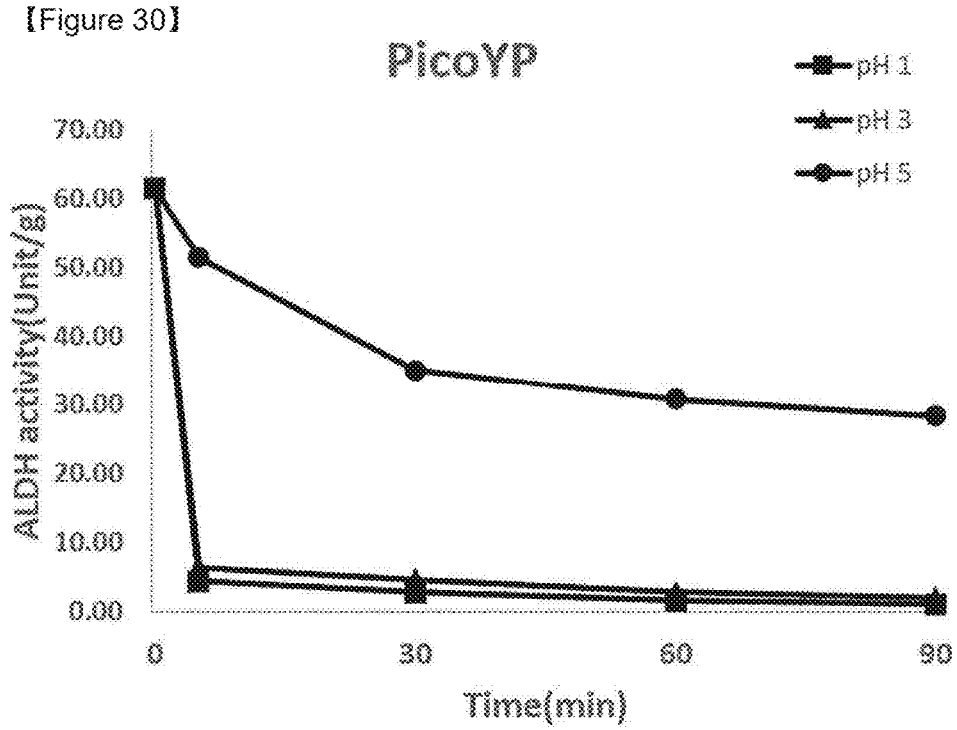
【Figure 31】
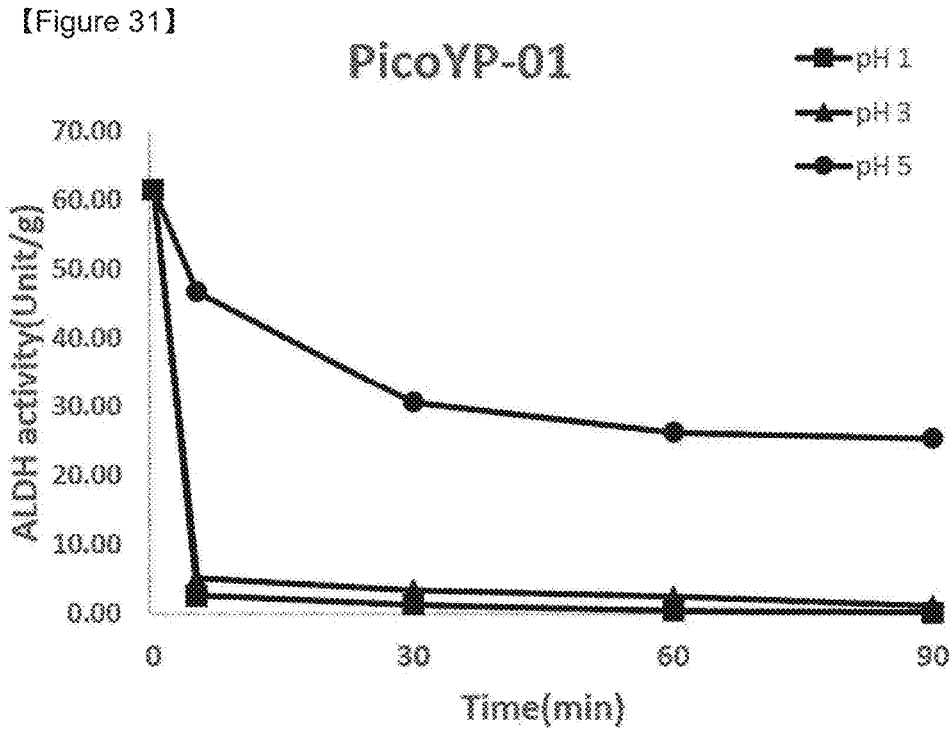

【Figure 32】
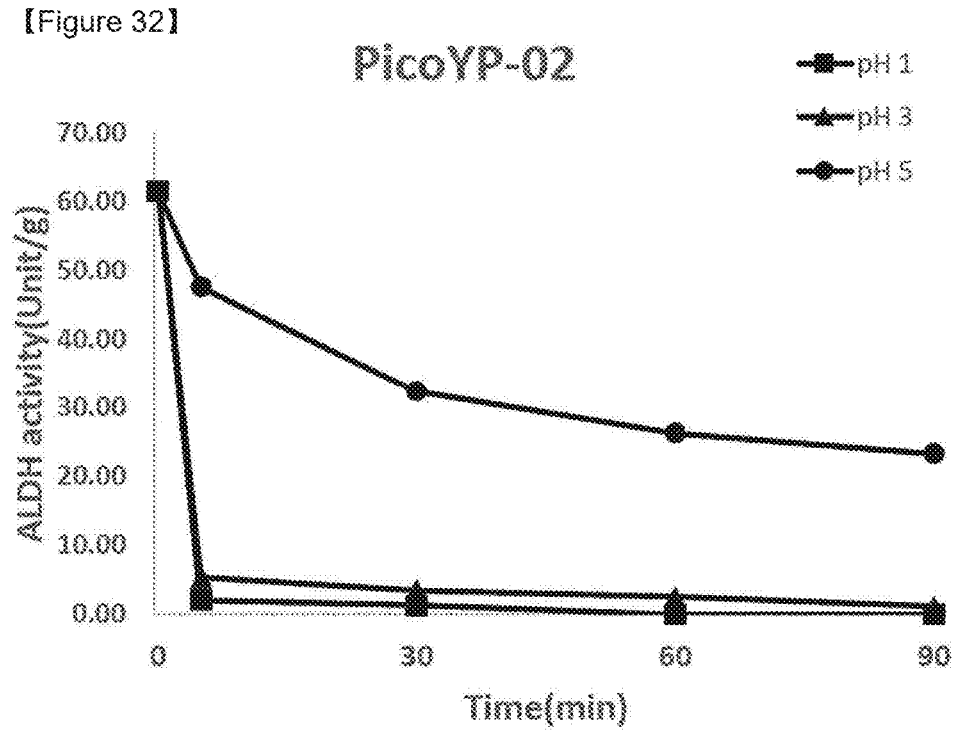
【Figure 33】
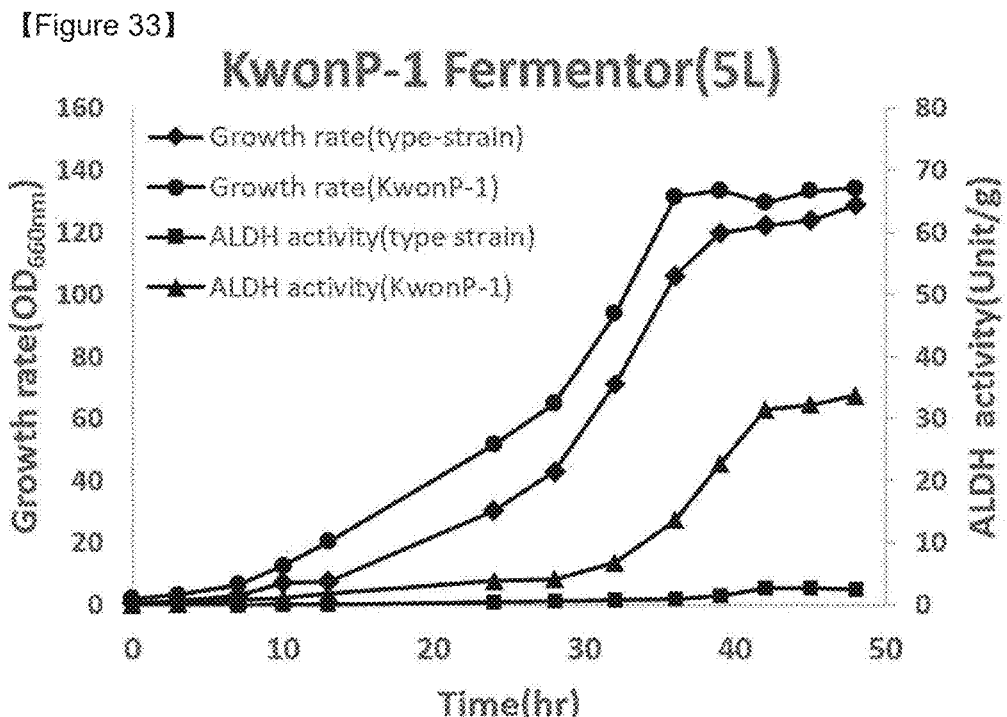

【Figure 34】
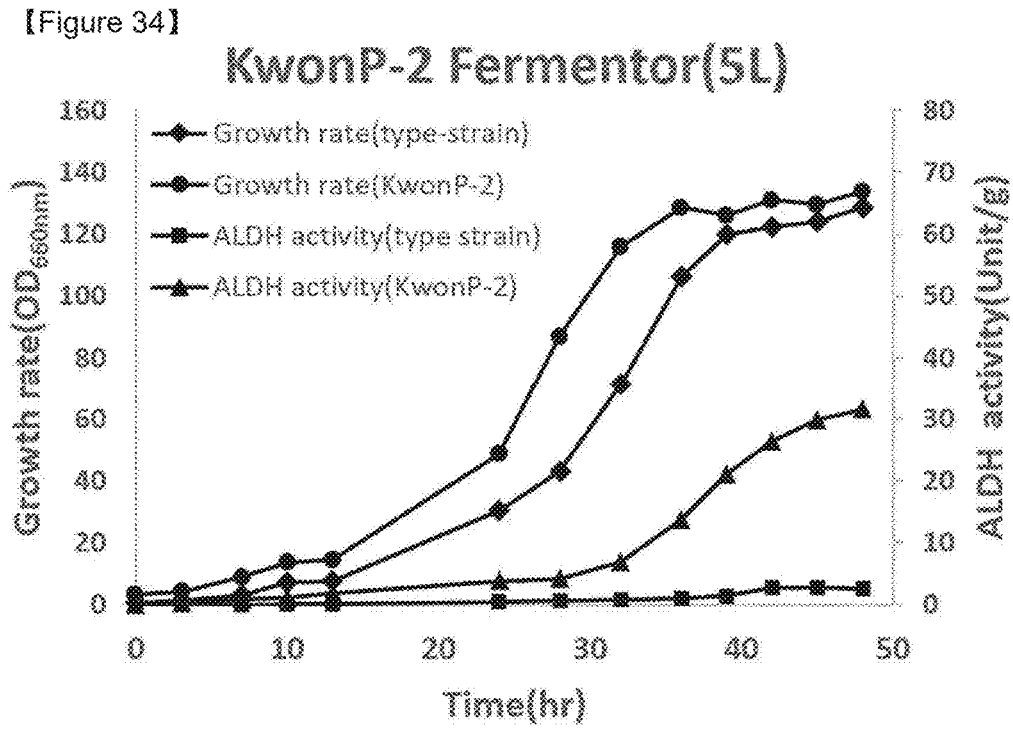
【Figure 35】
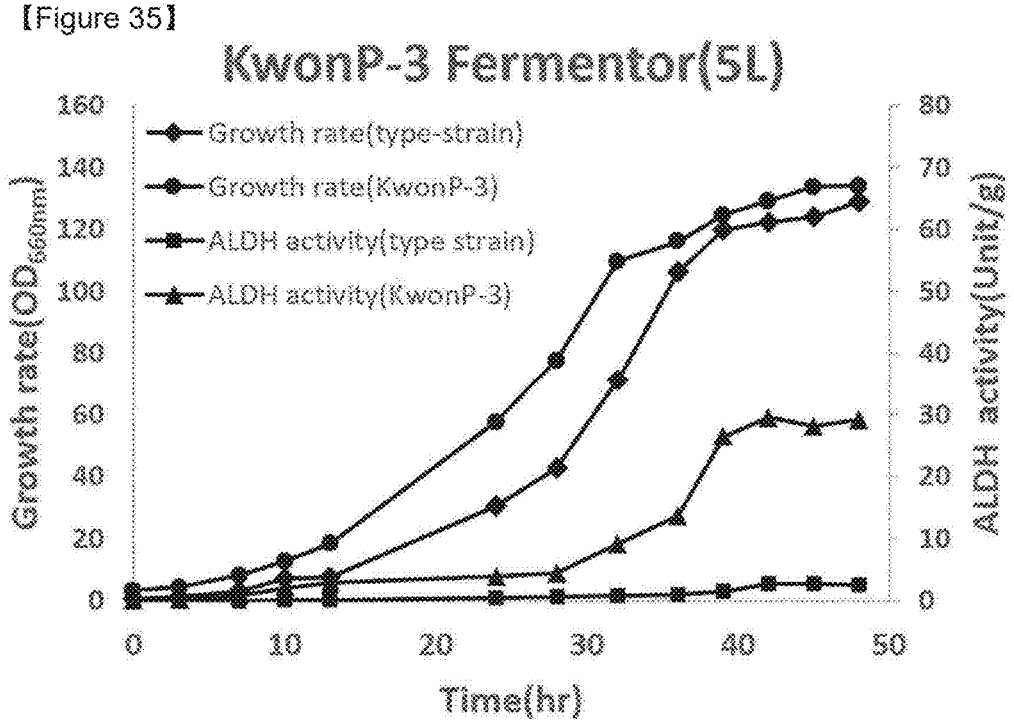

【Figure 36】
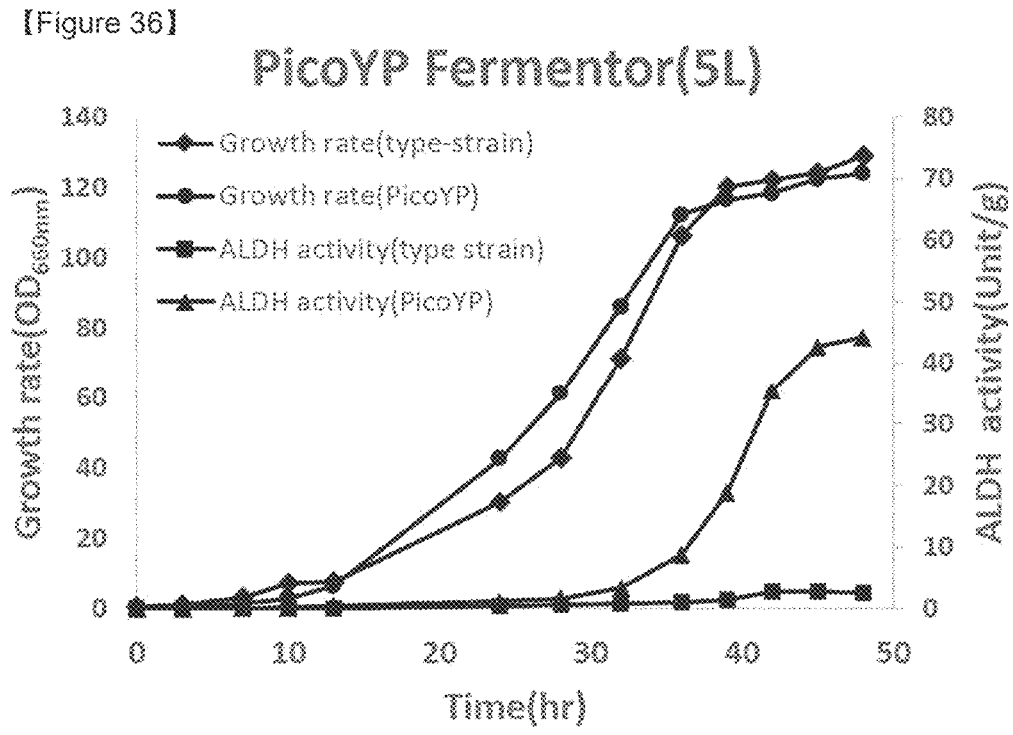
【Figure 37】
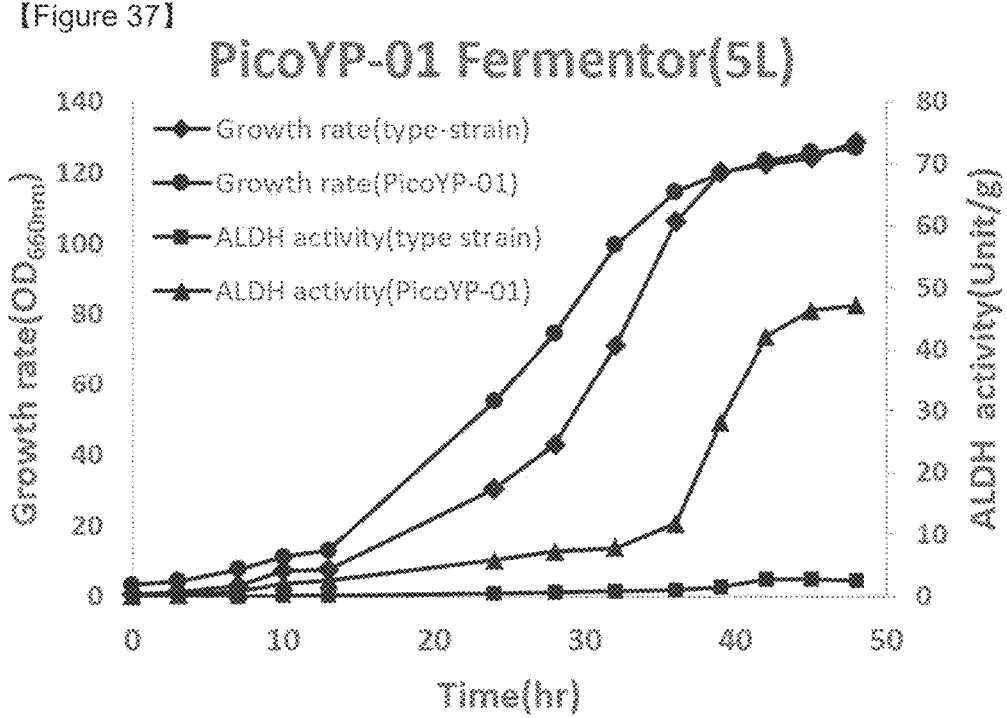

【Figure 38】
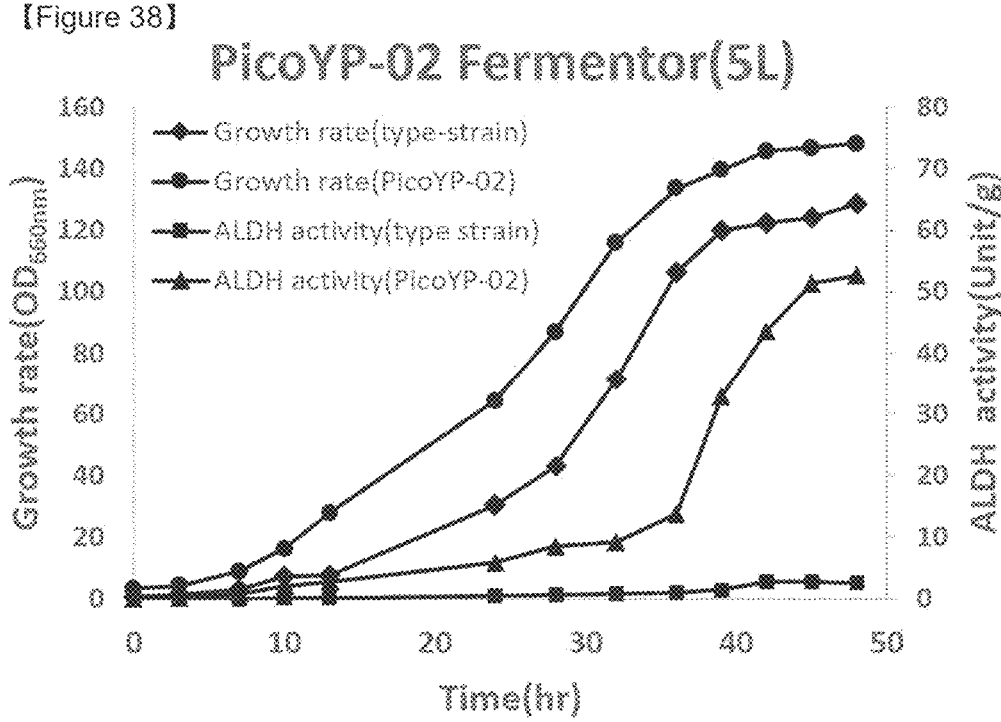
【Figure 39】
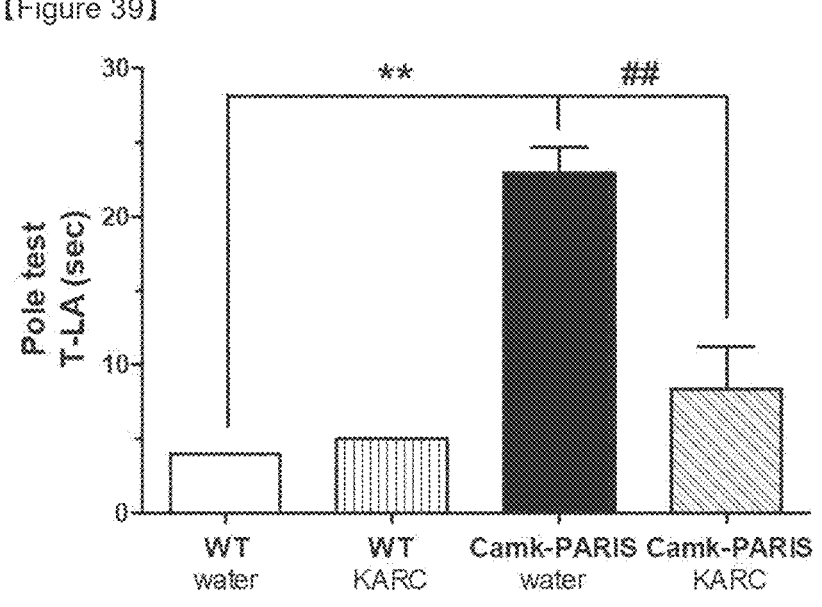

【Figure 40】
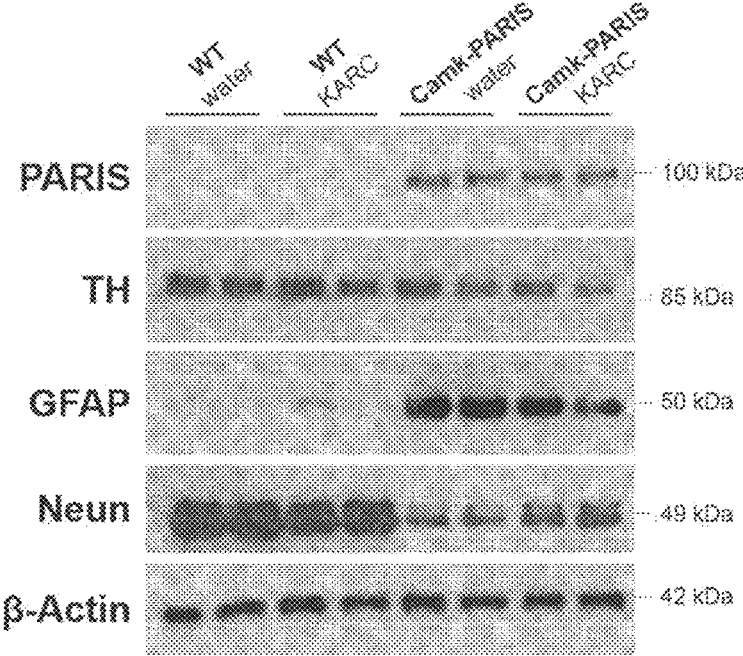
【Figure 41】
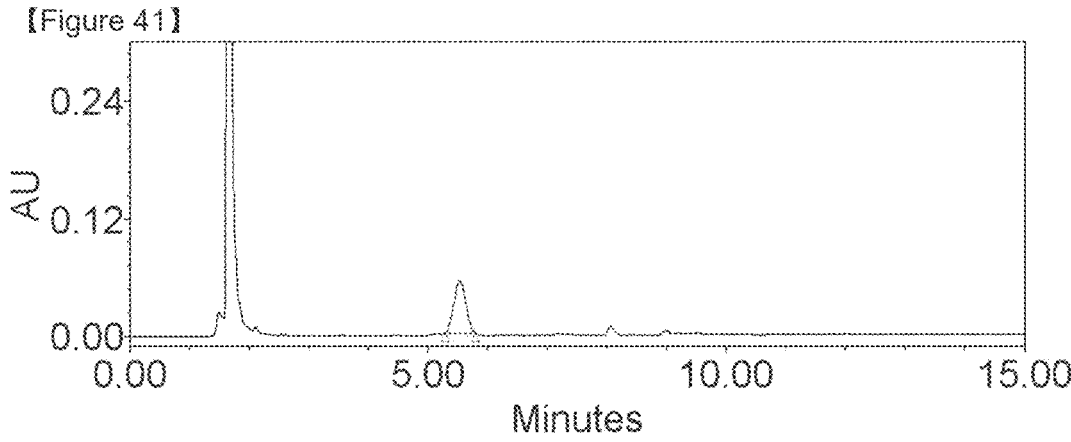

【Figure 42】
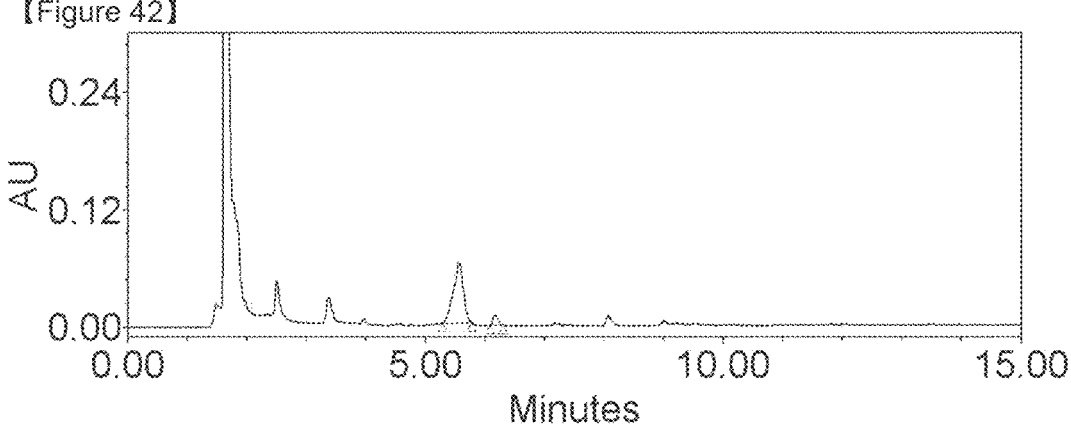
【Figure 43】
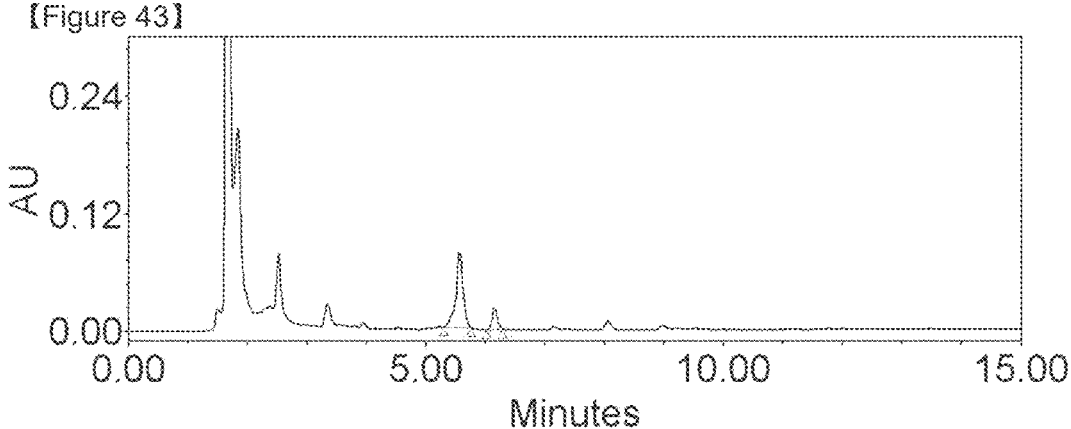

【Figure 44】
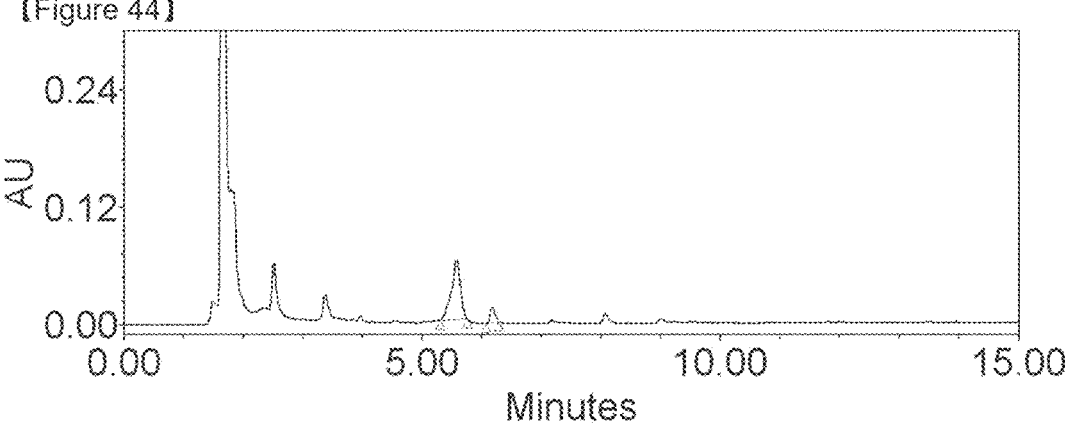
【Figure 45】
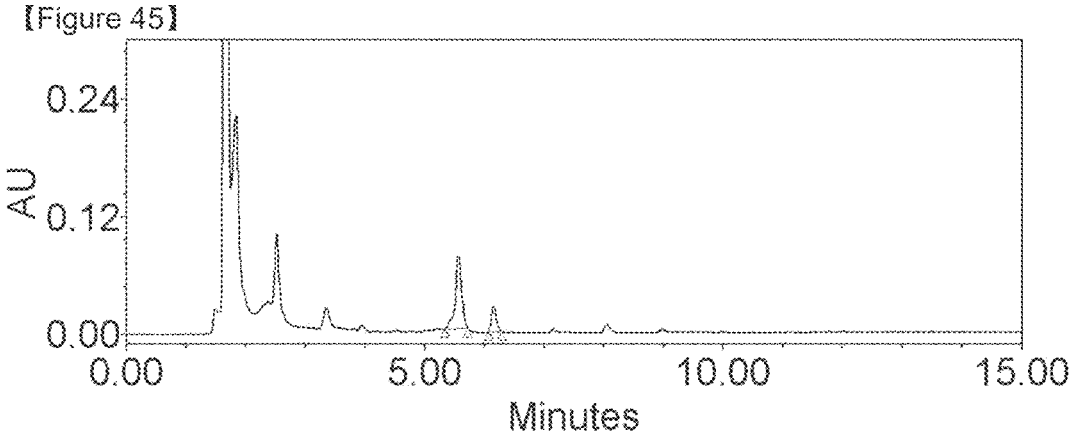

【Figure 46】
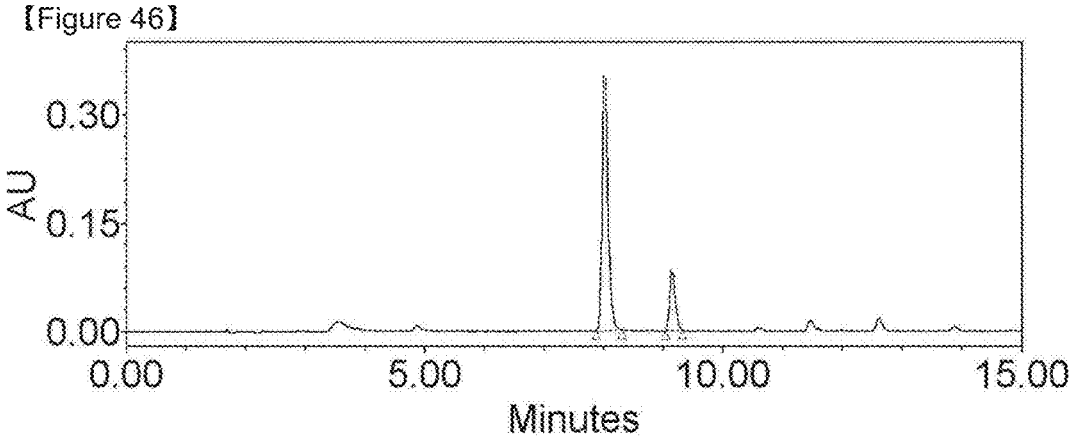
【Figure 47】
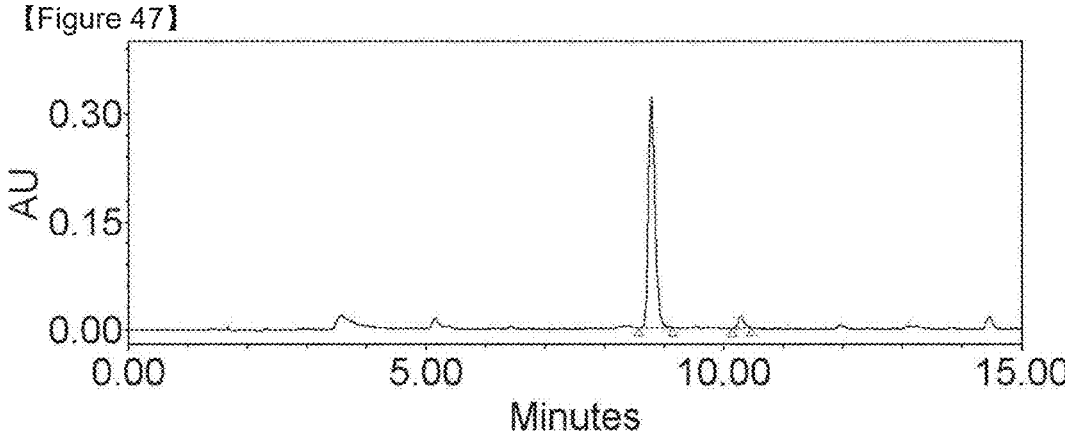
【Figure 48】
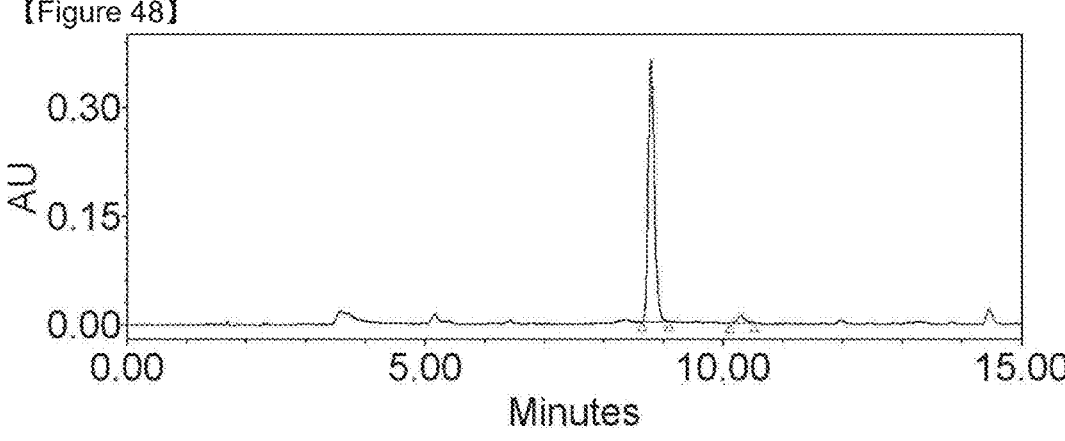

【Figure 49】
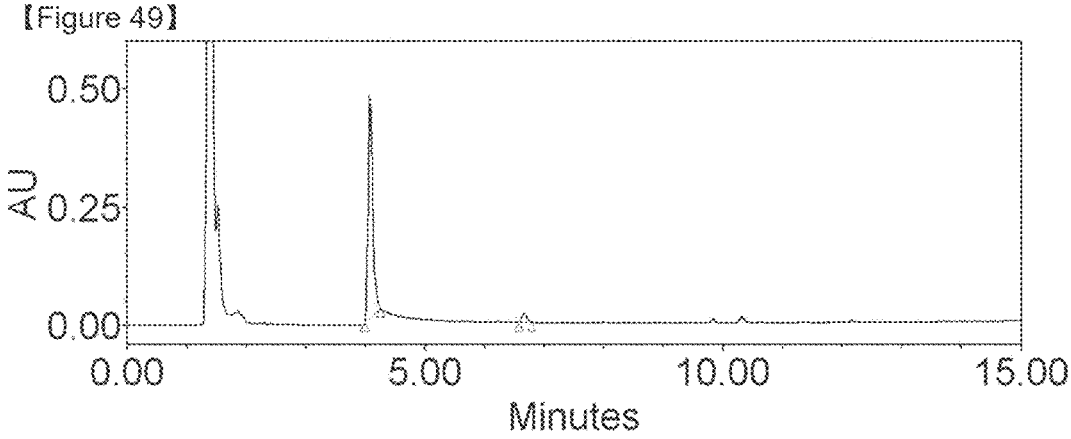
【Figure 50】
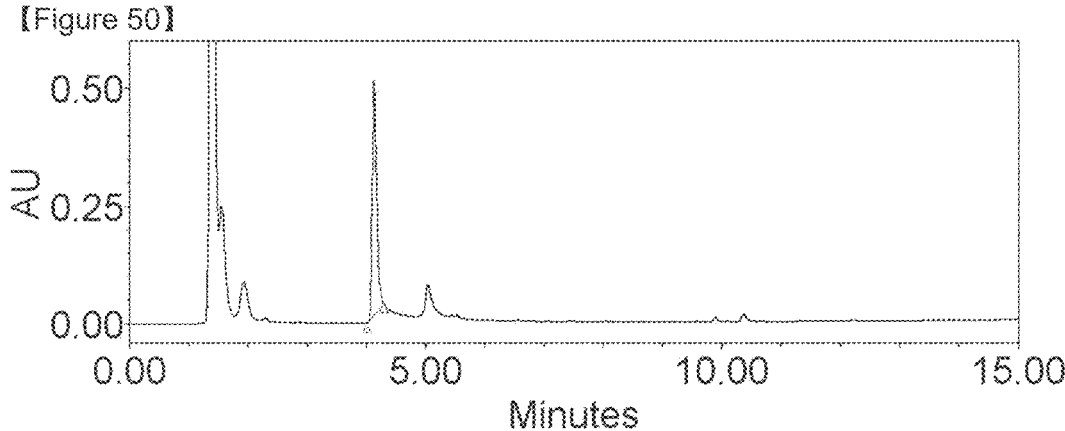
【Figure 51】
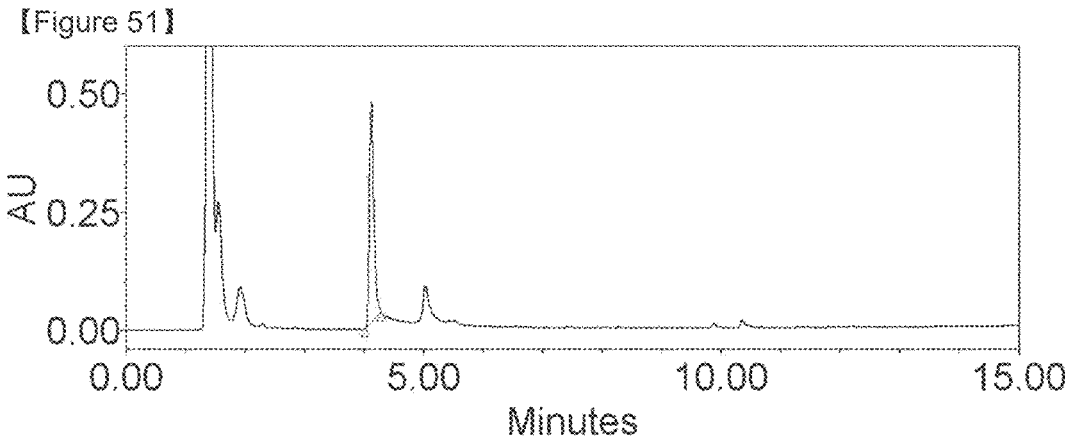

【Figure 52】
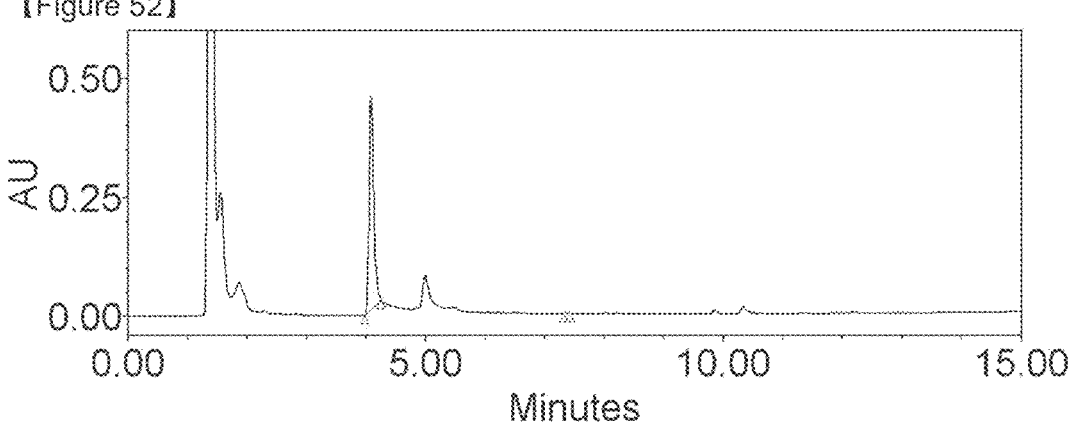
【Figure 53】
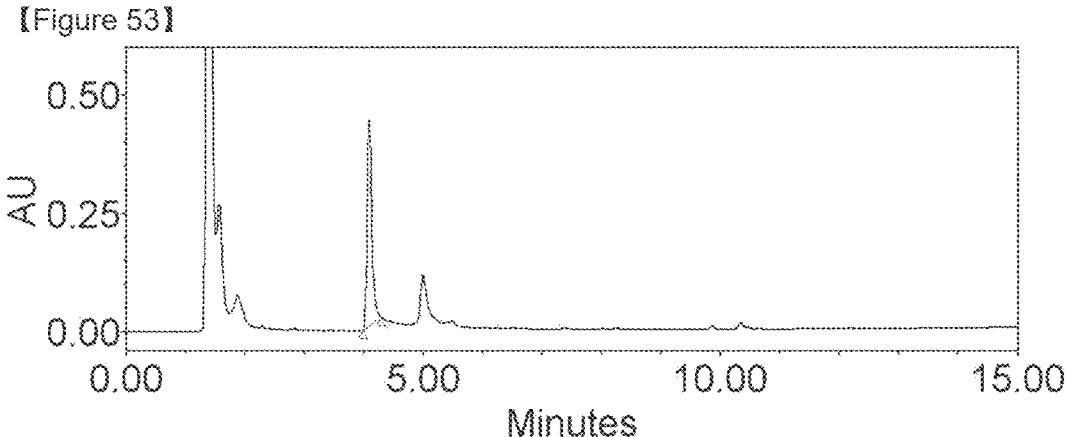

【Figure 54】
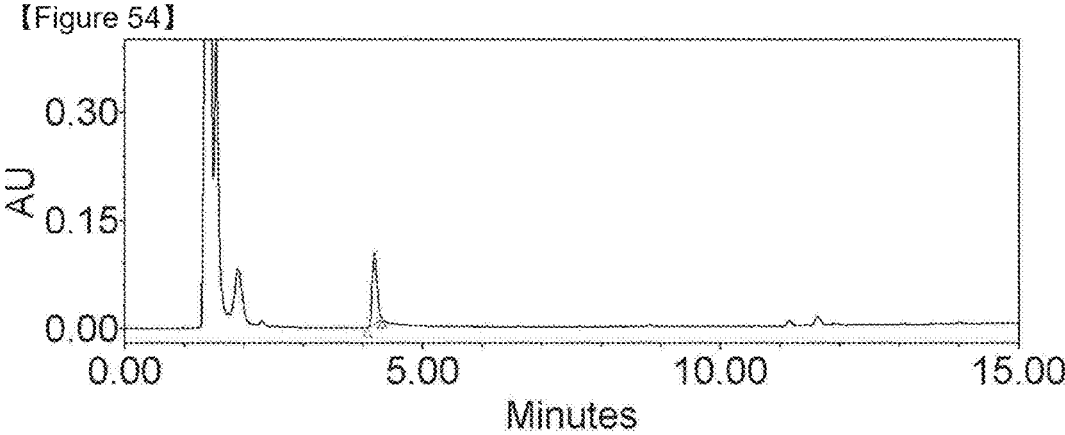
【Figure 55】
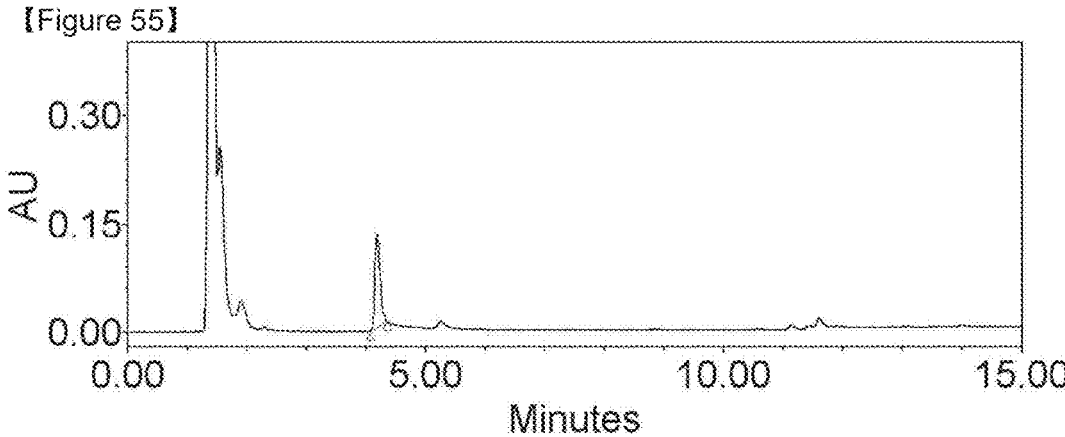
【Figure 56】
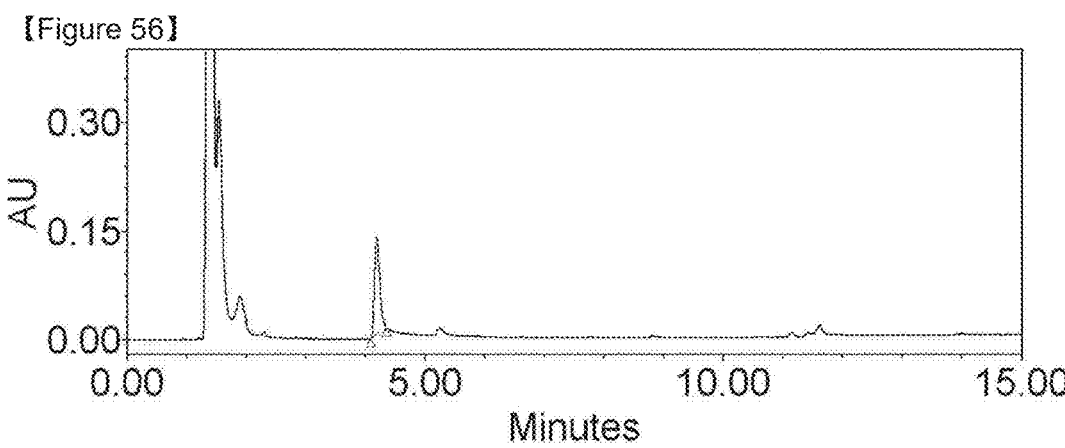

【Figure 57】
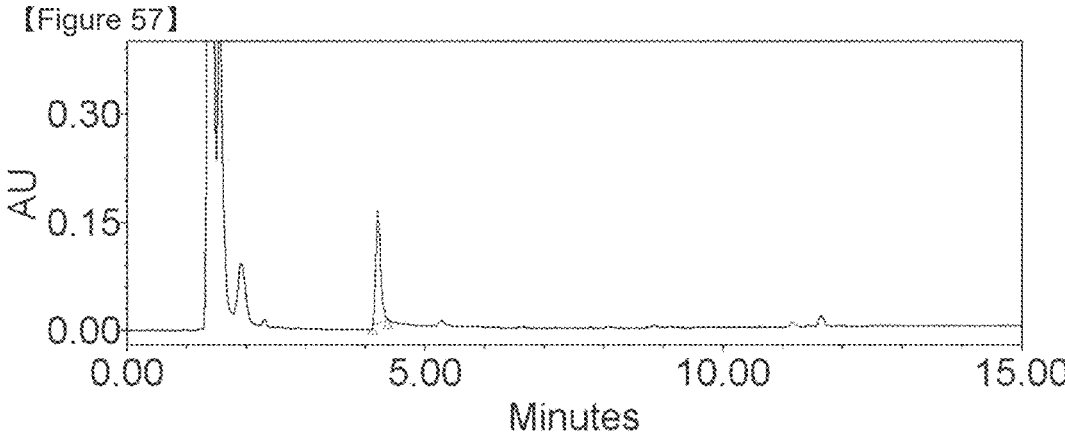
【Figure 58】
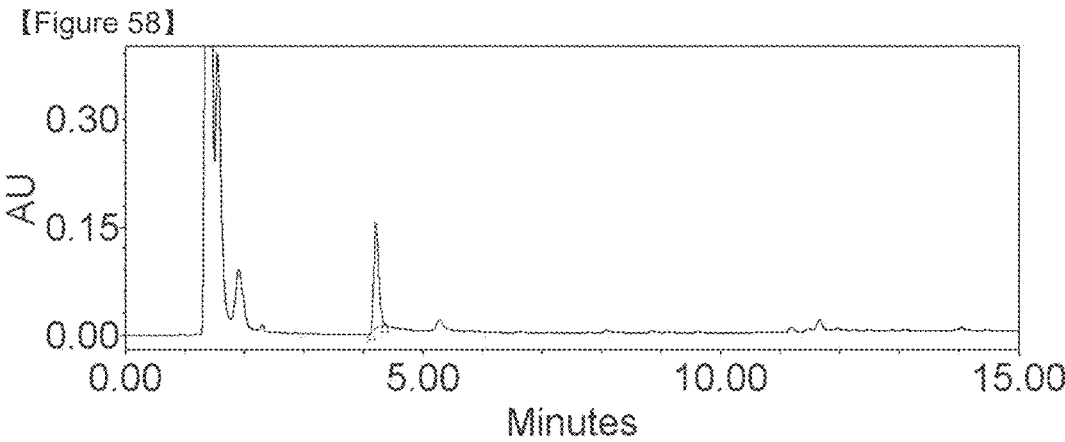
【Figure 59】
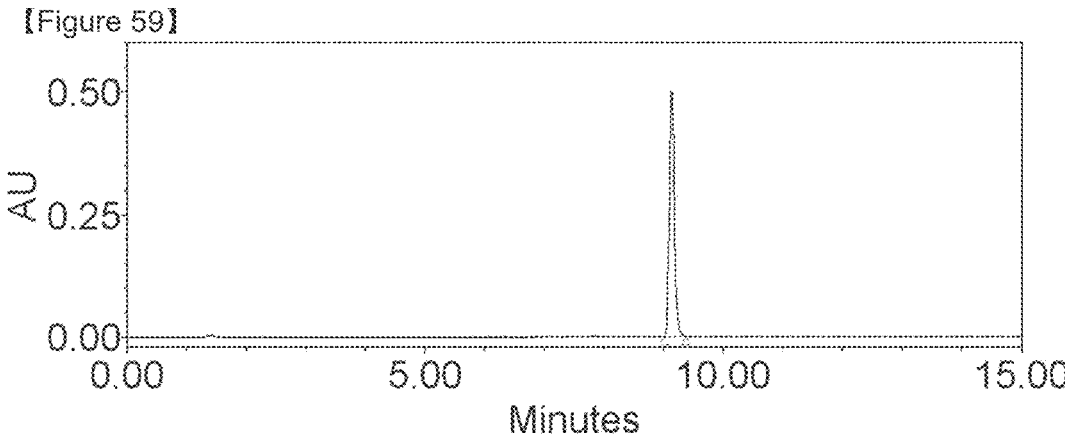

【Figure 60】
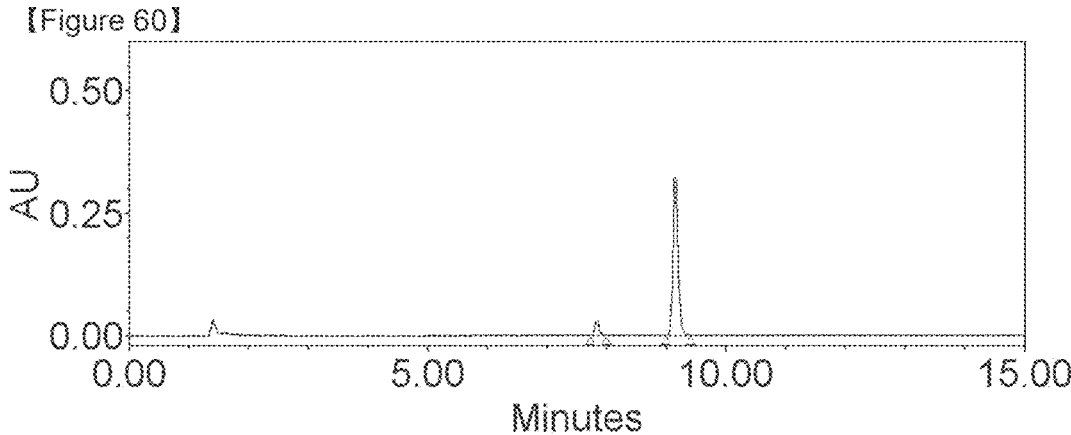
【Figure 61】
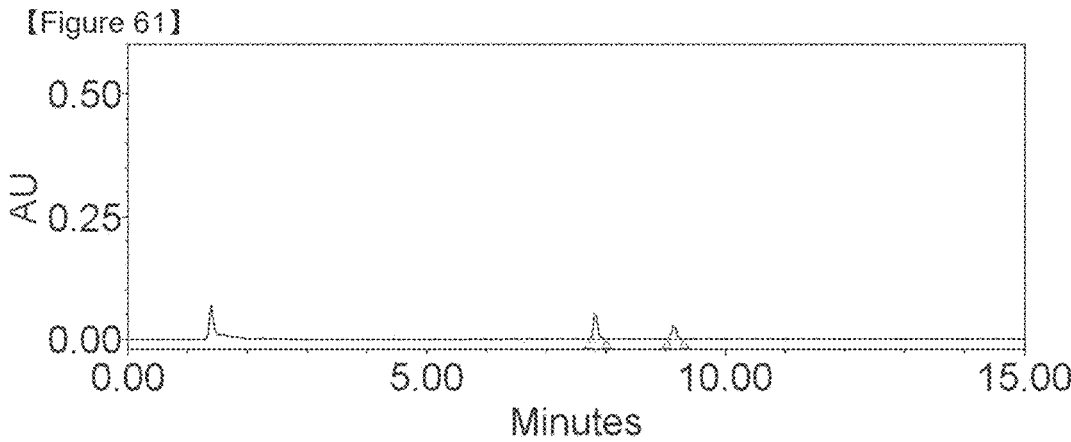
【Figure 62】
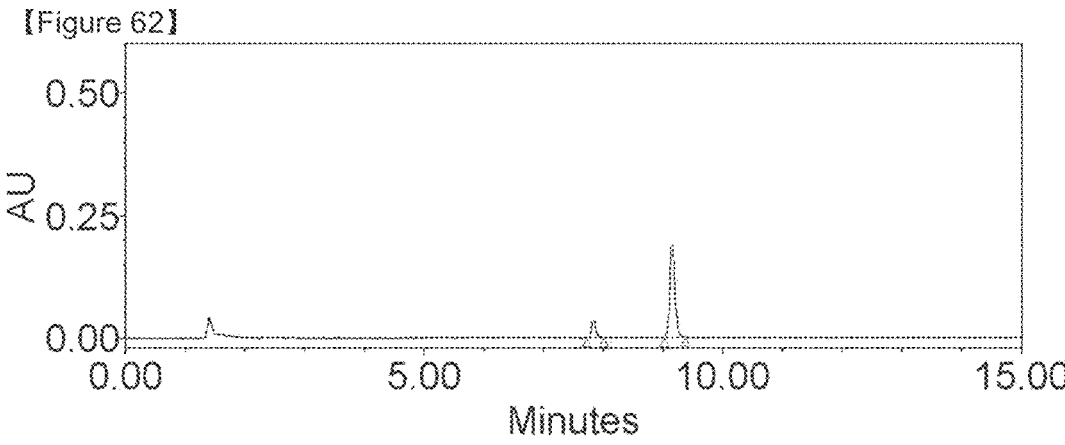

【Figure 63】
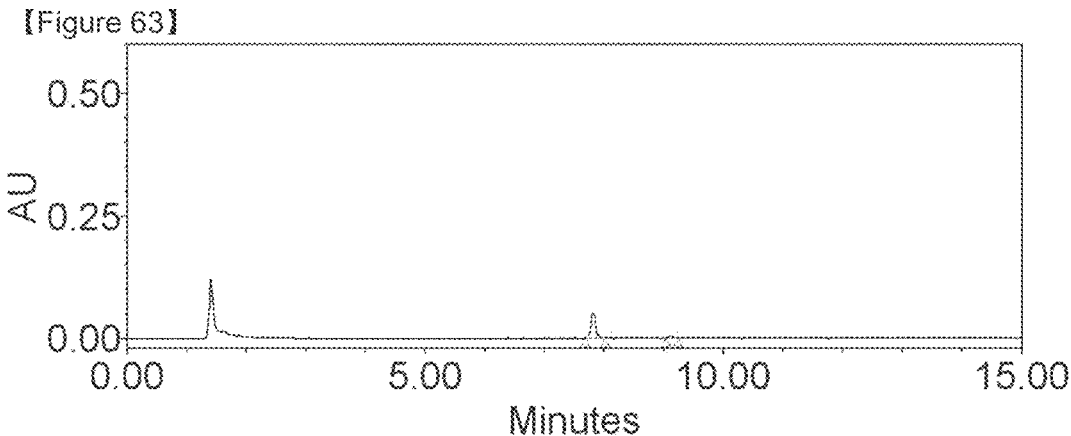
【Figure 64】
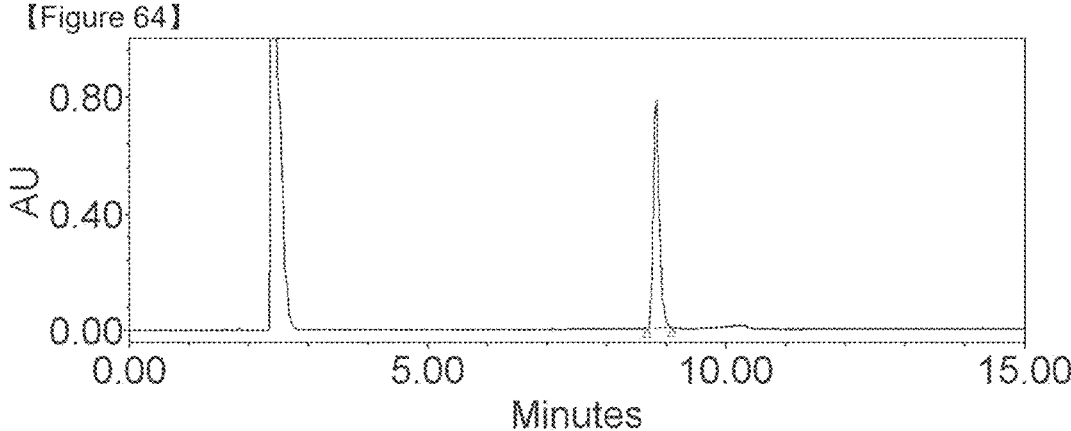
【Figure 65】
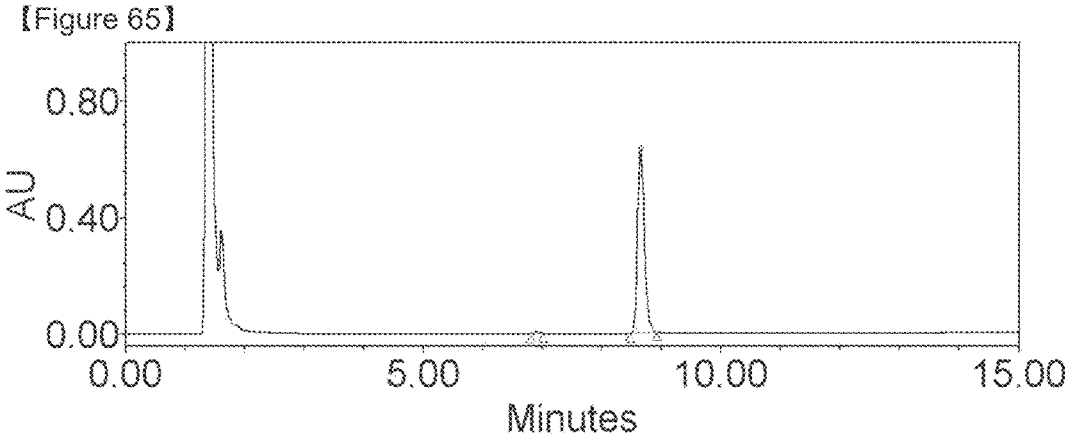

【Figure 66】
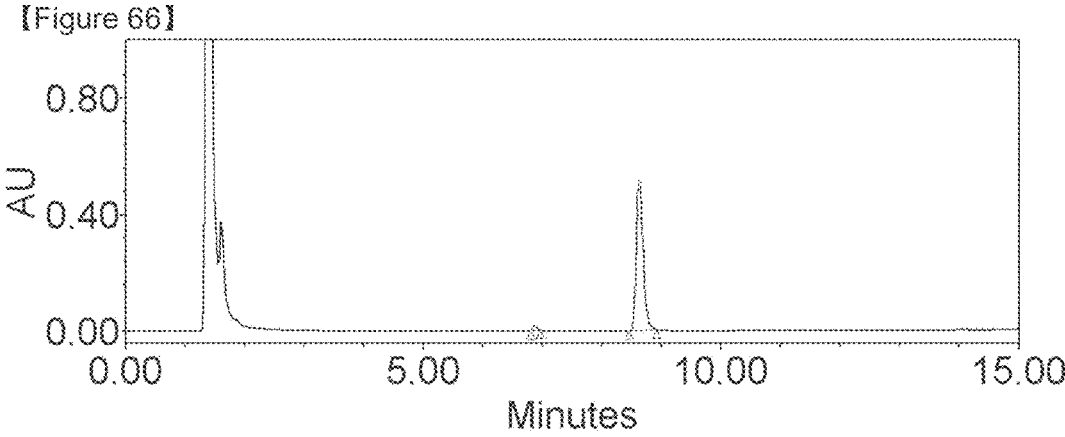
【Figure 67】
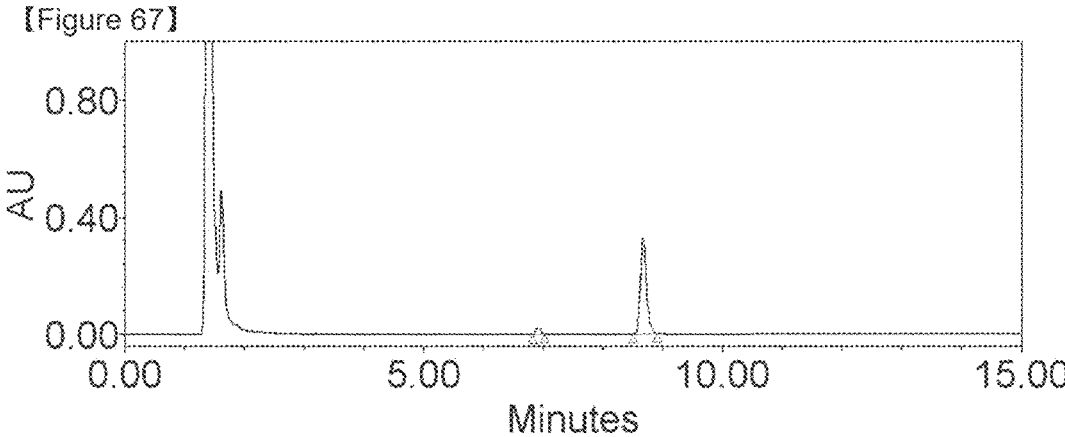
【Figure 68】
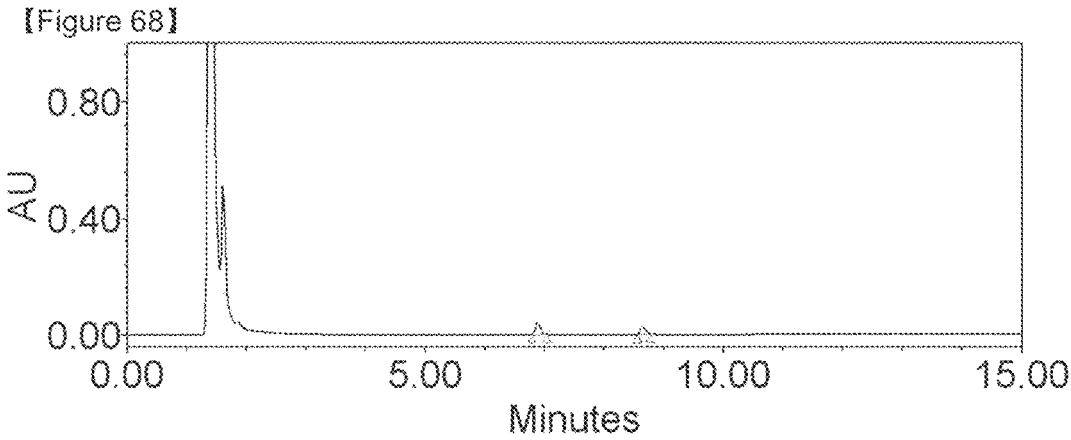

FOOD COMPOSITION FOR IMPROVING BEHAVIORAL AND MOTOR FUNCTION CONTAINING ALDEHYDE DEHYDROGENASE FOR REDUCING ALDEHYDES PRODUCED BY OXIDATION OF ALCOHOL

REFERENCE TO A SEQUENCE LISTING

In accordance with 37 CFR § 1.831, the present specification makes reference to a Sequence Listing submitted electronically s an .xml file named "Corrected_PKPA2203KRPR1USA1.xml". The .xml file was generated on Feb. 20, 2025, and is 15,166 bytes in size. The entire contents of the Sequence Listing are hereby incorporated by reference.

TECHNICAL FIELD

The present invention relates to food and pharmaceutical containing novel aldehyde dehydrogenase (ALDH) for improving behavior and motor function.

More specifically, the present invention relates to food for improving behavior and motor function and to pharmaceutical composition for inhibiting or preventing Parkinson's disease, containing an aldehyde dehydrogenase encoded by a gene having more than 98% homology to the gene of SEQ ID NO: 1, especially encoded by the gene of SEQ ID NO: 1 including SEQ ID NO: 2.

More particularly, the present invention is directed to a food or pharmaceutical compositions for improving behavior and motor function and to pharmaceutical composition for inhibiting or preventing Parkinson's disease, containing an aldehyde dehydrogenase encoded by a gene having more than 98% homology to the gene of SEQ ID NO: 1, especially encoded by the gene of SEQ ID NO: 1 including SEQ ID NO: 2, which is contained in lysate of any one or a mixture thereof selected from the group consisting of *Saccharomyces cerevisiae*, KCTC13925BP, KCTC14122BP, KCTC14123BP, KCTC14983BP, KCTC14984BP and KCTC14985BP. These strains are deposited as novel *Saccharomyces cerevisiae* having increased aldehyde dehydrogenase activity than type strain: KCTC13925BP is deposited, on Aug. 22, 2019, at the Korean Collection for Type Cultures (KCTC); KCTC14122BP and KCTC14123 are deposited, on Jan. 30, 2020, at the KCTC; KCTC14982BP, KCTC14984BP, and KCTC14985BP are deposited, on May 27, 2022, at KCTC. All strains deposited by the Applicant (Name: Pico Entech Co Ltd, Address: 43, Changeop-ro, Sujeong-gu, Seongnam-si, Gyeonggi-do, Republic of Korea) under the Budapest Treaty are available to the public under the conditions specified in 37 CFR 1.808.

BACKGROUND

Dopamine (DA) is a substance secreted from substantia nigra cells in the brain and transmits signals by increasing or decreasing the potential of adjacent nerve cells through synapses. Parkinson's disease is a disease that occurs when nerve cells that secrete dopamine die in the substantia nigra of the brain, resulting in a decrease in dopamine secretion.

Generally, neurotransmitters such as dopamine exist within the synaptic endoplasmic reticulum of nerve cells. When a signal is transmitted to a nerve cell, calcium ion channels open and calcium flows into the nerve cell. As a result, synaptic vesicles move to the cell membrane of the nerve cell. At this time, membrane fusion occurs between the endoplasmic reticulum and the cell membrane that have moved to the cell membrane, and the neurotransmitter present in the endoplasmic reticulum is released from the axon terminal to the synapse.

Dopamine is a precursor to adrenaline (epinephrine) or norepinephrine and is associated with various brain functions such as motivation, happiness, memory, and cognition. It acts as a motor neurotransmitter in the cerebral substantia nigra and plays a role in stably controlling muscles.

While adequate secretion of dopamine gives people a sense of motivation and accomplishment, decreased secretion of dopamine causes not only emotional anxiety such as depression, but also physical instability, including balance disorders. Excessive secretion of dopamine can cause hallucinations and delusions in humans.

Dopamine produces endogenous aldehydes such as DOPAL, MOPAL, DOPEGAL, and MOPEGAL through the action of monoamine oxidase (MAO) [FIG. 1, 2]. By the way, because these endogenous aldehydes are highly reactive, denatured proteins such as abnormally aggregated α-synuclein (α-Syn) accumulate in the endoplasmic reticulum of substantia nigra neurons. As a result of accumulation of these denatured proteins, endoplasmic reticulum stress may increase.

It is known that this increase in endoplasmic reticulum stress in substantia nigra cells rapidly induces neuronal cell death (apoptosis) in the substantia nigra, resulting in a decrease in dopamine secretion in the substantia nigra, leading to the development of Parkinson's disease.

In other words, denatured α-synuclein aggregate protein is deposited in the endoplasmic reticulum of substantia nigra neurons and promotes the death of substantia nigra cells, which are dopamine-secreting tissues, thereby reducing the secretion of dopamine required for normal brain operation. As a result, various symptoms occur, such as slowed movements and steps, hand tremors at rest, muscle stiffness, and postural instability, as well as decreased motor skills, decreased cognitive function, and sleep disorders.

To date, no effective drug has been developed for increasing dopamine-secreting neurons or reducing neuronal death.

Currently used therapeutic drugs are used to alleviate various symptoms or slow down the progression of Parkinson's disease. For example, a drug has been developed that temporarily allows dopamine to function in the brain by externally replenishing dopamine whose secretion amount has been reduced due to the death of substantia nigra dopamine cells. Dopamine precursors such as levodopa, dopamine agonists that activate dopamine receptors, or dopamine decomposition enzyme inhibitors are currently used as agents to relieve symptoms of Parkinson's disease.

If administration of levodopa, a dopamine supplement, continues, various side effects such as dyskinesia, motor fluctuations, and wearing-off effect may occur.

Monoamine oxidase (MAO), which is used for the purpose of inhibiting the breakdown of dopamine in the brain in Parkinson's patients, is an enzyme involved in the deamination by oxidation of dopamine, a primary amine. It is especially present in large quantities in the brain, liver, stomach, and myocardium, and has recently been attracting attention as an indicator of fibrosis that progresses from hepatitis to cirrhosis. This is because monoamine oxidase is involved in the cross-link formation reaction that converts soluble collagen into insoluble collagen.

Increased monoamine oxidase activity appears in acromegaly, progressive scleroderma, etc., where collagen metabolism, especially collagen synthesis, is enhanced. In addition, monoamine oxidase is also involved in the metabolism of noradrenaline, serotonin, and other neurotransmitters.

The present inventor had studied for a long time to develop a drug that inhibits the accumulation of denatured proteins, including alpha-synuclein aggregates, in the endoplasmic reticulum, induces a reduction in oxidative stress and endoplasmic reticulum stress, and prevents apoptosis of cerebral substantia nigra neurons, by the promotion of the decomposition and metabolism of DOPAL (dopamine originated from aldehyde), a toxic aldehyde substance generated in the process of metabolizing dopamine by monoamine oxidase (MAO) within the cerebral substantia nigra, and other derived aldehyde compounds As a result of such research, we came up with the idea that, if aldehyde dehydrogenase derived from yeast (*Saccharomyces cerevisiae*), which is similar to human aldehyde dehydrogenase, can be administered to the human body to rapidly oxidize endogenous toxic aldehydes and convert them in the form of organic acids, it is possible to inhibit and prevent the development of Parkinson's disease effectively by reducing apoptosis of dopaminergic neurons by reducing endogenous toxic aldehydes in the substantia nigra.

SUMMARY

In numerous previous studies as described above, it is revealed that denatured proteins such as alpha-synuclein aggregates can accumulate in the endoplasmic reticulum of substantia nigra neurons due to the strong reactivity of DOPANAL (dopamine inducing aldehyde), which is increased by the action of monoamine oxidase in the substantia nigra, and that this can cause death of substantia nigra neurons.

Despite many previous studies as described above, a food or pharmaceutical composition that can effectively inhibit or prevent the occurrence of Parkinson's disease by reducing apoptosis of substantia nigra cells by reducing the accumulation of denatured proteins in neural tissue through the activation of aldehyde dehydrogenase which quickly oxidize and detoxify reactive aldehydes generated during dopamine metabolism, have not yet been developed.

The primary purpose of the present invention is to provide a food composition and a pharmaceutical composition that exhibit the ability to improve behavior and motor function or to suppress and prevent Parkinson's disease, which contain an aldehyde dehydrogenase that promotes the acid conversion of endogenous aldehydes generated by the decomposition of alcohol or the oxidation of endogenous amine compounds such as dopamine, norepinephrine, serotonin, and gamma-aminobutyric acid (GABA).

Another object of the present invention is to provide a food for improving behavior and motor function and a pharmaceutical composition for inhibiting or preventing Parkinson's disease, containing an aldehyde dehydrogenase encoded by a gene having more than 98% homology to the gene of SEQ ID NO: 1, especially encoded by the gene of SEQ ID NO: 1 including SEQ ID NO: 2.

Still yet another object of the present invention is to provide a food or pharmaceutical compositions for improving behavior and motor function and a pharmaceutical composition for inhibiting or preventing Parkinson's disease, containing an aldehyde dehydrogenase which is contained in lysate of any one or a mixture thereof selected from the group consisting of *Saccharomyces cerevisiae*, KCTC13925BP, KCTC14122BP, KCTC14123BP, KCTC14983BP, KCTC14984BP and KCTC14985BP.

The objects of the present invention as described above can be accomplished by providing a food composition and a pharmaceutical composition containing a dried powder of lysate (hereinafter abbreviated as KARC) of any one or a mixture thereof selected from the group consisting of *Saccharomyces cerevisiae*, KCTC13925BP, KCTC14122BP, KCTC14123BP, KCTC14983BP, KCTC14984BP and KCTC14985BP.

The compositions of the present invention containing aldehyde dehydrogenase encoded by the gene of SEQ ID NO: 1 including SEQ ID NO: 2 contained in KARC, a dried lysate of any *Saccharomyces cerevisiae* selected from the group consisting of KCTC13925BP, KCTC14122BP, KCTC14123BP, KCTC14983BP, KCTC14984BP and KCTC14985BP, show an effect of improving behavior and motor function and also show an effect of prevention and inhibition for Parkinson's disease.

BRIEF DESCRIPTION OF DRAWINGS

FIG. 1 is a chemical formula showing the process of generating and decomposing endogenous aldehydes from ethanol and monoamines in vivo.

Ethanol or ethanol derivatives (2-substituted ethanol, R-CH2CH2-OH) are in vivo reversibly converted to acetaldehydes derivatives (R-CH2-CHO) by alcohol dehydrogenase (ADH). Acetaldehydes derivatives, highly toxic substances are irreversibly converted to relatively non-toxic Acetic acid derivatives (R—CH2—CO2H). Endogenous monoamine (R—C2H4—NH2) is converted to aldehyde (R—CH2—CHO) by monoamine oxidase (MAO) enzyme, followed by aldehyde dehydrogenase and alcohol dehydrogenase reactions detoxified to acetic acid (R—CH2—CO2H). It's the same way as alcohol metabolism.

FIG. 2 is a chemical formula showing the process of generation and metabolism of Dopamine.

Dopamine (DA), a representative monoamine neurotransmitter, is converted by monoamine oxidase (MAO) into toxic aldehyde structures as like DOPAL and MOPAL. They are decomposed by aldehyde dehydrogenase (ALDH) and eventually metabolized into relatively low-toxic Homovanillic acid (HVA).

By monoamine oxidase, dopamine is also converted via norepinephrine (NE) into DOPANAL (dopamine inducing aldehyde) as like dopegal, a known toxic substance, which is finally decomposed to be acid compound by aldehyde dehydrogenase.

In addition, dopamine metabolism does not proceed well for various reasons, such as a decrease on ALDH during the dopamine metabolic decomposition, to increase DOPANOL (dopamine inducing alcohol) such as DOPET accumulates in vivo. the reason is that DOPANAL is not converted to less toxic acid compounds.

It is known. Due to the toxicity of DOPANAL (dopamine inducing aldehyde), it is temporarily converted into DOPANOL (dopamine inducing alcohol), a relatively less toxic alcohol, and stored. When dopamine metabolism returns to its original state, DOPET, a representative DOPANOL, stored in the body is metabolized and decomposed into acid through the activation of alcohol dehydrogenase and aldehyde dehydrogenase, which are alcohol metabolism enzymes.

Despite the existence of various dopamine enzymatic metabolism pathways, when enzymatic dopamine metabolism is not progressive well, dopamine is metabolized through a non-enzymatic reaction in which it is spontaneously converted to quinone derivatives by reactive oxygen species (ROS) and then changed to neuro-melanin. In this case, it is also known to cause various diseases due to destruction of homeostasis by rapid changes in melamine distribution.

FIG. 3 is a graph showing the ability of KARC to decompose acetaldehyde in vivo.

FIG. 4 is a graph showing the ability of KARC to decompose malondialdehyde in vivo.

In animal experiments in which blood acetaldehyde [FIG. 3] and blood malondialdehyde [FIG. 4] which are endogenous toxic aldehydes, were increased by consuming alcohol, the aldehyde reduction and oxidative stress reduction effects of KARC were confirmed.

FIG. 5 is a graph showing the ability of KARC to decompose acetaldehyde in the human body.

FIG. 6 and [FIG. 7] are a graph showing the ability of KARC to decompose malondialdehyde in the human body.

In a test for confirming the reduction of endogenous blood acetaldehyde in the human body [FIG. 5] and blood malondialdehyde reduction [FIG. 6], the effect of administration of KARC appear to reduce acetaldehyde and malondialdehyde, which are biomarkers of hangover, fatigue, and cardiovascular disease. [FIG. 7] shows the effect of lowering oxidative stress by lowering malondialdehyde, a biomarker of oxidative stress and active oxygen, by administration of KARC in a state where oxidative stress was increased due to taking medicine, etc.

FIG. 8 is a protocol for MPTP model: preparation of MPTP mouse and dosage.

FIG. 9 is a protocol for Rotenone model: general preparation and dosage.

FIG. 10 is the protocol of acute neuronal inflammation model by LPS (Lipopolysaccharides).

FIG. 11 shows that the contents of DOPAL, DOPAC, and HVA within the brain of an animal model of Parkinson's disease (PD) are changed by administration of KARC of the present invention.

FIG. 12 shows the dopamine turnover index results of an animal model of Parkinson's disease (PD).

When Parkinson's disease was induced in animals using rotenone, dopamine secretion decreased. L-Dopa had no effect on restoration of decreased dopamine metabolism. On the other hand, when KARC of the present invention was administered, the decreased dopamine metabolism was restored and DOPAL was also found to decrease [FIG. 11, 12].

FIG. 13 is the result of immunostaining for changes in TH-positive neurons inside the substantia nigra pars *compacta* (SNpc) and in TH-positive fibers inside the striatum of a PD animal model by KARC oral administration.

A large amount of neuronal death in dopaminergic neurons secreting dopamine was observed by rotenone administration. As a result of the KARC treatment, it was clearly found to the preventive effect of neuronal cell death and the therapeutic effect of neurons recovered.

FIG. 14 is the result of TH-positive neuron in SNpc of PD's mouse by KARC administration.

FIG. 15 is the result of changes of TH-positive fiber of PD's mouse by KARC administration.

As a result of inducing Parkinson's disease by MPTP, the density of dopaminergic neurons in SNpc, produce and secrete dopamine due to neuronal cell death, decreased and the expression level of enzymes, promote dopamine production, decreased. Finally, dopamine secretion decreased to be observed the whitening phenomenon in substantia nigra (SNpc).

As a result of inducing Parkinson's disease by MPTP, the density of dopaminergic neurons in SNpc, produce and secrete dopamine due to neuronal cell death, decreased and the expression level of enzymes, promote dopamine production, decreased. Finally, dopamine secretion decreased to be observed the whitening phenomenon in substantia nigra (SNpc).

However, in the KARC administration group, the density of dopaminergic neurons increased [FIGS. 13, 15], the expression level of enzymes that promote dopamine production increased [FIG. 14], and the substantia nigra color was restored due to increased dopamine secretion. [FIG. 13].

Figure 16:
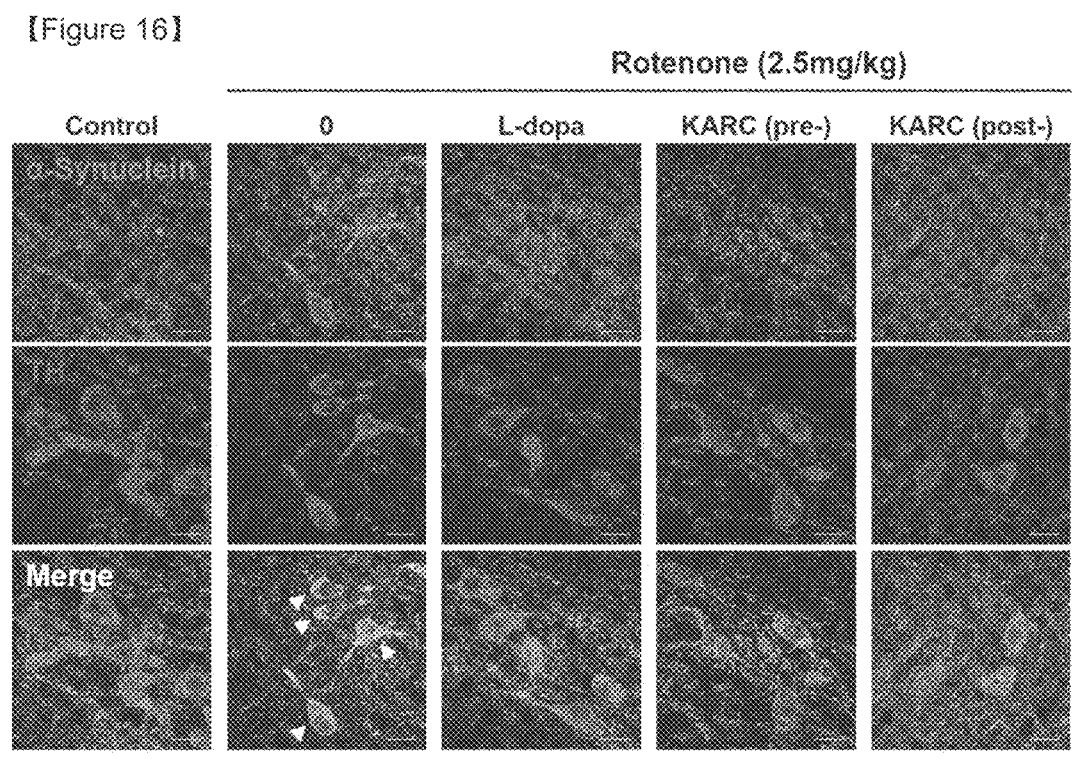

FIG. 16 shows immunostaining results for changes in TH and α-synuclein in neurons of the PD model by KARC administration.

FIG. 17 shows the results of alpha-synuclein immunostaining in neurons of the PD model by KARC administration. It was confirmed that the accumulation of alpha-synuclein aggregates abnormally increased in the substantia nigra of rotenone-induced Parkinson's disease model animals.

Alpha-synuclein aggregates, a neurotoxic substance, decreased in both the L-dopa administered group (dopamine precursor) and the KARC administrative group. [FIG. 16].

As a result of checking the density of dopamine neurons, it was confirmed that the KARC administration group recovered similarly to the L-Dopa administration group [FIG. 17].

FIG. 18 shows the rota-rod test results of the PD model by KARC of the present invention.

In Parkinson's model animals, the muscle endurance of the model animals improved depending on the KARC dose, and the high-dose group (20 units/kg) showed a higher recovery rate compared to the reference drug, Rasagiline.

FIG. 19 shows the pole test results of the PD animal model by KARC of the present invention.

In a Parkinson's animal model, it was shown that motor nerve damage was reduced in all drug administration groups (Rasagiline and KARC). Especially in the high-dose administration group of KARC (20 units/kg), it was shown the preventive effect of motor nerve damage due to Parkinson's disease, similar to that of Rasagiline, a reference drug.

FIG. 20 shows the results of the postural instability test of the PD animal model by KARC of the present invention.

FIG. 21 shows the results of the toe drag test of the PD animal model by KARC of the present invention.

FIG. 22 shows the results of the pasta handling test of the PD animal model by KARC of the present invention.

As a result of experiments on the behavior of model animals, such as postural instability and [FIG. 20], the length of stride [FIG. 21], and strength for grip the pasta [FIG. 22], it was confirmed that the symptoms of Parkinson's disease were improved in all groups (L-dopa and KARC). For the group of KARC administered for preventive purposes, it showed a better effect than the reference drug L-Dopa in improving Parkinson's disease symptoms.

FIG. 23 shows the results of immunostaining for the inflammatory response of microglia in the PD animal model using KARC of the present invention.

FIG. 24 shows the results of measuring the change in inflammatory response of microglia in a PD animal model using KARC of the present invention.

In an PD animal model of neuronal inflammation induced by LPS (In an PD animal model of neuronal inflammation induced by LPS (lipopolysaccharide), the degree of activation of microglia, known to be the cause of brain neuron death, was observed through immunostaining for Iba-1. when KARC was administrated. it was confirmed that the degree of activation of microglia in the KARC administration group decreased [FIG. 23], and at the same time, the number of activated microglia also decreased [FIG. 24].

FIG. 25 shows the results of immunostaining for the inflammatory response of astrocyte in the PD animal model using KARC of the present invention.

FIG. 26 shows the results of measuring the change in inflammatory response of astrocyte in a PD animal model using KARC of the present invention.

In PD animal model caused by neuronal inflammation, inflammation of astrocytes causes the death of brain neurons and simultaneously leads to a weakening of brain homeostasis through the creation and maintenance of cranial nerve synapses. As a result of the degree of astrocyte activation through immunostaining for GFAP which is a measure of the inflammatory response of astrocytes, the degree of abnormal inflammatory activation of astrocytes was reduced in the KARC administration group [FIG. 25], and at the same time the number of activated astrocytes was reduced [FIG. 26]. In particular, an effect of alleviating inflammation was increased by a dose-dependent manner in the KARC administration.

FIG. 27 shows changes in enzyme activity in case of oral administration of KwonP-1 strain.

FIG. 28 shows changes in enzyme activity in case of oral administration of KwonP-2 strain.

FIG. 29 shows changes in enzyme activity in case of oral administration of KwonP-3 strain.

FIG. 30 shows changes in enzyme activity in case of oral administration of Pico YP strain.

FIG. 31 shows changes in enzyme activity in case of oral administration of PicoYP-01 strain.

FIG. 32 shows changes in enzyme activity in case of oral administration of PicoYP-02 strain.

[FIGS. 27, 28, 29, 30, 31, 32] shows KwonP-1, KwonP-2, KwonP-3, PicoYP, PicoYP-01, and PicoYP-02 were orally administered under conditions (1<pH<5) similar to the digestive process of the stomach in human for 90 minutes. The change in ALDH enzyme activity were measured.

ALDH enzyme activity was maintained at a minimum of 37.29 unit/g and a maximum of 52.24% at pH=5 (similar to condition observed during food intake). It was confirmed that the enzyme activity was maintained when KARC was administered orally.

FIG. 33 shows the growth curve and enzyme activity of KwonP-1 strain cultured in a 5 L fermenter.

FIG. 34 shows the growth curve and enzyme activity of KwonP-2 strain cultured in a 5 L fermenter.

FIG. 35 shows the growth curve and enzyme activity of KwonP-3 strain cultured in a 5 L fermenter.

FIG. 36 shows the growth curve and enzyme activity of Pico YP strain cultured in a 5 L fermenter.

FIG. 37 shows the growth curve and enzyme activity of PicoYP-01 strain cultured in a 5 L fermenter.

FIG. 38 shows the growth curve and enzyme activity of PicoYP-02 strain cultured in a 5 L fermenter.

In [FIGS. 33, 34, 35, 36, 37, 38], the novel mutant strains: KwonP-1, KwonP-2, KwonP-3, PicoYP, PicoYP-01, and PicoYP-01 were respectively cultured using YPD medium in a 5 L fermenter under the same conditions. It was carried out at 30° C. and 200 rpm for 48 hours.

When comparing the growth curve (OD660 nm) and ALDH enzyme activity of each strain with that of the type strain, ALDH enzyme activity was at least 10.5 times and up to 18.75 times higher. PicoYP-01 had the highest ALDH activity at 52.68 unit/g, and KwonP-3 had the lowest at 29.5 unit/g.

FIG. 39 shows the results of oral administration of KARC in the Camk-PARIS Parkinson's disease transgenic mice.

FIG. 40 shows changes in the expression of Parkinson's disease indicator proteins such as PARIS, TH, GFAP, and Neun in the brain tissue of the Camk-PARIS Parkinson's disease transgenic mice as KARC administered orally.

When KARC (20 units/kg/day) was orally administered to Camk-PARIS Parkinson's disease transgenic mice for 4 weeks, the result of pole test showed that the T-LA value was 23 seconds, which was shortened by 36.08% compared to the KARC none-administration group. [FIG. 39].

In addition, as a result of the protein expression level was confirmed using PARIS (Parkin-interacting substrate), TH (Tyrosine hydroxylase), GFAP (Glial fibrillary acidic protein), and NeuN (Neuronal nuclei) antibodies respectively, the number of surviving neurons after KARC administration was measured. It was confirmed that Neuronal damage was recovered as NeuN increased, and GFAP activity decreased. Finally, Camk-PARIS Parkinson's disease transgenic mice, inflammation in astrocyte was reduced and neuronal damage was recovered. [FIG. 40].

FIG. 41 is the HPLC spectrum of a mixture of distilled water and DOPAL.

FIG. 42 is an HPLC spectrum after maintaining the KARC and DOPAL mixture of the present invention at 30° C. for 1 hour.

FIG. 43 is an HPLC spectrum after maintaining the KARC and DOPAL mixture of the present invention at 30° C. for 3 hours.

FIG. 44 is an HPLC spectrum after maintaining the KARC and DOPAL mixture of the present invention at 37° C. for 1 hour.

FIG. 45 is an HPLC spectrum after maintaining the KARC and DOPAL mixture at 37° C. for 3 hours.

In [FIGS. 41, 42, 43, 44, 45], when KARC was treated at 30° C., DOPAL decreased by 4.7% in 1 hour and 15.7% in 3 hours and at 37° C., the decrease in DOPAL was 13.4% in 1 hour and 24.4% after 3 hours.

DOPAC was increased at 6 minutes. Therefore, it was confirmed that KARC oxidizes DOPAL and converts it into DOPAC.

FIG. 46 is the HPLC spectrum of a mixture of distilled water and succinic semialdehyde (SSA).

FIG. 47 is an HPLC spectrum after maintaining the KARC and SSA mixture of the present invention at 37° C. for 1 hour.

FIG. 48 is an HPLC spectrum after maintaining the KARC and SSA mixture at 37° C. for 3 hours.

In [FIGS. 46, 47, 48], when KARC was treated at 37° C., there was a 55% decrease in 1 hour and a 74.9% in 3 hours. KARC oxidized SSA, metabolite of GABA.

FIG. 49 is the HPLC spectrum of a mixture of distilled water and acetaldehyde.

FIG. 50 is an HPLC spectrum after maintaining the KARC and acetaldehyde mixture of the present invention at 30° C. for 1 hour.

FIG. 51 is an HPLC spectrum after maintaining the KARC and acetaldehyde mixture of the present invention at 30° C. for 3 hours.

FIG. 52 is an HPLC spectrum after maintaining the KARC and acetaldehyde mixture of the present invention at 37° C. for 1 hour.

FIG. 53 is an HPLC spectrum after maintaining the KARC and acetaldehyde mixture at 37° C. for 3 hours.

When acetaldehyde was treated with KARC for 1 hour, acetaldehyde was oxidized 100% not only at 30° C. but also at 37° C. [FIG. 49, 50, 51, 52, 53].

FIG. 54 is the HPLC spectrum of a mixture of distilled water and glyoxal.

FIG. 55 is an HPLC spectrum after maintaining the KARC and glyoxal mixture of the present invention at 30° C. for 1 hour.

FIG. 56 is an HPLC spectrum after maintaining the KARC and glyoxal mixture of the present invention at 30° C. for 3 hours.

FIG. 57 is an HPLC spectrum after maintaining the KARC and glyoxal mixture of the present invention at 37° C. for 1 hour.

FIG. 58 is an HPLC spectrum after maintaining the KARC and glyoxal mixture at 37° C. for 3 hours.

Glyoxal, a representative aldehyde produced during energy metabolism in vivo, was reduced by 20.4% by 1 hour at 30° C. and 25.3% by 3 hours by KARC treatment. It also decreased by 23.8% at 1 hour and 23.8% at 3 hours at 37° C. [FIGS. 54, 55, 56, 57, 58].

FIG. 59 is the HPLC spectrum of a mixture of distilled water and trans-cinnamaldehyde.

FIG. 60 is an HPLC spectrum after maintaining the KARC and trans-cinnamaldehyde mixture of the present invention at 30° C. for 1 hour.

FIG. 61 is an HPLC spectrum after maintaining the KARC and trans-cinnamaldehyde mixture of the present invention at 30° C. for 3 hours.

FIG. 62 is an HPLC spectrum after maintaining the KARC and trans-cinnamaldehyde mixture of the present invention at 37° C. for 1 hour.

FIG. 63 is an HPLC spectrum after maintaining the KARC and trans-cinnamaldehyde mixture at 37° C. for 3 hours.

When treated with KARC, trans-cinnamaldehyde was reduced by 35.9% in 1 hour and 97.4% in 3 hours at 30° C., and converted to 82.4% in 1 hour and 99.6% in 3 hours at 37° C. [FIG. 59, 60, 61, 62, 63].

FIG. 64 is the HPLC spectrum of a mixture of distilled water and benzaldehyde.

FIG. 65 is an HPLC spectrum after maintaining the KARC and benzaldehyde mixture of the present invention at 30° C. for 1 hour.

FIG. 66 is an HPLC spectrum after maintaining the KARC and benzaldehyde mixture of the present invention at 30° C. for 3 hours.

FIG. 67 is an HPLC spectrum after maintaining the KARC and benzaldehyde mixture of the present invention at 37° C. for 1 hour.

FIG. 68 is an HPLC spectrum after maintaining the KARC and benzaldehyde mixture at 37° C. for 3 hours.

When treated with KARC, benzaldehyde decreased by 12.2% in 1 hour and 32.0% in 3 hours at 30° C., and converted to 57.4% in 1 hour and 97.1% in 3 hours at 37° C. [FIGS. 64, 65, 66, 67, 68].

DETAILED DESCRIPTION OF THE EMBODIMENTS

Hereinafter, the method for producing dry powder of KARC of the present invention, the lysate of *Saccharomyces cerevisiae* KCTC13925BP, KCTC14122BP, KCTC14123BP KCTC14983BP, KCTC14984BP, KCTC14985BP, will be described in more detail.

These examples are for illustrative purposes only of compositions that can achieve the purpose of the present invention, and therefore, the scope of the present invention is not limited only to the compositions described in the following examples.

[Example 1] Screening Wild Yeast Parent Strain to Proceed Mutation

In the present invention, each suspension of traditional Korean wines (hereinafter referred to as makgeolli) was prepared by mixing various types of makgeolli with a 0.9% NaCl solution. The makgeolli suspension was stirred at 200 rpm for 1 hour. The supernatant containing the yeast wild strain was diluted with YPD (yeast extract peptone dextrose broth) medium. The diluted solution was prepared to be $10^{-6}$ times the original solution.

The diluted solution was smeared on YPD agar medium. The agar medium was statically cultured at 30° C. under aerobic conditions for one week. *Saccharomyces cerevisiae* was primary screened based on morphological characteristics of colonies, growth characteristics at YM medium and microscopic observation.

The ALDH activity and glutathione content of screened *Saccharomyces cerevisiae* were measured. Parent strain was selected based on ALDH activity and glutathione production.

1-1: Measurement of Aldehyde Dehydrogenase

Acetaldehyde reacted with Dinitrophenylhydrazine (DNPH) to form acetaldehyde-hydrazone (Ach-DNPH) compound. Ach-DNPH compounds were detected at 360 nm by HPLC equipped with a C18 column. The amount of aldehyde reduced by the decomposition reaction by aldehyde dehydrogenase ALDH) was quantified through the amount of the detected Ach-DNPH compound.

The enzyme reaction was carried out at 30° C. by adding 10 ul of the yeast lysate to 990 ul reaction mixture [50 mM potassium phosphate buffer (pH 8.0), 1.5 mM acetaldehyde and 3 mM NADP+]. After the enzyme reaction was completed, 50 ul of 10 mM DNPH was added to induce the formation of Ach-DNPH. Ach-DNPH formation proceeded at 22° C. for 1 hour.

Ach-DNPH formation was terminated by addition of 3 M sodium acetate (pH 9). The Ach-DNPH compound formed was separated by adding twice volume of acetonitrile. The separated Ach-DNPH compound (in ACN) was analyzed by injection into HPLC.

The concentration of the Ach-DNPH compound was analyzed at a wavelength of 360 nm by setting HPLC under the condition of developing a mobile phase (acetonitrile, water) on a C18 column at a rate of 1 ml/min. The area value of the chromatogram obtained as a result of HPLC was converted using the material standard curve of aldehyde-DNPH (Sigma-Aldrich) to quantify the concentration of the Ach-DNPH compound. The reduced concentration of Ach-DNPH per minute, 1 mM, was calculated as 1 unit of ALDH. The activity of ALDH was standardized as Unit/mg-protein.

1-2: Glutathione Measurement

Yeast cells were harvested by centrifuging 1 ml of *Saccharomyces cerevisiae* culture medium. A suspension was prepared by adding 1 ml of water to the harvested yeast cells. Glutathione was extracted by stirring the suspension at 1,000 rpm at 85° C. for 2 hours. The suspension was centrifuged to remove yeast cells, and the supernatant was filtered through a 0.22 μm filter to obtain a sample containing glutathione.

The concentration of glutathione in the sample was analyzed by HPLC (Shimazu LC-20AD) equipped with a C18 column. The concentration of glutathione was analyzed at a wavelength of 210 nm under conditions in which the mobile phase (2.02 g/L Sodium 1-heptanesulfonate monohydrate, 6.8 g/L Potassium dihydrogen phosphate, pH 3.0, methanol mixture) was developed at a rate of 1 ml/min. The area value of the chromatogram obtained as a result of HPLC was analyzed using the standard curve of glutathione.

ALDH activity and glutathione content were analyzed for 200 different types of yeast obtained from Korean makgeolli. The 10 types of yeast listed in [Table 1] had higher ALDH activity or glutathione production ability than other yeasts.

The ALDH activity of Yeast #97 was 0.10 Unit/mg-protein, the second highest overall. The glutathione content of Yeast #97 was 0.42%, the highest among all. yeast #97 was selected as the parent strain and a mutation induction procedure was performed.

TABLE 1

| strain | ALDH activity (Unit/mg-protein) | Glutathione content (%) | Screening |
|---|---|---|---|
| Yeast #6 | 0.06 | 0.38 | |
| Yeast #18 | 0.11 | 0.14 | |
| Yeast #22 | 0.08 | 0.38 | |
| Yeast #41 | 0.14 | 0.22 | |
| Yeast #97 | 0.10 | 0.42 | Selected parent strain (Wild-Type) |
| Yeast #109 | 0.10 | 0.36 | |
| Yeast #112 | 0.09 | 0.40 | |
| Yeast #126 | 0.10 | 0.28 | |
| Yeast #168 | 0.11 | 0.38 | |
| Yeast #197 | 0.08 | 0.41 | |

[Example 2] Identification of the Parent Strain Used in the Mutagenesis Process

Identification was performed to confirm the exact species of the wild-type parent strain (Yeast #97, Wild-type yeast). To ensure sufficient yeast cells for DNA extraction, only colonies of a single yeast were plated on YPD agar medium. DNA was extracted using a Genomic DNA prep kit (Hi-Gene™, BIOFACT Co., Ltd., Daejeon, Korea) according to the manufacturer's instructions.

To amplify rRNA gene on ITS region of the yeast, polymerase chain reaction (PCR) was performed on yeast chromosomal DNA using the ITS5 (forward) and ITS4 (reverse) primers. DNA sequencing of PCR result was analyzed.

The DNA sequence of the parent strain was isolated using the Bioedit program. The reverse strand of the PCR result was converted into a paired base sequence through a reverse completion process.

It was confirmed that the sequence of the forward strand matched the paired sequence of the reverse strand by the Cluster X program. The parent strain which was matching the sequence information confirmed through the above experimental process was identified by using the BLAST database provided by the U.S. National Center for Biotechnology Information (NCBI). As a result of identification, it was found that rRNA in the ITS of the parent strain was 100% identical to that of Saccharomyces cerevisiae.

[Example 3] Selection of Mutant Strains with Improved Aldehyde Dehydrogenase Production The mutation induction process for the wild-type Saccharomyces cerevisiae parent strain was conducted according to the method described in U.S. patent application Ser. No. 17/176,365.

To induce mutations in the yeast parent strain, wild yeast strains that produce both ALDH and glutathione were treated with ethyl methane sulfonate (EMS) or nitrosoguanidine (NGD). Yeast strains in which mutations were induced were exposed to various concentrations of methylglyoxal. A mutant strain with excellent adaptability to methylglyoxal was selected. Selected yeast strains were exposed to various concentrations of lysine. A mutant strain with excellent adaptability to lysine was selected. Thirty mutant strains with excellent adaptability to methylglyoxal and lysine were obtained. Each of the 30 yeasts was evaluated through five characteristics: growth curve, ALDH activity, ADH activity, coenzyme content, and glutathione content.

3-1: Growth Characteristics

Saccharomyces cerevisiae is a crab tree positive microorganism and produces ethanol simultaneously with growth under aerobic conditions. Cultivating yeast with high yields requires Saccharomyces cerevisiae with high ethanol tolerance.

YPD media with different ethanol concentrations (no ethanol, 5%, 7%, and 10%) were prepared. Culture medium of Saccharomyces cerevisiae (yeast) adjusted to OD=1 at 660 nm was prepared. Each mixture of the prepared YPD medium and yeast culture medium was diluted at a ratio of 99:1. Finally, YPD media containing yeast with four different concentrations of alcohol were prepared. Each YPD medium mixed with yeast was cultured with shaking at 30° C. and 200 rpm. The growth curve of the mutant strain was measured every 3 hours for 48 hours. The growth curve of each mutant strains are evaluated through three characteristics: time (or period) of lag phase, specific growth rate OD660 nm/hr) of exponential phase, and maximum density OD660 nm).

The higher concentration of ethanol in YPD medium, the longer the time taken for the lag phase. The maximum density and specific growth rate decreased. As a result of comparing the maximum density of mutant strains at low concentration (ethanol 5%) and high concentration (ethanol 10%), it was found that in the case of nine mutant strains, 50% of growth was even maintained at high concentration compared to growth at low concentration. The growth characteristics of the nine mutant strains that distinguished them from other strains were a short lag phase and a high specific growth rate.

TABLE 2

| # | 5% ethanol | | | 7% ethanol | | | 10% ethanol | | | |
|---|---|---|---|---|---|---|---|---|---|---|
| # | hr | $OD_{660\,nm}$/hr | $OD_{660\,nm}$ | hr | $OD_{660\,nm}$/hr | $OD_{660\,nm}$ | hr | $OD_{660\,nm}$/hr | $OD_{660\,nm}$ | Selection |
| 1 | 9 | 0.6477 | 22.2 | 15 | 0.5210 | 16.5 | 24 | 0.1968 | 4.81 | |
| 2 | 12 | 0.3675 | 12.34 | 24 | 0.1835 | 4.11 | 36 | 0.0140 | 0.212 | |
| 3 | 9 | 0.4285 | 15.8 | 15 | 0.2888 | 9.12 | 24 | 0.0880 | 2.16 | |
| 4 | 15 | 0.9683 | 25.3 | 15 | 0.8815 | 25.3 | 15 | 0.4085 | 12.4 | K-1 |
| 5 | 12 | 0.7368 | 14.12 | 15 | 0.7337 | 12.23 | 21 | 0.2205 | 5.68 | |

TABLE 2-continued

| # | 5% ethanol | | | 7% ethanol | | | 10% ethanol | | | |
|---|---|---|---|---|---|---|---|---|---|---|
| # | hr | $OD_{660\,nm}$/hr | $OD_{660\,nm}$ | hr | $OD_{660\,nm}$/hr | $OD_{660\,nm}$ | hr | $OD_{660\,nm}$/hr | $OD_{660\,nm}$ | Selection |
| 6 | 12 | 0.2590 | 9 | 15 | 0.1773 | 5.44 | 33 | 0.0353 | 0.448 | |
| 7 | 24 | 0.9664 | 22.3 | 27 | 0.8467 | 16.8 | 30 | 0.2673 | 5.17 | |
| 8 | 6 | 0.7268 | 23 | 9 | 0.6222 | 21.5 | 15 | 0.3778 | 12.11 | K-2 |
| 9 | 6 | 0.8433 | 22.12 | 9 | 0.7484 | 25.34 | 15 | 0.3005 | 9.41 | |
| 10 | 3 | 0.4880 | 14.5 | 18 | 0.2013 | 6.12 | 24 | 0.0808 | 2.14 | |
| 11 | 3 | 0.2766 | 11.15 | 9 | 0.2223 | 8.22 | 24 | 0.0988 | 2.41 | |
| 12 | 6 | 0.7149 | 21.68 | 9 | 0.5969 | 20.52 | 12 | 0.3317 | 11.4 | K-3 |
| 13 | 9 | 0.6106 | 22.4 | 12 | 0.4906 | 16.4 | 15 | 0.1813 | 5.68 | |
| 14 | 12 | 0.6136 | 20.6 | 24 | 0.3060 | 6.85 | 36 | 0.0278 | 0.41 | |
| 15 | 12 | 0.4759 | 15.45 | 18 | 0.1751 | 5.41 | 33 | 0.0707 | 0.896 | |
| 16 | 9 | 0.8533 | 23.8 | 15 | 0.8065 | 20.9 | 21 | 0.4953 | 12.1 | K-4 |
| 17 | 21 | 0.6016 | 14.85 | 24 | 0.3955 | 8.45 | 24 | 0.0547 | 1.26 | |
| 18 | 12 | 0.7766 | 19.25 | 18 | 0.4437 | 12.4 | 24 | 0.1219 | 2.85 | |
| 19 | 3 | 0.5050 | 14.75 | 9 | 0.4463 | 14.6 | 21 | 0.2521 | 6.23 | |
| 20 | 27 | 0.0666 | 1.41 | 36 | 0.0278 | 0.36 | — | — | — | |
| 21 | 3 | 0.6044 | 22.14 | 9 | 0.6051 | 20.64 | 12 | 0.3247 | 11.1 | K-5 |
| 22 | 24 | 0.5798 | 13.4 | 27 | 0.5080 | 10.1 | 30 | 0.1604 | 3.1 | |
| 23 | 15 | 0.6455 | 16.9 | 15 | 0.5877 | 16.9 | 15 | 0.2003 | 6.3 | |
| 24 | 3 | 0.7269 | 20.4 | 6 | 0.6375 | 18.6 | 12 | 0.3522 | 10.5 | K-6 |
| 25 | 9 | 0.4858 | 16.7 | 15 | 0.3908 | 12.4 | 24 | 0.1476 | 3.6 | |
| 26 | 6 | 0.6559 | 17.2 | 9 | 0.5821 | 19.7 | 15 | 0.3177 | 9.6 | K-7 |
| 27 | 9 | 0.2857 | 10.5 | 15 | 0.1925 | 6.1 | 24 | 0.0587 | 1.4 | |
| 28 | 12 | 0.6315 | 12.1 | 15 | 0.6289 | 10.5 | 21 | 0.1890 | 4.9 | |
| 29 | 6 | 0.5451 | 17.3 | 9 | 0.4667 | 16.1 | 15 | 0.2834 | 9.1 | K-8 |
| 30 | 9 | 0.7826 | 21.8 | 9 | 0.6614 | 19.9 | 15 | 0.3267 | 10.6 | K-9 |

3-2: Activity of Alcohol Dehydrogenase (ADH) and Aldehyde Dehydrogenase (ALDH)

The activity of alcohol dehydrogenase (ADH) was measured by adding 10 ul of yeast lysate to 990 ul of the reaction mixture with the composition of 50 mM potassium phosphate buffer (pH 8.0), 2 mM NAD+ and 1% ethanol. The activity of aldehyde dehydrogenase (ALDH) was measured by adding 10 ul of yeast lysate to 990 ul of the reaction mixture with the composition of 50 mM potassium phosphate buffer (pH 8.0), 3 mM NAD+ and 1.5 mM acetaldehyde. The enzymatic reaction of ADH and ALDH was carried out at 30° C. for 5 minutes, and the concentration of NAD(P)H produced as a result of the enzyme reaction was measured through absorbance at 340 nm.

The enzyme activities of nine mutant strains (K-1 to K-9) selected in the present invention were measured. The ADH activity of the mutant strain was a minimum of 382.69 units/g and a maximum of 975.29 units/g. The ADH activity of the mutant strain increased at least 5.1 times and up to 13.1 times compared to the type strain (reference yeast, *Saccharomyces cerevisiae* KCTC7296). The ALDH activity of the mutant strain was a minimum of 15.23 unit/g and a maximum of 72.16 unit/g. The ALDH activity of the mutant strain increased by at least 5.3 and up to 24.9 times compared to the enzyme activity of the type-strain.

Six mutant strains (K-1, 4, 6, 7, 8, and 9) showed similar increase rate of enzyme activity of ADH and ALDH compared to the type strain. The enzyme activity of ALDH in the three mutant strains (K-2, 3, and 5) was 18.3, 23.2 and 24.9 times higher, respectively, compared to the type-strain. The enzyme activity of ADH in the three mutant strains (K-2, 3, and 5) was 9.7, 11.6, and 13.1 times higher respectively, compared to the type-strain. The rate of increase in enzyme activity of ALDH for the three mutant strains (K-2, 3, and 5) was twice as high as that of ADH.

The present inventors named three novel mutant strains (K-2, 3, and 5) adapted to increase aldehyde dehydrogenase (ALDH) activity as PicoYP, PicoYP-01, and PicoYP-02, respectively. The three novel mutant strains were deposited at the Korea Research Institute of Bioscience and Biotechnology's Biological Resources Center and were assigned the deposit numbers of KCTC14983BP, KCTC14984BP, and KCTC14985BP, respectively.

3-3: Content of Coenzyme (NAD and NADP)

NADtotal and NADPtotal in lysates extracted from mutant strains were measured with NADH/NAD+assay kit and NADPH/NADP+assay kit, respectively. NAD(P) in the sample was converted to NAD(P)H using NAD(P) cycling buffer and NAD(P) cycling enzyme mix. The chromophoric test reaction was induced with NAD(P) developer measured as absorbance at 450 nm. The chromophoric test reaction was measured as absorbance at 450 nm. The absorbance of the samples was plugged into the equation corresponding to the standard curve, and the NAD(P) total was calculated in the yeast lysate.

The coenzyme content of nine mutant strains (K-1 to K-9) selected in the present invention was measured. The NAD-total of the mutant strains had a minimum of 126 nmole/g and a maximum of 195 nmole/g. The NADtotal of the mutant strain increased at least 7.3 times and up to 10.8 times compared to the type-strain. The NADPtotal content of the mutant strain was a minimum of 2.4 nmole/g and a maximum of 5.8 nmole/g. The NADP total content of the mutant strain increased at least 11.4 times and up to 27.6 times compared to the type-strain.

In the six mutant strains (K-1,4,6,7,8,9), the increase rate of NADPtotal was less than twice the increase rate of NADtotal. The NADPtotal content increase rates of the three novel mutant strains (PicoYP, PicoYP-01, and PicoYP-02) were 25.7, 22.9, and 27.6 times, respectively. The NAD total content increase rates of the three novel mutant strains were 10.8, 9.9, and 11.3 times, respectively. The NADPtotal increase rate of the three novel mutant strains was more than twice the NADtotal increase rate.

3-4: Content of Glutathione (GSH)

The glutathione content of the nine mutant strains was measured in the same manner as Example 1-2. The glutathione content of the mutant strains ranged from a minimum of 0.85% to a maximum of 1.05%. The glutathione content of the mutant strain increased at least 2.7 times and up to 3.3 times compared to the type strain. In three novel mutant strains (PicoYP, PicoYP-01, PicoYP-02), the increase rate of ALDH activity and coenzyme content were higher compared to others.

The three novel mutant yeasts (PicoYP, PicoYP-01, PicoYP-02) had similar glutathione production abilities to the existing deposited strains (Kwon P-1, Kwon P-2, Kwon P-3). The three novel mutant yeasts had significantly increased ADH and ALDH enzyme activities and coenzyme contents compared to the existing deposited strains.

secured and extracted from the stage of exponential growth phase. To eliminate the influence of the carbon source contained in the residual YPD medium, the yeast was washed three times using a centrifuge. A yeast suspension of 2 McFarland concentration was prepared using API 50 CHL medium. The prepared yeast suspension was filled into the tube of the strip. The strip onto which the suspension was dispensed was cultured at 30° C. for 24 hours.

API 50 CHL medium used for API testing was purple. When acids were produced through energy metabolism, API 50 CHL medium turns blue, green, and finally yellow. In the end, it was recorded which type of carbon source was used

TABLE 3

| Strain | Enzyme activity | | Coenzyme concentration | | GSH | | |
|---|---|---|---|---|---|---|---|
| | ADH | ALDH | $NAD_{total}$ | $NADP_{total}$ | (%) | | Name |
| Type-strain | 74.6 | 2.9 | 17.2 | 0.21 | 0.32 | Reference yeast | KCTC7296 |
| K-1 | 542.26 | 23.11 | 169.8 | 4.1 | 1.00 | KwonP-1 | KCTC13925BP |
| K-2 | 725.11 | 53.1 | 185 | 5.4 | 0.86 | PicoYP | KCTC14983BP |
| K-3 | 866.41 | 67.4 | 171 | 4.8 | 0.85 | PicoYP-01 | KCTC14984BP |
| K-4 | 625.11 | 31.4 | 176 | 5.1 | 0.98 | KwonP-2 | KCTC14122BP |
| K-5 | 975.29 | 72.16 | 195 | 5.8 | 0.89 | PicoYP-02 | KCTC14985BP |
| K-6 | 458.88 | 16.21 | 154 | 3.1 | 1.05 | — | |
| K-7 | 382.69 | 15.23 | 126 | 2.4 | 1.00 | — | |
| K-8 | 422.17 | 16.19 | 142 | 2.9 | 0.99 | — | |
| K-9 | 533.54 | 20.68 | 167 | 3.2 | 1.00 | KwonP-3 | KCTC14123BP |

TABLE 4

| Strain | Enzyme activity | | Coenzyme concentration | | GSH | | |
|---|---|---|---|---|---|---|---|
| | ADH | ALDH | $NAD_{total}$ | $NADP_{total}$ | (%) | | Name |
| Type-strain | 1 | 1 | 1 | 1 | 1 | Reference yeast | KCTC7296 |
| K-1 | 7.3 | 8.0 | 9.9 | 19.5 | 3.1 | KwonP-1 | KCTC13925BP |
| K-2 | 9.7 | 18.3 | 10.8 | 25.7 | 2.7 | PicoYP | KCTC14983BP |
| K-3 | 11.6 | 23.2 | 9.9 | 22.9 | 2.7 | PicoYP-01 | KCTC14984BP |
| K-4 | 8.4 | 10.8 | 10.2 | 17.1 | 3.1 | KwonP-2 | KCTC14122BP |
| K-5 | 13.1 | 24.9 | 11.3 | 27.6 | 2.8 | PicoYP-02 | KCTC14985BP |
| K-6 | 6.2 | 5.6 | 9.0 | 14.8 | 3.3 | — | |
| K-7 | 5.1 | 5.3 | 7.3 | 11.4 | 3.1 | — | |
| K-8 | 5.7 | 5.6 | 8.3 | 13.8 | 3.1 | — | |
| K-9 | 7.2 | 7.1 | 9.7 | 15.2 | 3.1 | KwonP-3 | KCTC14123BP |

[Example 4] Comparison of Carbon Source Preference

It was investigated the carbon source preference for growth of three mutant strains (KwonP-1, KwonP-2, KwonP-3) with high ALDH and glutathione, for which a domestic patent application was filed on Feb. 18, 2020. Various carbon sources used by the reference yeast strain (KCTC7296) for growth were measured. To find the maximum ability of producing ALDH, it was investigated the carbon source preference for growth of three new mutant strains (PicoYP, PicoYP-01, and PicoYP-02).

The characteristic and novelty of carbon source preference of strains was analyzed by API 50 CHL kit (API systems, BIOMERIEUX, SA, France).

Preparing the 15 ml of conical tube included 8 ml of YPD medium. Each of the seven mutant strains was inoculated into the prepared conical tube.

After culturing the inoculated conical tubes at 30° C. and 200 rpm for 24 hours, each of the seven mutant strains was by mutant strains based on the color change as like: Purple x, Blue+, Green++, and Yellow+++.

All of the seven mutant strains tested used 19 kinds of carbon sources for energy production and growth: L-arabinose, ribose, D-xylose, D-galactose, D-glucose, D-fructose, D-mannose, mannitol, N-acetyl-glucosamine, arbutin, salicin, cellobiose, maltose, lactose, melibiose, sucrose, trehalose, raffinose, gentiobiose.

Rhamnose was used by only three mutant strains: KwonP-1, PicoYP-01, PicoYP-02. Sorbitol was used by four mutant strains: KwonP-1, KwonP-3, PicoYP-01, PicoYP-02. α-methyl-D-mannoside was used by four mutant strains: type strain, KwonP-1, KwonP-2, PicoYP-02. Amygdalin was used by six mutant strains: KwonP-1, KwonP-2, KwonP-3, PicoYP, PicoYP-01, PicoYP-02. D-turanose was used by four mutant strains: type-strain, KwonP-1, KwonP-3, PicoYP-02. D-tagatose was used by three mutant strains: type-strain, KwonP-3, PicoYP-3. Gluconate was used only by type-strain.

Mannitol and sorbitol, which correspond to alcoholic carbon sources, had a significant effect on yeast growth. The three types of novel mutant strains differed from the other four types of yeast in the type of sugar used for growth. The use of the preferred alcoholic carbon source was slightly different between the three new mutant strains (PicoYP, PicoYP-01 and PicoYP-02) [Table 5].

TABLE 5

| | Reference yeast | Kwon P-1 | Kwon P-2 | Kwon P-3 | Pico YP | Pico YP-01 | Pico YP-02 |
|---|---|---|---|---|---|---|---|
| L-Arabinose | ++ | +++ | ++ | +++ | ++ | ++ | +++ |
| Ribose | +++ | +++ | +++ | +++ | +++ | +++ | +++ |
| D-Xylose | + | ++ | + | + | ++ | ++ | + |
| D-Galactose | + | +++ | ++ | ++ | +++ | ++ | ++ |
| D-Glucose | ++ | +++ | +++ | ++ | +++ | ++ | ++ |
| D-Fructose | ++ | +++ | ++ | ++ | +++ | ++ | ++ |
| D-Mannose | ++ | +++ | +++ | ++ | +++ | ++ | ++ |
| Rhamnose | | + | | | | ++ | ++ |
| Mannitol | + | + | + | + | ++ | +++ | +++ |
| Sorbitol | | | + | + | | +++ | +++ |
| α-Methyl-D-Mannoside | +++ | + | + | | | | +++ |
| N-Acetyl-Glucosamine | +++ | +++ | +++ | +++ | +++ | +++ | +++ |
| Amygdalin | | + | + | + | ++ | ++ | ++ |
| Arbutin | +++ | +++ | +++ | +++ | +++ | +++ | +++ |
| Salicin | +++ | +++ | +++ | +++ | +++ | +++ | +++ |
| Cellobiose | +++ | +++ | +++ | +++ | +++ | +++ | +++ |
| Maltose | ++ | +++ | +++ | +++ | +++ | +++ | +++ |
| Lactose | ++ | ++ | ++ | ++ | ++ | ++ | ++ |
| Melibiose | ++ | + | +++ | +++ | ++ | ++ | +++ |
| Sucrose | ++ | +++ | ++ | ++ | +++ | +++ | ++ |
| Trehalose | ++ | + | ++ | ++ | ++ | ++ | ++ |
| Raffinose | ++ | + | + | ++ | ++ | ++ | +++ |
| Gentiobiose | ++ | ++ | ++ | ++ | ++ | ++ | ++ |
| D-Turanose | + | + | | + | | | + |
| D-Tagatose | ++ | | | + | | | ++ |
| Gluconate | + | | | | | | |

[Example 5] Changes in ALDH Activity of Mutant Strains in Gastric Juice

When KARC is administered orally, in order for the enzyme activity to be maintained in the intestine, the enzyme activity must be passed safely without being destroyed by stomach acid, which secretes powerful proteolytic enzymes such as pepsin.

NaOH solution was added to artificial gastric fluid at pH=1.17 to artificially generate two simulated solutions at pH=3 and pH=5, which resemble the human gastric environment during food digestion. 1 g of KARC was added to 7 ml of artificial gastric fluid and 7 ml of two simulated solutions and mixed at 36.5° C. for 5, 30, 60, and 90 min respectively. NaOH solution was added to reaction mixture to adjust acidity to pH=7, respectively. 10 ml of sample for analysis were taken from the adjusted solution at pH=7, respectively. The activity of ALDH was analyzed from each sample.

Under the condition of pH=1.17, the ALDH activity of the sample decreased by more than 92.88% compared to the control group during 5 minutes of reaction. Under the condition of pH=1.17, the ALDH activity of the sample decreased by an average of 98.89% for 90 minutes. The ALDH activity of the samples decreased by an average of 96.66% over 90 min at pH=3 and 56.83% at pH=5. Ultimately the ALDH activity at pH=3 and 5 remained relatively higher than that at pH=1.17 during the 90-min reaction.

In detail, the ALDH activity of KwonP-1 (KCTC13925BP) at pH=1.17 decreased by 90.94% compared to the control group to 5.57 unit/g when reacted for 5 minutes. The ALDH activity of KwonP-1 decreased by 98.57% to 0.88 unit/g for 90 minutes [FIG. 27]. The enzyme activity at pH=3 and pH=5 remained relatively higher than at pH=1.17. When reacted for 90 minutes, the ALDH activity of KwonP-1 decreased by 96.66% to 5.57 units/g at pH=3, and decreased by 98.57% to 0.88 units/g at pH=5.

The ALDH activity of KwonP-2 (KCTC14122BP) at pH=1.17 decreased by 91.18% to 5.43 unit/g when reacted for 5 minutes. The ALDH activity of KwonP-2 decreased by 98.81% to 0.73 unit/g for 90 minutes [FIG. 28]. At pH 3 and pH 5, higher enzyme activity was maintained than at pH 1.17. When reacted for 90 minutes, the ALDH activity decreased by 97.62% to 1.47 units/g at pH=3, and decreased by 56.11% to 26.99 units/g at pH=5.

The ALDH activity of KwonP-3 (KCTC14123BP) at pH=1.17 decreased by 89.99% to 6.16 unit/g when reacted for 5 minutes. The ALDH activity of KwonP-3 decreased by 97.85% to 1.32 unit/g for 90 minutes [FIG. 29]. At pH 3 and pH 5, higher enzyme activity was maintained than at pH 1.17. When reacted for 90 minutes, the ALDH activity decreased by 92.61% to 4.55 units/g at pH=3, and decreased by 62.31% to 22.18 units/g at pH=5.

The ALDH activity of PicoYP (KCTC14983BP) at pH=1.17 decreased by 92.84% to 4.40 unit/g when reacted for 5 minutes. The ALDH activity of PicoYP decreased by 98.33% to 1.03 unit/g for 90 minutes [FIG. 30]. Higher enzyme activity was maintained at pH 3 and pH 5. When reacted for 90 minutes, the ALDH activity decreased by 96.66% to 2.05 units/g at pH=3, and decreased by 53.97% to 28.31 units/g at pH=5.

The ALDH activity of PicoYP-01 (KCTC14984BP) at pH=1.17 decreased by 95.71% to 2.64 unit/g when reacted for 5 minutes. The ALDH activity of PicoYP-01 decreased by 99.76% to 0.15 unit/g for 90 minutes [FIG. 31]. At pH 3 and pH 5, higher enzyme activity was maintained than gastric fluid. When reacted for 90 minutes, the ALDH activity decreased by 98.21% to 1.10 units/g at pH=3, and decreased by 58.74% to 25.38 units/g at pH=5.

The ALDH activity of PicoYP-02 (KCTC14985BP) at pH=1.17 decreased by 96.66% to 2.05 unit/g when reacted for 5 minutes. The ALDH activity of PicoYP-02 decreased by 99.76% to 0.15 unit/g for 90 minutes [FIG. 32]. At pH 3 and pH 5, higher enzyme activity was maintained than in gastric juice. When reacted for 90 minutes, the ALDH activity decreased by 98.21% to 1.10 units/g at pH=3, and decreased by 62.08% to 23.32 units/g at pH=5.

pH 1.17 is the pH of the raw gastric juice secreted. When you eat food, the pH rises from 3 to 5 when raw gastric fluids and food mix in the stomach, so it is unlikely that a pH of 1.17 will be reached. Nevertheless, ALDH activity in the mutant strain was retained even at pH 1.17, which is an extreme condition.

In the end, the ALDH enzyme activity of the novel mutant strains (PicoYP, PicoYP-01, PicoYP-02) was maintained at 2 unit/g to 5 unit/g even though it decreased from 92% to 97% under strongly acidic conditions of pH=1.17. 2-5 units of enzyme activity remain, which is sufficient to function in the intestines. It even remained higher at pH=3 and pH=5 compared to pH=1.17. This was the reason for reaching the conclusion that new mutant strains (PicoYP, PicoYP-01, PicoYP-02) could be administered orally.

[Example 6] Growth Characteristics of 5 L Fermenter Cultures

Each was inoculated into YPD medium (2% peptone, 1% yeast extract, 2% glucose) and primary seed culture was performed at 30° C. and 200 rpm for 18 hours. 20 ml of cultured seed was inoculated into 1980 ml of YPD medium and cultured again in 5 L. Cultivation in a 5 L culture tank was carried out at 30° C. and 200 rpm for 48 hours. Growth curve at OD660 nm and enzyme activity were analyzed using 10 ml of sample collected from secondary culture.

The maximum density (OD660 nm) of KwonP-1 (KCTC13925BP) was 134.4. The maximum density of KwonP-1 was 4.35% higher than that of the type-strain (KCTC7296). The growth curve characteristics and specific growth rate (OD660 nm/hr) of KwonP-1 were similar to those of the type-strain. The ALDH activity of KwonP-1 was 33.6 unit/g. The ALDH activity of KwonP-1 was 11.96 times higher than that of the type-strain [FIG. 33].

The maximum density (OD660 nm) of KwonP-2 (KCTC14122BP) was 133.8. The maximum density of KwonP-2 was 3.88% higher than that of the type-strain. The growth of KwonP-2 ended earlier than that of the type-strain. The specific growth rate (OD660 nm/hr) of KwonP-2 was 14.8% higher than that of the type-strain. The ALDH activity of KwonP-2 was 31.5 unit/g. The ALDH activity of KwonP-2 was 11.21 times higher than that of the type-strain [FIG. 34].

The maximum density (OD660 nm) of KwonP-3 (KCTC14123BP) was 134.1. The maximum density of KwonP-3 was 4.12% higher than that of the type-strain. The growth of KwonP-3 ended earlier than that of the type-strain. The specific growth rate (OD660 nm/hr) of KwonP-3 was 6.08% higher than that of the type-strain. The ALDH activity of KwonP-3 was 29.5 unit/g. The ALDH activity of KwonP-3 was 10.5 times higher than that of the type-strain [FIG. 35].

The maximum density (OD660 nm) of PicoYP (KCTC14983BP) was 123.8. The maximum density of PicoYP was 3.88% higher than that of type-strain. The growth curve characteristics of PicoYP were similar to those of type-strain. The specific growth rate (OD660 nm/hr) of PicoYP was 6.22% higher than that of the type-strain. The ALDH activity of PicoYP was 44.2 unit/g. The ALDH activity of PicoYP was 15.73 times higher than that of the type-strain [FIG. 36].

The maximum density (OD660 nm) of PicoYP-01 (KCTC14984BP) was 126.9. The maximum density of PicoYP-01 was 1.47% higher than that of the type-strain. The growth curve characteristics of PicoYP-01 were similar to those of type-strain. The specific growth rate (OD660 nm/hr) of PicoYP-01 was 2.14% higher than that of the type-strain. The ALDH activity of PicoYP-01 was 47.1 unit/g. The ALDH activity of PicoYP-01 was 16.76 times higher than that of the type-strain [FIG. 37].

The maximum density (OD660 nm) of PicoYP-02 (KCTC14985BP) was 148.1. The maximum density of PicoYP-02 was 14.99% higher than that of the type-strain. The growth curve of PicoYP-02 was located at the top compared to the type-strain. The specific growth rate (OD660 nm/hr) of PicoYP-02 was 9.64% lower than that of the type-strain. The ALDH activity of PicoYP-02 was 52.68 unit/g. The ALDH activity of PicoYP-02 was 18.75 times higher than that of the type-strain [FIG. 38].

[Example 7] Preparation of Mutant Strain Lysates (KARC)

To preserve the enzymes (ALDH, ADH) contained in the mutant enzyme lysate, proteases were removed and inhibited. To preserve the enzymes (ALDH, ADH) contained in the mutant enzyme lysate cell debris was removed. The dried product or lysate of the mutant strain was mixed to prepare the KARC composition.

The mutant strain and the medium in which it was cultured contained various substances, such as yeast metabolites and proteolytic enzymes secreted by yeast. In order to extract and preserve ALDH, coenzyme, and glutathione present in yeast, it is necessary to sufficiently remove substances outside the yeast fungus, and for this purpose, a washing process was performed. Washing of the mutant strain was carried out by dispensing 40 ml of culture medium into 50 ml conical tubes, centrifuging at 13,000 rpm for 15 minutes, and removing the supernatant.

As a result of centrifugation, residual medium remained inside the pellet produced by the yeast bacteria clumping together. After adding 30 ml of purified water, the pellet was sufficiently loosened by vortex, and the previous process was repeated three times to sufficiently remove the remaining medium.

The ethanol resistance of yeast is known to be up to 13%, and yeast bacteria die when exposed to high concentrations of ethanol. The washed pellet was sufficiently dissolved using 10 ml of 20% ethanol solution to induce the death of yeast bacteria. The pellet dissolved in ethanol was stirred at 100 rpm for 30 minutes to proceed with the yeast death process. When the reaction time was completed, 30 ml purified water was added to lower the ethanol concentration to 5%. The previous washing process was repeated three times to sufficiently remove ethanol.

To preserve ALDH and ADH from the decomposition action of proteases present in yeast cells, 10 ml of 1×PBS was prepared by dissolving 2 tablets of protease inhibitor (Pierce protease inhibitor mini tablets, EDTA-free, Thermo Scientific). The above solution was added to the washed yeast pellet and sufficiently released.

To prepare a lysate of the mutant strain prepared in the present invention, 4 g of glass beads were added and stirred to break the yeast cell wall. To prevent denaturation of the enzyme due to the heat generated during the process of crushing the yeast, vortex for 30 seconds and ice incubation for 30 seconds were repeated six times.

After the yeast cell wall disruption was completed, 10 ml of 100 mM potassium phosphate buffer was added and mixed by vortex for 3-5 seconds. It was centrifuged at 13,000 rpm for 15 minutes to remove cell structures such as yeast cell walls and glass beads. The supernatant was filtered through a 0.2 μm filter (Minisart) Syringe Filter, Sartorius, Goettingen, Germany) to prepare the KARC composition.

To preserve the enzymes (ALDH, ADH) contained in the mutant enzyme lysate, intracellular proteases were removed and inhibited, and cell debris such as cell walls were removed. The KARC composition was prepared with a lysate selected from the 6 mutant strains (KwonP-1, KwonP-2, KwonP-3, PicoYP, PicoYP-01, PicoYP-02), or a mixture thereof in a free ratio [Table 6].

KARC 1 was manufactured from KwonP-1. The enzyme activity of ADH and ALDH of KARC 1 were 461.4 unit/g and 28.6 unit/g, respectively. In KARC 1, the content of coenzymes of NADtotal and NADPtotal were 176.2 nmole/g and 5.1 nmole/g, respectively. The GSH content of KARC 1 was 0.98 wt %.

KARC 2 was manufactured from KwonP-2. the enzyme activity of ADH and ALDH of KARC 2 were 482.1 unit/g and 29.8 unit/g, respectively. In KARC 2, the content of coenzymes of NADtotal and NADPtotal were 175.4 nmole/g and 5.2 nmole/g, respectively. The GSH content of KARC 2 was 0.96 wt %.

KARC 3 was manufactured from KwonP-3. the enzyme activity of ADH and ALDH of KARC 2 were 477.5 unit/g and 28.1 unit/g, respectively. In KARC 3, the content of coenzymes of NADtotal and NADPtotal were 177.2 nmole/g and 5.1 nmole/g, respectively. The GSH content of KARC 3 was 1.00 wt %.

KARC 4 was manufactured from PicoYP. the enzyme activity of ADH and ALDH of KARC 2 were 586.8 unit/g and 33.8 unit/g, respectively. In KARC 4, the content of coenzymes of NADtotal and NADPtotal were 184.3 nmole/g and 5.7 nmole/g, respectively. The GSH content of KARC 4 was 0.84 wt %.

KARC 5 was manufactured from PicoYP-01. the enzyme activity of ADH and ALDH of KARC 5 were 621.6 unit/g and 38.2 unit/g, respectively. In KARC 5, the content of coenzymes of NADtotal and NADPtotal were 186.9 nmole/g and 5.6 nmole/g, respectively. The GSH content of KARC 5 was 0.84 wt %.

KARC 6 was manufactured from PicoYP-02. the enzyme activity of ADH and ALDH of KARC 5 were 664.1 unit/g and 41.6 unit/g, respectively. In KARC 6, the content of coenzymes of NADtotal and NADPtotal were 195.0 nmole/g and 5.8 nmole/g, respectively. The GSH content of KARC 6 was 0.88 wt %.

KARC was manufactured by freely mixing dry powders and lysates prepared from six deposit strains. The average enzyme activities of ADH and ALDH in the composition of KARC were 547.6 unit/g and 33.1 unit/g, respectively. The average contents of coenzyme NADtotal and coenzyme NADPtotal in the composition of KARC were 180.4 nmole/g and 5.4 nmole/g, respectively. The average content of glutathione in the composition of KARC was 0.84 wt %.

The aldehyde decomposition ability of KARC was kept on during the lysate production process. KARC showed the ability to remove endogenous aldehydes such as HNE, MDA, and 3,4-dihydroxyphenyl acetaldehyde (DOPAL).

TABLE 6

| Name | Strain | ADH (Unit/g) | ALDH (Unit/g) | NADtotal (nmole/g) | NADPtotal (nmole/g) | GSH (wt %) |
|------|--------|--------------|---------------|--------------------|--------------------|-----------|
| KARC1 | KwonP-1 | 461.4 | 28.6 | 176.2 | 5.1 | 0.98 |
| KARC2 | KwonP-2 | 482.1 | 29.8 | 175.4 | 5.2 | 0.96 |
| KARC3 | KwonP-3 | 477.5 | 28.1 | 177.2 | 5.1 | 1.00 |
| KARC4 | PicoYP | 586.8 | 33.8 | 184.3 | 5.7 | 0.84 |
| KARC5 | PicoYP-01 | 621.6 | 38.2 | 186.9 | 5.6 | 0.83 |
| KARC6 | PicoYP-02 | 664.1 | 41.6 | 195.0 | 5.8 | 0.88 |
| KARC | average | 547.6 | 33.1 | 180.4 | 5.4 | 0.91 |

[Example 8] Analysis of Sequence of ALDH Contained in the Mutant Strain

It was investigated the differences between both ALD (yeast aldehyde dehydrogenase) of the mutant strains and parent strain. Whole genome sequencing was performed on the parent strain and mutant strains of KwonP-1, KwonP-2, KwonP-3, PicoYP, PicoYP-01, and PicoYP-02. The mutant strain cells were obtained by culturing pure strains on solid medium. The genome sequence of the mutant strain obtained were analyzed.

Among ALDs (yeast aldehyde dehydrogenases) in the novel mutant strains, ALD2 (SEQ ID NO:3) was found to be condensed with ALD3 (SEQ ID NO:4) on chromosome 13. A non-coding region of 689 nucleotides was located between the ALD2 and ALD3 coding genes.

The ALD2 and ALD3 existed continuously in the same genome. ALD2 and ALD3 encoded respective aldehyde dehydrogenases. ALD2 coding gene was almost similar to ALD3, consist of 1,521 nucleotides and 506 amino acids, but had an 8.2% difference in sequence. ALD2 and ALD3 they were identified as separate aldehyde dehydrogenases that differed from each other in 125 base sequences (8.2%).

In the six mutant strains (KwonP-1, KwonP-2, KwonP-3, PicoYP, PicoYP-01, PicoYP-02), there is no stop codon at the end of the ALD2 sequence, so proteins are synthesized continuously. As a result, a new, larger ALDH enzyme is created by linking a part of ALD2 and ALD3 [SEQ ID NO: 1].

ALD2 [SEQ ID NO. 3] of the type-strain (KCTC7296) consisted of 30 nucleotide sequences (SEQ ID NO. 6: 5'-GTTCACATAAATCTCTCTTTGGACAACTAA-3') coding 9 amino acids (SEQ ID NO. 8: N-VHINLSLDN-C) at the terminal, excluding the stop codon.

ALD2 of the six mutant strains consisted of specific 42 nucleotide sequences (SEQ ID NO. 2: 5'-AGATATAGAT-TATACACATTTAGAAAATTAGCCAAAAGAAAA-3') coding 14 amino acids (SEQ ID NO. 7: N-RYR-LYTFRKLAKRK-C) between 5'-terminal of ALD2 and ALD3.

There was no stop codon at the end of the sequence in ALD2 coding gene by deleted from the $1492^{nd}$ nucleotide of ALD2 to 647th nucleotide of non-coding region. Finally, the six deposited mutant strains had new mutated gene consist of total 3,054 bases coding novel ALD. [SEQ ID NO: 1].

[Example 9] In Vivo Acetaldehyde (Ach) and Malondialdehyde (MDA) Reduction Effect by Oral Administration of KARC For the acetaldehyde and MDA animal experiments, 5-week-old male Sprague Dawley (SD) rats (Rat) were used. The KARC composition was orally administered to rats at 10 units/kg or 20 units/kg, and alcohol (3 g/kg) was orally administered to the rats 30 minutes after KARC injection.

After the administration was completed, blood samples were collected from the tail vein at 0, 1, 3, 5, and 8 hours after KARC injection, and after centrifugation, plasma was stored at −80° C. [FIGS. 3, 4].

9-1: Acetaldehyde Reduction Effect by Oral Administration of KARC

The total acetaldehyde reduction effect by oral administration of KARC was assessed using an Acetaldehyde assay kit (LSBio, Seattle, WA, USA). 20 μl of each sample was dispensed into two wells of a 96 well plate. 80 μl of working reagent (75 μl assay buffer, 8 μl NAD/MTT, 1 μl Enzyme A, 1 μl Enzyme B) was dispensed into one well. In the remaining well, 80 μl of blank working reagent (75 μl assay buffer, 8 μl NAD/MTT, 1 μl Enzyme B) was dispensed. The plate after dispensing was lightly mixed and reacted at room temperature for 30 minutes. When the reaction was completed, the absorbance was measured at 565 nm (520-600 nm).

The concentration of acetaldehyde reached the maximum 1 hour after ethanol administration and showed a tendency to decrease in the KARC composition administration group. In the KARC administration group, acetaldehyde concentration significantly decreased compared to the control group (Vehicle) 1, 3, and 5 hours after ethanol administration. In the KARC high-dose administration group (F), the blood acetaldehyde concentration was 0.356, 0.224, and 0.091 mM, respectively, which decreased by 39.2%, 58.4%, and 72.1% compared to the control group [FIG. 3].

9-2: MDA Reduction Effect by Oral Administration of KARC

Total malondialdehyde content in blood was analyzed using the OxiTec™ TBARS assay kit according to the manufacturer's protocol (ZeptoMetric, Buffalo, NY, USA). 100 μl sample, 100 μl 8.1% SDS solution, and 4 ml color indicator (TBA, 10% NaOH solution, 20% acetic acid) were added to the conical tube, and then reacted in a constant temperature water bath at 95° C. for 60 minutes. After completion of the reaction, the sample was centrifuged at 4° C. and 1,600 rpm for 10 minutes and stabilized at room temperature for 30 minutes. 150 μl of supernatant was transferred to a 96 well plate, and absorbance was measured at 530-540 nm.

In the control group (Vehicle), the concentration of MDA in the blood reached the maximum 3 hours after ethanol administration, whereas in the group administered KARC, it reached the maximum value 1 hour after ethanol administration. The concentration of MDA in the blood decreased, showing a significant difference from the control group 3 and 5 hours after ethanol administration. The blood MDA concentration of the KARC high-dose administration group (F) was 0.232 and 0.137 μM, respectively, a decrease of 80.4% and 86.3% compared to the control group [FIG. 4].

[Example 10] Effect of Behavior and Motor Function Improvement Through KARC Oral Administration Parkinson's disease mouse model was established using MPTP and rotenone to observe the effects of KARC oral administration on behavioral and motor function improvement. The pharmacological effects of KARC on Parkinson's disease were validated by alterations in behavioral and motor abilities (rotarod test, pole test, postural instability test, pasta handling test), and substances in the brain (DOPAL, DOPAC, HVA, α-synuclein).

10-1: Preparation of PD Mouse Model Through MPTP Injection

Male C57/BL6 mice (8 weeks, 19-23 g) were divided into six groups for the experiment (n=5/group): a control group receiving PBS injection (CTL, Vehicle), a control group receiving PBS injection with KARC (20 unit/kg/day) oral administration, and experimental groups receiving MPTP injection with either KARC (0 or 10 or 20 unit/kg/day) or Rasagiline (0.1 mg/kg/day) oral administration. All animals had free access to food and water.

Mice were orally administered with KARC (0, 10, 20 units/kg/day) or Rasagiline (0.1 mg/kg/day) daily for 19 days. From the 10th day of KARC administration, intraperitoneal injections of MPTP (30 mg/kg/day) were administered for a period of 5 days [FIG. 8].

10-2: Preparation of PD Mouse Model Through Rotenone Injection 7-week-old male Wistar rats (7 weeks old, 250 g, n=8-10) were used. Rotenone solution (2.5 mg rotenone/ml, 20 μl DMSO/ml) was prepared using natural oil (middle chain triglycerides). Mice were intraperitoneal injection administered rotenone solution (2.5 mg/kg) daily for 60 days.

Two administration methods were employed to confirm the Parkinson's disease prevention and treatment effects of KARC. KARC (20 units/kg) was administered orally at the same time as rotenone administration to observe the effect of preventing Parkinson's disease. KARC (20 units/kg) or L-dopa were administered orally at the two weeks after rotenone administration to observe the effect of therapeutic Parkinson's disease. To quantify dopamine, brain tissues were isolated and stored at −80° C. in liquid nitrogen. [FIG. 9].

10-3: Preparation of Neuroinflammation Mouse Model Through Lipopolysaccharides (LPS) Injection Male C57/BL6 mice (8 weeks, 19-23 g) were divided into six groups for the experiment (n=5/group): a control group receiving PBS injection (CTL, Vehicle), a control group receiving PBS injection with KARC (20 unit/kg/day) oral administration, and experimental groups receiving LPS injection with either KARC (0 or 10 or 20 unit/kg/day) or Quercetin (10 mg/kg/day) oral administration. All animals had free access to food and water.

Mice were orally administered with ARC (0, 10, 20 units/kg/day) or Quercetin (10 mg/kg/day) daily for 3 days and subsequently injected with LPS (10 mg/kg) or PBS. The mice were sacrificed 3 hours after receiving injections of LPS or PBS [FIG. 10].

10-4: Changes in Behavior and Motor Functions

PD model mice treated with MPTP were subjected to a rotarod test and a pole test to assess balance and leg motor ability. Rotenone-treated PD model rats were subjected for balance, stepping test measurements and toe drag, and pasta handling test to assess leg motor ability.

10-4-1: Rotarod Test

The rotarod test was performed to observe the motor and balance abilities of the mouse's fore and hind limbs. Mice were subjected pre-training on the rotating rod of the Rotarod unit set (ROTA-ROD, SK—RO) on days 18 and 19 after KARC administration.

During the pre-training period, the rotation speed of 2 rpm was maintained on the rotating rod (100 mm in diameter) for 5 minutes. Once stabilized, the speed was gradually increased to 1 rpm per 6 seconds, and the time remaining on the rod and the time falling from the device were recorded. The pre-training was performed three times a day, and the main experiment was performed on the 20th day after KARC administration in the same manner as the pre-training.

MPTP-injected mice showed a 65.9% reduction in latency to fall on the rotating rod, from 218.4 seconds to 74.5 seconds, compared to normal mice [FIG. 18]. Mice treated with KARC showed a 52.0% and 61.0% concentration-dependent increase in time spent on the rotating rod to 155.1 and 190.8 seconds, respectively, compared to MPTP injected mice. The reference drug Rasagiline had a MPTP of 175.8 seconds, a 57.6% increase over the group receiving MPTP.

10-4-2: Pole Test

A pole test was performed to observe the motor skills and balance of the mouse's front and back legs. The mice were affixed to the upper part of a sturdy pole (diameter 8 mm, height 55 cm) that provided ample grip for descending, and the time it took for all four paws to touch the ground was recorded as the descent latency time (T-LA).

MPTP-injected mice showed a 46.5% increase in time to floor (T-LA) from 6.9 to 10.1 seconds compared to normal mice [FIG. 19]. KARC (10, 20 units/kg/day) treatment reduced T-LA by 29.8% and 36.7% to 7.1 and 6.4 seconds, respectively, compared to MPTP treatment. The reference drug Rasagiline (0.1 mg/kg/day) shortened T-LA by 35.7% compared to MPTP at 6.5 seconds.

10-4-3: Postural Instability Test

A postural instability test was conducted to assess the balance sensitivity of rats. The body and one front paw of the rat were gently held. The hindquarters were elevated, and the rat was gently moved forward from a height where the front paw barely touched the surface. The rat's center of gravity shifted forward, causing it to move its front paws to regain balance. The process was repeated twice, and the distance traveled by the foot to regain balance was measured to the left and right, respectively, and averaged.

10-4-4: Pasta Handling Test

The pasta handling test was performed to determine the cooperation and motor skills between the forepaws of rats. In this test, a piece of pasta was placed on the floor near the front of the cage. This was measured by recording the time it took the rat to eat a piece of pasta, the forelimb used, and the position of the forelimb as seen on the Pasta Handling Score sheet.

As Parkinson's disease progressed, "balance disorder" and "rigidity" were observed, and "balance disorder" was confirmed by the tapping, toe drag test and "rigidity" by the pasta handling test. In the assessment of postural instability and observation of toe drag, it was observed that a significant reduction in stride width was induced in a rat model of Parkinson's disease (PD) using rotenone. The Parkinson's disease treatment, L-dopa, improved balance impairment.

The present invention's KARC exhibited effects similar to L-dopa in improving balance impairment. It demonstrated significantly higher effectiveness in preventing balance impairment compared to L-dopa. "toe drag" was observed in 71.4% of the group administered rotenone, whereas it was observed in less than 14.3% of the groups administered L-dopa and KARC [FIG. 20, 21]. In the pasta handling test, rotenone significantly induced rigidity in the front paws, resulting in a 40.0% increase in pasta consumption time compared to the control group [FIG. 22]. The L-dopa group showed a substantial improvement in front paw rigidity, with a 35.7% reduction in pasta consumption time compared to the rotenone group (Vehicle). The administration of the present invention's KARC reduced pasta consumption time by 42.9%, significantly preventing Parkinson's disease.

The treatment group administered the present invention's KARC showed no significant improvement in rigidity, with a 14.3% enhancement. This data is significant as it demonstrates that the present invention's KARC can improve behavioral symptoms associated with Parkinson's disease, such as balance impairment and rigidity, and is more effective than the therapeutic agent L-dopa when used for preventive purposes.

10-5: Changes in Brain Neurotransmitters 10-5-1: Effect of KARC Oral Administration on the Reduction of DOPAL To measure the effect of reducing dopamine-derived DOPAL by oral administration of KARC, the DOPAL content in rat brain striatonigral muscle samples was measured by HPLC/MMS. After dissolving the sample in trichloroacetic acid (3.0 M/100 µl), isoproterenol (1 nmol/ml, 100 µl) was added and pretreated by centrifugation using a toyopak SP carton (Toso, Tokyo, Japan).

To dissolve the adsorbed amine compound, 0.6 M KCl-acetonitrile (1:1, 2 ml) was treated, and DPE reagent was added to the solution to induce fluorescence. The final solution produced as a result of the reaction was injected into HPLC to measure dopamine.

To measure the DOPAC and HVA content in the sample, the sample was dissolved in $HClO_4$ (300 µl), and the supernatant was obtained by homogenization and centrifugation (50,000 g, 4° C., 15 minutes). The supernatant was filtered and DOPAC and HVA contents were measured through HPLC/MMS. The content of DOPAL was calculated as ng/g tissue.

To investigate changes in dopamine metabolism in the brain of PD model animals using rotenone, DA, DOPAL, DOPAC, and HVA were measured using HPLC [FIG. 11].

As a result of the measurement, the levels of DA, DOPAL, DOPAC, and HVA in the brain of the control group were measured at 1542, 22, 620, and 970 ng/g tissue weight, respectively. In the group where PD was induced using rotenone, the levels of DA, DOPAC and HVA were decreased by 1021, 234, and 102 ng/g tissue weight, respectively compared to the control group. But the level of DOPAL was relatively increased 70 ng/g weight.

In the group administered the reference drug L-Dopa, DA and DOPAL levels in the brain increased 1816 and 96 ng/g tissue weight compared to the control group, respectively, but DOPAC and HVA levels decreased 281 and 126 ng/g tissue weight. Similar results to the rotenone administration group were observed.

On the other hand, in the group administered KARC to the Parkinson's induction model, DA, DOPAL, DOPAC, and HVA in brain tissue were 1290, 21, 510, and 790 ng/g tissue weight, respectively. DA, DOPAC, and HVA increased compared to the rotenone administered group, and DOPAL relatively decreased.

In particular, in KARC pre-administered group for preventive purposes, DA and DOPAL increased 1522 and 18 ng/g tissue weight compared to the control group, respectively, and DOPAC and HVA also increased 590 and 860 ng/g tissue weight, resulting in all levels of DA, DOPAL, DOPAC and HVA were almost consistent with the results of the control group.

It was used the ratio of dopamine turnover index ((DOPAC+HVA)/DA), which is used to indirectly check the amount of DOPAL that remains unmetabolized during DA metabolism because DA is metabolized through DOPAL and DOPAC and is ultimately metabolized into HVA [FIG. 12].

As a result of calculating the dopamine conversion index [(DOPAC+HVA)/DA], It was 103.1% in the control group, 100.8% in the KARC pre-administration group, and 95.3% in the KARC post-administration group, which means that dopamine metabolism in vivo was progressive well in three groups.

On the other hand, compared to the three groups, there was a 32.9% decrease in the rotenone group and a 22.4% decrease in the L-dopa group, which means that dopamine metabolic dysfunction was abnormally caused by Parkinson's disease.

This means that DOPAL, a metabolic intermediate, is accumulated in vivo. KARC administration inhibited the accumulation of DOPAL, a neurotoxin, and recovered dopamine metabolism to normal, accelerating to increase DOPAC and HVA, which are relatively less toxic than DOPAL. As a result, KARC has the effect of preventing and treating PD with restoring DA metabolic function.

10-5-2: Preparing Brain Tissue

Mice were anesthetized by injecting chloral hydrate (40 mg/kg, i.p), transcardially perfused with a saline solution containing 0.5% sodium nitrate and heparin (10 U/ml), and then fixed with 4% paraformaldehyde dissolved in 0.1 M phosphate buffer (PB, pH 7.2).

Whole-brain tissues were dissected from the skull, post-fixed overnight with 4% para-formaldehyde in 0.1 M PB at 4° C. Stored in 30% sucrose solution in 0.05 M PBS at 40° C. until they sank.

The brains were frozen-sectioned on a Cryostat (Micro-systems AG, Leica, Wetzlar, Germany) in 30 μm thick coronal sections. The brains stored in a cryoprotectant (25% ethylene glycol, 25% glycerol, 0.2 M PB, and water) at 4° C. until use.

Striatum (ST) brain sections and substantia nigra (SN) sections were designated as one series of 6 sections, resulting in a total of 36 brain sections, and changes in the brain were observed through immunostaining.

10-5-3: Immunohistochemical Staining

Brain sections (30 μm in thickness) containing SN and ST were incubated with rabbit anti-tyrosine hydroxylase (TH, 1:2000; Pel-Freez Biologicals, Rogers, AR, USA) for dopaminergic neurons.

Brain sections (30 μm thickness) containing SN or hippocampus were incubated with rabbit anti-glial fibrillary acidic protein (anti-GFAP, 1:5000; Neuromics, Edina, MN, USA) or rabbit anti-ionized calcium binding adaptor molecule 1 (anti-Iba-1, 1:1000; Wako, Osaka, Japan). Respectively, followed by staining with biotinylated anti-rabbit IgG and an avidin-biotin peroxidase complex (ABC) standard kit (Vector Laboratories, Burlingame, CA, USA).

Signals were detected by incubating sections with 0.5 mg/ml 3,3'-diaminobenzidine (Sigma, St. Louis, MO, USA) in 0.1 M PBS containing 0.003% H2O2.

To quantify GFAP- or Iba-1-positive cells, stained brain sections were imaged un-der a bright-field microscope (Olympus Optical, Tokyo, Japan). The results were quantified by counting the number of TH-immunopositive neurons in the SN in brain tissue sections (5 sections/series) at ×100 magnification. The TH-immunopositivity in ST was measured by the optical density of TH-positive fibers at ×40 magnification using ImageJ software (National Institutes of Health, Bethesda, MD, USA).

10-5-4: Stereological Cell Counting

The unbiased stereological estimation of the total number of TH-immunopositive neurons in the SN was made using the optical fractionator method performed on an Olympus CAST (computer-assisted stereological toolbox system) version 2.1.4. The actual counting was performed using a ×100 objective. The estimate of the total number of neurons was calculated according to the Optical Fractionator Equation.

10-5-5: Protective Effect of Dopaminergic Neurons

To investigate the effect of the KARC on dopaminergic neurons, mouse brains were immune-stained using an anti-TH antibody [FIG. 13]. Dopaminergic neurons were quantified by stereological counting of TH-positive neurons in the SNpc and absorbance of TH-positive fibers in the striatum.

In PD model mice treated with MPTP, there was a decrease in the death of TH-positive neurons in the SNpc (38.40±12.31%, p<0.001, n=5) [FIG. 14] and a decrease in TH-positive fibers in the striatum (36.82±12.25%, p<0.001) [FIG. 15] compared to the control group.

Mice treated with KARC (10 or 20 units/kg) showed a significant increase in TH-positive neurons in the SN (1 g/kg: 59.4±30.3%, p<0.001; 2 g/kg: 66.37±19.00%, p<0.001) and TH-positive fibers in the striatum (1 g/kg: 74.02±13.49%, p<0.001; 2 g/kg: 85.14±10.43%, p<0.001) compared to vehicle controls. Rasagiline also increased TH-positive neurons in the SNpc (74.87±16.19%, p<0.01) and TH-positive fibers in the striatum (105.3±10.74%, p<0.01), but showed weaker effects compared to KARC.

10-5-6: Inhibitory Effect on α-Synuclein Aggregation in Dopaminergic Neurons

The effect of KARC on the accumulation of intracellular α-synuclein in SNpc of a PD rat model treated with Rotenone was observed. Nigral sections were co-immuno-stained with antibodies against TH (red) and α-synuclein (green). The sections were analyzed using laser scanning confocal microscopy [FIG. 16].

Abnormal aggregation of α-synuclein in the substantia nigra of the brain leads to neuronal death due to increased endoplasmic reticulum stress and neuroinflammation. In normal rats, no accumulation of α-synuclein was observed in TH-positive neurons. In the rotenone-treated group, a decrease in TH-positive neurons and accumulation of α-synuclein was observed compared to the control group.

In the KARC-treated and L-dopa-treated groups, the loss of dopaminergic neurons and the accumulation of α-synuclein were significantly reduced compared to the rotenone-treated group. The accumulation of α-synuclein was reduced in the group treated with KARC for prophylactic purposes compared to the group treated with L-dopa [FIG. 17].

10-5-7: Inhibitory Effect on Neuroinflammatory Microglial and Astrocyte Activation The effect of KARC on the activation of neuronal cells, microglia and astrocytes, in the SN of an LPS-induced neuroinflammatory PD mouse model was observed. Nigral sections were analyzed by immunostaining with Iba-1 (microglia) [FIG. 23] and GFAP (astrocytes) [FIG. 25] antibodies.

In the SN tissues of LPS (10 mg/kg) injected mice, morphological changes were observed in which activated microglia or astrocytes had cytoplasmic enlargement and neurites were sharpened and elongated in SN tissues from mice treated with KARC (10 units/kg, 20 units/kg) or quercetin (10 mg/kg), activated microglia and astrocytes showed a resting morphology with smaller cell bodies and shorter neurites, inhibiting their activation [FIG. 23, 25].

In LPS-injected mice, the number of activated GFAP or Iba-1 positive cells increased more than 4-fold in the total number of microglia (344.3±51.13%, p<0.001) and astrocytes (325.0±55.28%, p<0.05), respectively. In SN treated with KARC, most of the Iba-1 positive microglia (1 g/kg:

138.6±16.23%, p<0.001, 2 g/kg: 107.1±8.571%, p<0.001) and GFAP positive astrocytes (2 g/kg: 127.5±7.5%, p<0.01) were reduced.

Quercetin similarly reduced GFAP-positive astrocytes (115.0±15.61%, p<0.001) and Iba-1-positive microglia (107.1±19.64%, p<0.001). The number of activated microglia and astrocytes (per section) confirmed that the KARC inhibited the activation of both cells [FIG. 24, 26].

Neuroinflammation is known to be a factor that leads to dopamine neuronal degeneration and neuronal cell death. Commonly found features in neurodegenerative diseases caused by neuroinflammation include microglial activation, astrogliosis, and lymphocyte infiltration. In a normal state, microglia protect the nervous system by clearing protein fragments, killing pathogens, and regulating innate and adaptive immune responses.

After the onset of various neurodegenerative diseases such as nerve damage, stroke, trauma, Alzheimer's disease, Parkinson's disease, and multiple sclerosis, microglia become activated. Release inflammatory cytokines and neurotoxic substances, including TNF-α (Tumor necrosis factor alpha), IL-1alpa (Interleukin-1alpha), IL-6 (Interleukin-6), and NO (nitric oxide).

It has been suggested that enhanced activation of NF-kappaB (Nuclear factor-kappaB) may contribute to maintaining the activated state of inflammatory microglia and progressive neurodegeneration in PD. Therapeutic intervention in the inflammatory response is proposed to be helpful in preventing disease progression or halting the pathological process of PD.

Iba-1 (ionized calcium-binding adapter molecule 1) is a protein that represents one type of allograft inflammatory factor-1 (AIF-1) and is specifically expressed in microglia in the central nervous system. Iba-1 is overexpressed in microglia in nerve injury, CNS ischemia, and various other brain disorders.

The decreased expression of Iba-1 indicates that KARC has a neuroprotective effect and improves CNS ischemia, and further implies the improvement of various brain disorders.

GFAP (glial fibrillary acidic protein) is a fibrous acidic protein present in brain nerve cells and is used as a marker for astrocytes, the stellate cells distributed in the central nervous system (CNS). GFAP is involved in various functions including the formation of nerve cell myelin and is important for regulating the mobility and maintaining the shape of astrocytes.

In mammals, it is known that the expression of GFAP is specifically increased in damaged astrocytes in the brain that have been subjected to various physical and chemical causes. Ultimately, the increase in damaged astrocytes leads to the induction of inflammation and death of brain nerve cells, accelerating the progression of neurodegenerative brain diseases.

The decrease in GFAP indicates the recovery of damaged astrocytes by KARC and implies the preventive and therapeutic effects on neurodegenerative brain diseases.

Treatment with KARC significantly inhibited the LPS-induced neuroinflammatory response, as analyzed by the degree of activation of microglia and astrocytes. These data suggest that KARC has therapeutic potential for neuroinflammation in vivo.

These results indicate that the KARC improved behavioral and motor function in the MPTP-treated PD mouse model, the Rotenone-treated PD rat model, and the LPS-treated PD mouse model. It also has a significant effect on modulating PD biomarkers in the brain. The data show that KARC, when taken prophylactically, is more effective in preventing and ameliorating PD than L-dopa, which is currently used as a treatment.

[Example 11] Effect of Reducing Oxidative Stress

Reactive oxygen species or oxidative stress increases when drinking alcohol due to excessive acetaldehyde (Ach) produced by alcohol dehydrogenase (ADH). Aldehyde dehydrogenase (ALDH) acts to convert it into acetic acid and excrete it out of the body. In the case of aldehyde dehydrogenase gene mutation or excessive aldehyde caused by excessive alcohol cause peroxidation of fat.

The resulting acetaldehyde and malondialdehyde worsen oxidative stress and interfere with mitochondrial energy metabolism. Endoplasmic reticulum stress is induced through the accumulation of denatured proteins in cells, leading to cell death.

The concentration of blood acetaldehyde was measured over time following alcohol consumption [FIG. 5]. The area under the curve (AUC) of blood acetaldehyde (Ach) was 13.02±1.18 mgh/dL for alcohol consumption alone. When administered at a dose of KARC 10 units/kg, the area under the curve (AUC) of blood acetaldehyde (Ach) significantly decreased by 26.13% compared to alcohol consumption alone, measuring 9.39±1.07 mgh/dL (P=0.005).

At a dose of KARC 20 units/kg administration, the AUC of blood acetaldehyde (Ach) decreased significantly by 55.71% compared to alcohol consumption alone, measuring 5.22±0.99 mg·h/dL (P<0.001). When comparing the KARC 10 units/kg administration group with the KARC 20 units/kg administration group, the blood acetaldehyde (Ach) in the KARC 20 units/kg group decreased significantly (P=0.034). KARC demonstrated dose-dependent reduction in the total amount of blood acetaldehyde (Ach) over time.

The reduction in blood acetaldehyde (Ach) concentration due to KARC administration has a positive impact on reducing oxidative stress and promoting health.

The concentration of blood malondialdehyde (MDA) was measured during the chemotherapy period [FIG. 6]. The concentration of blood MDA in the control group was 0.607±0.161 μM. The group undergoing treatment with KARC showed a significant 63.3% reduction in blood MDA concentration, measuring 0.223±0.033 UM compared to the control group (P<0.001).

In the control group, the blood MDA concentration ranged from 0.427 μM to 0.885 μM with a substantial variability. In the KARC administration group, the range was significantly reduced, with values ranging from 0.158 μM to 0.269 μM. This not only confirmed the effect of reducing blood MDA concentration but also stabilizing it, as demonstrated in [FIG. 7].

Various factors, such as drug intake, stress, and intense physical exercise, lead to an increase in intracellular reactive oxygen species. This triggers lipid peroxidation reactions and oxidative processes in endogenous amines such as dopamine, norepinephrine, serotonin, histamine, and more. Reactive aldehyde compounds, including 4-hydroxynonenal (HNE), malondialdehyde (MDA), acetaldehyde (Ach), and dopamine-induced aldehyde, accumulate within cells, exacerbating oxidative stress.

These aldehydes subsequently react with surrounding proteins and undergo secondary metabolic processes to form stable end products such as Malondialdehyde-acetaldehyde adduct (MAA) and Malondialdehyde lysine adducts (M-lys adducts), known as Advanced Lipid Peroxidation End Products. The accumulation of these products exerts toxic effects on various cells, further intensifying oxidative stress.

This cumulative oxidative stress disrupts mitochondrial energy metabolism within cells and leads to the buildup of aldehyde intermediates in aldehyde-based sugar metabolism, including methylglyoxal (MG) and glyceraldehyde-3-phosphate (GA3P). The chain reaction involving aldehydes results in the accumulation of stable final glycoxidation products known as advanced glycation end products (AGEs), which weaken intracellular antioxidant defense systems like glutathione (GSH). These processes elevate endoplasmic reticulum (ER) stress, leading to increased cellular apoptosis in nerve cells.

The increase in reactive oxygen species and oxidative stress is associated with elevated levels of reactive aldehydes like HNE and MDA, as well as modified proteins such as advanced glycation end products (AGEs) and advanced lipid peroxidation end products (ALEs). This cascade of events is known to involve mutual reinforcement and amplification, leading to heightened endoplasmic reticulum stress (ER stress).

KARC administration effectively regulated malondialdehyde, a marker for active oxygen and oxidative stress, demonstrating the potential for reducing oxidative stress and improving the constancy of endoplasmic reticulum (ER) stress. KARC significantly reduced malondialdehyde concentrations in the bloodstream, illustrating its capability to reduce active oxygen and oxidative stress.

By lowering the levels of acetaldehyde and malondialdehyde in human blood, KARC exhibited its potential to prevent and remedy ER stress through the reduction of active oxygen and oxidative stress. This suggests that by modulating intracellular active oxygen and oxidative stress, KARC inhibits neuronal cell apoptosis, consequently suppressing and preventing Parkinson's disease. This leads to improvements in behavioral and motor functions.

[Example 12] Acute Oral Administration Test 12-1. Preparation of Experimental Animals The experimental animals were female and male ICR mice (7 weeks old). The received ICR mice were acclimatized for 7 days. The general symptoms of the adopted mice were observed during the acclimatization period, and only healthy animals were used for short-term administration toxicity tests. Feed and water were consumed ad libitum. Based on the average body weight of about 20 g the day before oral administration, groups were separated into 10 groups, 5 for each group, and 5 for each group.

12-2. Administration of Test Substances

The test substance was prepared by dissolving it in physiological saline so that the dosage for experimental animals was 0, 750, 3,000, and 5,000 mg/kg, respectively, based on the content of the mutant yeast lysate KARC of the present invention.

The standards for administered dosage were in accordance with the Ministry of Food and Drug Safety's Korea national Toxicology Program (KNTP) toxicity test manual. The maximum application dose of 5,000 mg/kg guided by the KNTP manual was set as the maximum concentration for this experiment. The samples prepared for each group were orally administered once to each test animal. For the normal group (G1), physiological saline was administered.

13-3. Observation and Autopsy

For animals in all test groups, symptoms of mice were observed at least once a day from the date of acquisition to the date of necropsy. Symptoms were observed for 7 days after oral administration. After observing the rat's symptoms, an autopsy was performed. During the autopsy of the rat, changes in each organ were observed with the naked eye.

A single-dose toxicity test of the ALDH-containing KARC composition of the present invention was conducted using mice. As a result, no cases of mouse death were observed for 7 days at concentrations of the mutant yeast KARC up to 5,000 mg/kg. No unusual features, such as weight gain or changes in feed intake, were found in the mice. No unusual findings were found in the autopsy results conducted after the end of observation.

[Example 13] Effect of KARC on CamK-PARIS Parkinsons's Disease Transgenic Mice

Camk-PARIS PD transgenic mice were created to observe the effect of motor function and neuronal recovery by oral administration of KARC. The effectiveness of KARC was confirmed through motor abilities (pole test) and neuronal changes (TH, GFAP, Neun) in brain tissue.

13-1: Production of Camk-PARIS Parkinsons's Disease Transgenic Mice camk-PARIS PD Tg mice were generated by crossing CamKIIa-tTA mice with TetP-PARIS mice (CamKIIa-tTA; TetP-PARIS). To suppress PARIS expression, Camk-PARIS PD Tg mice were fed doxycycline-containing chow until 1.5-1.8 months, then switched to normal chow to induce PARIS expression.

All groups of mice were orally administered either water or KARC (20 units/kg/day) daily for 4 weeks, starting 1 week before the initiation of PARIS expression. All animals had free access to food and water. KARC was administered orally for 4 weeks before behavioral tests of Camk-PARIS PD Tg mice were evaluated. Mice were sacrificed and brain regions were isolated for histopathologic evaluation. Mice brains were immediately frozen and stored in −80° C. liquid nitrogen.

13-2: Changes in Motor Ability of Camk-PARIS Parkinsons's Disease Transgenic Mice A pole test was performed to assess forelimb and hindlimb motor skills and balance in Camk-PARIS PD Tg mice. The mouse was fixed at the top of a pole (8 mm diameter, 55 cm height) with enough grip on a rough surface to climb down. The time it took for all four paws to land on the floor was recorded as the locomotor activity time (T-LA).

The efficacy of the KARC in behavioral testing for movement disorders caused by Parkinson's disease was evaluated in Camk-PARIS PD Tg mice using the pole test. There was no difference in the T-LA time of the pole test in the group of WT normal mice given water and KARC (20 units/kg/day) orally. The T-LA of the Camk-PARIS PD Tg mice was significantly increased compared to the WT mice group with an average of 23 seconds. The T-LA time of mice orally treated with KARC (20 units/kg/day) was significantly shortened by 36.08% with an average of 8.3 seconds [FIG. 39].

13-3: Preparing Brain Tissue

Protein was isolated from frozen brain tissue at −80° C. Proteins were quantified by BCA assay and 30 ug protein was subjected to western blot using 12% SDS-PAGE. Protein expression levels were observed using PARIS (Parkin-interacting substrate), TH (Tyrosine hydroxylase), GFAP (Glial fibrillary acidic protein), and NeuN (Neuronal nuclei) antibodies. The control protein alpha-acting was used to compare the expression of each protein [FIG. 40].

A consistent neurochemical abnormality in PD is degeneration of dopaminergic neurons in substantia nigra, leading to a reduction of striatal dopamine (DA) levels. Because TH catalyzes the formation of L-DOPA (L-dihydroxyphenylalanine), the rate-limiting step in the biosynthesis of DA, it has been considered a striatal TH deficiency syndrome. The activity and protein expression of TH can be used to determine the progression and severity of Parkinson's disease.

GFAP is a cytoskeletal intermediate filament protein expressed primarily in astrocytes. In Parkinson's disease, GFAP is hyperphosphorylated and overexpressed, and this degeneration of astrocytes is considered to be part of the pathogenesis of Parkinson's disease. Increased GFAP concentration can be used as an astrocyte marker as a tool to diagnose Parkinson's disease. It was also selected and applied as a diagnostic tool in this experiment. The reduction of GFAP indicates that the damage of astrocytes is restored by the KARC, which means that it has the effect of preventing and improving neurodegenerative diseases.

NeuN (Neuronal nuclei) is a protein expressed in most mammalian neurons. NeuN has been used in Parkinson's disease models as a marker for actual dopamine neuron reduction or simply reduced TH expression. NeuN is also used to measure protein expression of living neurons. The increase in NeuN expression signifies that the administration of KARC resulted in the recovery of brain neural cell damage and improvement in various brain disorders.

Expression of GFAP was an increased a cellular marker associated with inflammatory responses in the Camk-PARIS PD Tg mice brain tissue. The expression of neuronal markers, NeuN and TH in dopaminergic neurons, was decreased. In the Camk-PARIS PD Tg mice brain tissue orally administered with KARC, expression of GFAP was a decreased and expression of NeuN and TH increased. It is suggested that the KARC has inflammatory and neuronal therapeutic effects in Camk-PARIS PD Tg mice.

[Example 14] Observation of In Vitro Reduction of Various Aldehydes by KARC

The present invention confirmed the effect of KARC in reducing exogenous and endogenous aldehydes.

As a result of reacting KARC (300 mg/ml) with various aldehydes (1 mM) at 37° C. for 3 hours, 3,4-Dihydroxyphenyl acetaldehyde (DOPAL) decreased by 24.4%, succinic semialdehyde (SSA) by 74.9%, glyoxal by 23.8%, cinnamaldehyde by 99.6%, and benzaldehyde by 97.1%. In the case of acetaldehyde, it decreased by 100.0% even after reacting at 30° C. for 1 hour. [FIG. 41-68]

14-1: Reaction of KARC and Various Aldehydes

Potassium chloride (KCl) was dissolved in a 50 mM of pH 7.5 HEPES buffer solution to be 200 mM. For experiments with acetaldehyde, glyoxal, DOPAL, cinnamaldehyde, and benzaldehyde, 935 µl of buffer solution, 15 µl of 100 mM EDTA aqueous solution, 30 µl of 100 mM NADP+aqueous solution, 10 µl of 100 mM aldehydes in Demineralized water (DW) or acetonitrile solution, and 10 µl of 300 mg/mL KARC were dispensed into microtubes. As a negative control, 935 µl of buffer solution, 15 µl of 100 mM EDTA aqueous solution, 30 µl of 100 mM NADP+aqueous solution, 10 µl of 100 mM aldehyde in DW or acetonitrile solution, and 10 µl of DW were dispensed into a microtube.

For experiments with SSA, 845 µl of buffer, 15 µl of 100 mM EDTA aqueous solution, 30 µl of 100 mM NADP+ aqueous solution, 10 µl of 10 mM SSA in acetonitrile solution, and 10 µl of 300 mg/mL KARC were dispensed into microtubes. As a negative control, 845 µl of buffer solution, 15 µl of 100 mM EDTA aqueous solution, 30 µl of 100 mM NADP+aqueous solution, 100 µl of 10 mM SSA in acetonitrile solution, and 10 µl of DW were dispensed into a microtube.

The reactants were shakes at 30° C. or 37° C. for 1 hour or 3 hours using thermo shaker.

14-2: Pre-Processing Before HPLC Analysis

For experiments using the representative aliphatic aldehydes: SSA, acetaldehyde, glyoxal, a 500 µl of each reaction was aliquoted into a microtube at the end of the reaction. 470 µl of methanol, 20 µl of 50 mM DNPH in acetonitrile solution, and 10 µl of 6N HCl were additionally dispensed into the microtube containing the reaction solution, and heated at 70° C. for 40 minutes. Alternatively, 480 µl of methanol, 10 µl of 100 mM DHBA in acetonitrile solution, and 10 µl of 6N HCl were added and heated at 70° C. for 40 min. After the heated solution was cooled, 10 µl was quantified and injected into HPLC for analysis.

For experiments with DOPAL, cinnamaldehyde, and benzaldehyde, representative of aromatic aldehydes, 10 µl of the solution reacted with KARC, without heating with DNPH or DHBA, was aliquoted and injected into the HPLC for analysis.

14-3: HPLC Analysis (HPLC) system (Waters Alliance 2690/2695 HPLC with Waters 2996 PDA detector) was used for analysis. The analytical column was 150 mm×4.6 mm i.d. packed with C18, 5 µm particle size (Shimadzu Scientific Instruments, Kyoto, Japan).

In gradient, it started at 80% of water (1 v/v % trifluoroacetic acid) and deployed in reverse phase to 20% after 15 minutes. Absorbance was analyzed at wavelengths of 254 nm, 310 nm, or 360 nm with an ultraviolet detector. The results were confirmed by the progress of the reaction in which aldehyde was consumed through the reduction of DNPH-aldehyde conjugates or DHBA-aldehyde conjugates in the experimental group compared to the negative control group.

[Example 15] Examples of Manufacturing Food and Pharmaceutical Compositions for Improving Behavior and Motor Function by Restoring Dopamine Metabolism In Vivo Food and pharmaceutical compositions containing KARC as an active ingredient for improving behavior and motor function were prepared. It is possible to prepare food or pharmaceutical compositions of various composition ratios containing KARC powder. As an example, the powder composition according to the present invention has the function of improving behavior and motor function through ingestion of 13 g of the composition twice a day. The weight ratio between the components and phases of the food or pharmaceutical composition containing the powder composition is shown in [Table 7].

TABLE 7

|  | Ingredient | Ratio (wt %) |
|---|---|---|
| A food composition for | KARC dry powder | 50 |
| improving behavioral and | Fructo-oligosaccharides | 9 |
| motor function | Stevia | 5 |
|  | Citric acid anhydrous | 10 |
|  | Iso-malto | 4.3 |
|  | Xylitol | 2.5 |
|  | Citrus juice Powder | 6.2 |
|  | Citrus Flavors Powder | 13 |

35

INDUSTRIAL APPLICABILITY

In the food and pharmaceutical composition, KARC dry powder, excipients, and natural sweeteners such as fructooligosaccharides, enzyme-treated stevia (Stevia), anhydrous citric acid, iso-maltodextrins (Iso-malto), and xylitol, citrus juice powder, and citrus flavor powder were added. Processing and testing of raw materials and final products of food or pharmaceutical compositions were conducted in accordance with the general test methods and the Health Functional Foods Act described in the Korean Food Code.

KARC-containing foods or pharmaceutical compositions can prevent or improve behavior and motor function deterioration.

Through the above examples, the KARC, the mutant yeast composition for suppressing and preventing Parkinson's disease, containing aldehyde dehydrogenase was described in detail: pharmacological effects, administration methods, therapeutically effective doses for disease models, short-term administration acute toxicity, and representative examples of food or pharmaceutical compositions. Although the efficacy of KARC has been described in detail through the above examples, these are only examples of the present invention.

A person skilled in the art can easily derive various modifications and other embodiments equivalent to the present invention from the above-described embodiments of the present invention.

Even foods or therapeutic agents containing a modified form of aldehyde dehydrogenase that embodies the technical gist of the present invention described in the patent claims fall within the scope of legal protection of the present invention.

SEQUENCE LISTING

```
Sequence total quantity: 8
SEQ ID NO: 1              moltype = DNA  length = 3054
FEATURE                   Location/Qualifiers
source                    1..3054
                          mol_type = genomic DNA
                          organism = Saccharomyces cerevisiae
SEQUENCE: 1
atgcctacct tgtatactga tatcgaaatc ccacaattga aaatctcttt aaagcaaccg  60
ctagggttgt ttatcaacaa tgagttttgt ccatcatcag atggaaagac catcgaaact  120
gtgaacccag ctactggcga accgataaca tccttccaag cagctaacga aaaggatgta  180
gacaaagctg tgaaagctgc cagggctgct tttgataacg tttggtcgaa gacatcttct  240
gagcaacgtg gtatttatct ttcaaactta ttaaaactta ttgaggagga gcaagacaca  300
cttgccgcat tagagacttt agacgctgga aagccttacc attcaaatgc caaaggtgat  360
ttggcacaaa ttttacagct taccagatat tttgctgggt ccgctgataa gtttgacaaa  420
ggtgcaacca taccattgac ttttaacaag tttgcatata ctctaaaagt tccttttggc  480
gttgttgctc aaatcgttcc atggaattat cctctagcta tggcttgttg gaaattgcaa  540
ggtgccttag cagccggtaa cacggttatc atcaaacctg ctgagaatac ctctctatct  600
ctactttatt ttgctacttt aattaaaaaa gcaggttttc cacctggtgt tgtcaatatc  660
gttcctggtt atggatcact tgtaggccaa gccctagcat ctcacatgga tatcgacaaa  720
atatctttta cgggaagcac caaggtcggt ggatttgtgt tggaagcttc cggccaatcg  780
aaccttaaag acgttacact agaatgcggt ggtaagtctc ctgctctcgt atttgaagat  840
gcagaccttg ataaggctat cgattggata gcagctggca ttttctacaa ttcaggacag  900
aattgtaccg caaactcaag agtttatgtt caaagttcga tctacgacaa gtttgttgaa  960
aagtttaaag aaactgcaaa gaaggagtgg gatgttgcag gaaaatttga tccgtttgat  1020
gagaaatgca tcgttggtcc agttatatca agtacacagt atgaccgcat caaaagttac  1080
atagaacgtg gtaaaaggga ggaaaagttg gacatgttcc agacctctga atttcctatt  1140
ggtggagcta aaggctactt cattccccca accatcttca ctgatgtccc gcaaacatcg  1200
aaactgttac aggatgagat atttggcccg gttgtggttg ttagcaagtt cacaaattat  1260
gatgacgctc tgaagctggc taatgatact tgctacgggc tcgcctctgc ggtcttcaca  1320
aaagatgtca agaaagcgca catgtttgct cgcgatatta aagcaggaac tgtttggatc  1380
aactcatcta acgatgaaga tgttaccgtt ccttttggcg ggtttaaaat gagtggtatt  1440
ggtagagaac tggggcaaag tggtgttgat acctatcttc aaacaaaagc aagatataga  1500
ttatacacat ttagaaaatt agccaaaaga aaaatgccta ccttgtatac tgatatcgaa  1560
atcccacaat tgaaaatctc tttaaagcaa ccgctagggt tgtttatcaa caatgagttt  1620
tgtccatcat cagatggaaa gaccatcgaa actgtgaacc cagctactgg cgaaccgata  1680
acatccttcc aagcagctaa cgaaaaggat gtagacaaag ctgtgaaagc tgccagggct  1740
gcttttgata acgtttggtc gaagacatct tctgagcaac gtggtattta tctttcaaac  1800
ttattaaaac ttattgagga ggagcaagac acacttgccg cattagagac tttagacgct  1860
ggaaagcctt ccattccaa tgctaaacaa gacttagccc agattataga acttacaaga  1920
tactatgcgg gggcggtcga caagttcaat atgggtgaaa ccattccatt gactttaac  1980
aagtttgcat atactctaaa agttcctttt ggcgttgttg ctcaaatcgt tccatggaat  2040
tatcctctag ctatggcttg tagaaaaatg caaggtgcct tagcggccgg taacacggtt  2100
atcatcaaac ctgctgaaaa tacctctcta tctctacttt attttgctac tttaattaaa  2160
aaagcaggtt ttccacctgg tgttgtcaat gtcattcctg gttatggttc cgttgtgggg  2220
aaagctttag gaacccacat ggatatcgac aaaatatctt ttacgggaag tactaaggtt  2280
ggcggctcag tattggaagc ttccggccaa tcgaacctta aggatatcac actagaatgc  2340
ggtggtaagt ctcctgctct tgtatttgaa gatgcagacc ttgataaggc tatagaatgg  2400
gtagcaaatg gtattttttt taattcggga cagatctgca ctgcaaactc aagagtttat  2460
gttcaaagtt cgatctacga caagtttgtt gaaaagttta agaaactgc aaagaaggag  2520
tgggatgttg caggaaaatt tgatccgttt gatgagaaat gcatcgttgg tccagttata  2580
tcaagtacac agtatgaccg catcaaaagt tacatagaac gtggtaaaag ggaggaaaag  2640
ttggacatgt tccagacctc tgaatttcct attggtggag ctaaaggcta cttcattccc  2700
ccaaccatct cactgatgt accagaaaca tctaagttgc tgcgtgatga aatatttggc  2760
ccggttgtgg ttgttagcaa gttcacaaat tatgatgacg ctctgaagct ggctaatgat  2820
acttgctacg ggctcgcctc tgcggtcttc accaaagatg tcaagaaagc gcacatgttt  2880
gctcgcgata ttaaagcagg aactgtttgg atcaatcaaa ccaatcaaga agaagctaaa  2940
```

```
gttccttttg gcggatttaa gatgagtggt attggtagag aatcaggcga caccggcgtt   3000
gataactatt tacaaataaa atcagtccat gtggatcttt cattggataa ataa           3054

SEQ ID NO: 2                moltype = DNA   length = 42
FEATURE                     Location/Qualifiers
source                      1..42
                            mol_type = genomic DNA
                            organism = Saccharomyces cerevisiae
SEQUENCE: 2
agatatagat tatacacatt tagaaaatta gccaaaagaa aa                        42

SEQ ID NO: 3                moltype = DNA   length = 1521
FEATURE                     Location/Qualifiers
source                      1..1521
                            mol_type = genomic DNA
                            organism = Saccharomyces cerevisiae
SEQUENCE: 3
atgcctacct tgtatactga tatcgaaatc ccacaattga aaatctcttt aaagcaaccg     60
ctagggttgt ttatcaacaa tgagttttgt ccatcatcag atggaaagac catcgaaact    120
gtgaacccag ctactggcga accgataaca tccttccaag cagctaacga aaaggatgta    180
gacaaagctg tgaaagctgc cagggctgct tttgataacg tttggtcgaa gacatcttct    240
gagcaacgtg gtatttatct ttcaaactta ttaaaactta ttgaggagga gcaagacaca    300
cttgccgcat tagagacttt agacgctgga aagccttacc attcaaatgc caaaggtgat    360
ttggcacaaa ttttacagct taccagatat tttgctgggt ccgctgataa gtttgacaaa    420
ggtgcaacca taccattgac ttttaacaag tttgcatata ctctaaaagt tccttttggc    480
gttgttgctc aaatcgttcc atggaattat cctctagcta tggcttgttg gaaattgcaa    540
ggtgccttag cagccggtaa cacggttatc atcaaacctg ctgagaatac ctctctatct    600
ctactttatt ttgctacttt aattaaaaaa gcaggttttc cacctggtgt tgtcaatatc    660
gttcctggtt atggatcact tgtaggccaa gcccctagcat ctcacatgga tatcgacaaa    720
atatctttta cgggaagcac caaggtcggt ggatttgtgt tggaagcttc cggccaatcg    780
aaccttaaag acgttacact agaatgcggt ggtaagtctc ctgctctcgt atttgaagat    840
gcagaccttg ataaggctat cgattggata gcagctggca tttttctacaa ttcaggacag    900
aattgtaccg caaactcaag agtttatgtt caaagttcga tctacgacaa gtttgttgaa    960
aagtttaaag aaactgcaaa gaaggagtgg gatgttgcag gaaaatttga tccgtttgat   1020
gagaaatgca tcgttggtcc agttatatca agtacacagt atgaccgcat caaaagttac   1080
atagaacgtg gtaaaaggga ggaaaagttg gacatgttcc agacctctga atttcctatt   1140
ggtggagcta aaggctactt cattccccca accatcttca ctgatgtccc gcaaacatcg   1200
aaactgttac aggatgagat atttggcccg gttgtggttg ttagcaagtt cacaaattat   1260
gatgacgctc tgaagctggc taatgatact tgctacgggc tcgcctctgc ggtcttcaca   1320
aaagatgtca agaaagcgca catgtttgct cgcgatatta aagcaggaac tgtttggatc   1380
aactcatcta acgatgaaga tgttaccgtt ccttttggcg ggtttaaaat gagtggtatt   1440
ggtagagaac tggggcaaag tggtgttgat acctatcttc aaacaaaagc agttcacata   1500
aatctctctt tggacaacta a                                             1521

SEQ ID NO: 4                moltype = DNA   length = 1521
FEATURE                     Location/Qualifiers
source                      1..1521
                            mol_type = genomic DNA
                            organism = Saccharomyces cerevisiae
SEQUENCE: 4
atgcctacct tgtatactga tatcgaaatc ccacaattga aaatctcttt aaagcaaccg     60
ctagggttgt ttatcaacaa tgagttttgt ccatcatcag atggaaagac catcgaaact    120
gtgaacccag ctactggcga accgataaca tccttccaag cagctaacga aaaggatgta    180
gacaaagctg tgaaagctgc cagggctgct tttgataacg tttggtcgaa gacatcttct    240
gagcaacgtg gtatttatct ttcaaactta ttaaaactta ttgaggagga gcaagacaca    300
cttgccgcat tagagacttt agacgctggt aagcctttcc attccaatgc taaacaagac    360
ttagcccaga ttatagaact tacaagatac tatgcggggg cggtcgacaa gttcaatatg    420
ggtgaaacca ttccattgac ttttaacaag tttgcatata ctctaaaagt tccttttggc    480
gttgttgctc aaatcgttcc atggaattat cctctagcta tggcttgttag aaaaatgcaa    540
ggtgccttag cggccggtaa cacggttatc atcaaacctg ctgaaaatac ctctctatct    600
ctactttatt ttgctacttt aattaaaaaa gcaggttttc cacctggtgt tgtcaatgtc    660
attcctggtt atggttccgt tgtgggaaaa gctttaggaa cccacatgga tatcgacaaa    720
atatctttta cgggaagtac taaggttggc ggctcagtat ggaagcttc cggccaatcg    780
aaccttaagg atatcacact agaatgcggt ggtaagtctc ctgctcttgt atttgaagat    840
gcagaccttg ataaggctat agaatgggta gcaaatggta ttttttttaa ttcgggacag    900
atctgcactg caaactcaag agtttatgtt caaagttcga tctacgacaa gtttgttgaa    960
aagtttaaag aaactgcaaa gaaggagtgg gatgttgcag gaaaatttga tccgtttgat   1020
gagaaatgca tcgttggtcc agttatatca agtacacagt atgaccgcat caaaagttac   1080
atagaacgtg gtaaaaagga ggaaaagttg gacatgttcc agacctctga atttcctatt   1140
ggtggagcta aaggctactt cattccccca accatcttca ctgatgtacc agaaacatct   1200
aagttgctgc gtgatgaaat atttggcccg gttgtggttg ttagcaagtt cacaaattat   1260
gatgacgctc tgaagctggc taatgatact tgctacgggc tcgcctctgc ggtcttcacc   1320
aaagatgtca agaaagcgca catgtttgct cgcgatatta aagcaggaac tgtttggatc   1380
aatcaaacca tcaagaaga agctaaagtt ccttttggcg gatttaagat gagtggtatt   1440
ggtagagaat caggcgacac cggcgttgat aactatttac aaataaaatc agtccatgtg   1500
gatctttcat tggataaata a                                             1521

SEQ ID NO: 5                moltype = DNA   length = 829
FEATURE                     Location/Qualifiers
```

-continued

```
source                    1..829
                          mol_type = genomic DNA
                          organism = Saccharomyces cerevisiae
SEQUENCE: 5
ggatctttcc gtagggtgaa cctggcggag agggatcatt aaagaaattt aataattttg   60
aaaatggatt tttttgtttt ggcaagagca tgagagcttt tactgggcaa gaagacaaga  120
gatggagagt ccagccgggc ctgcgcttaa gtgcgcggtc ttgctaggct tgtaagtttc  180
tttcttgcta ttccaaacgg tgagagattt ctgtgctttt gttataggac aattaaaacc  240
gtttcaatac aacacactgt ggagttttca tatctttgca actttttctt tgggcattcg  300
agcaatcggg gcccagaggt aacaaacaca aacaatttta tctattcatt aaatttttgt  360
caaaaacaag aattttcgta actggaaatt ttaaaatatt aaaaactttc aacaacggat  420
ctcttggttc tcgcatcgat gaagaacgca gcgaaatgcg atacgtaatg tgaattgcag  480
aattccgtga atcatcgaat ctttgaacgc acattgcgcc ccttggtatt ccaggggca   540
tgcctgtttg agcgtcattt ccttctcaaa cattctgttt ggtagtgagt gatactcttt  600
ggagttaact tgaaattgct ggccttttca ttggatgttt tttttccaaa gagaggtttc  660
tctgcgtgct tgaggtataa tgcaagtacg gtcgttttag gttttaccaa ctgcggctaa  720
tctttttta tactgagcgt attggaacgt tatcgataag aagagagcgt ctaggcgaac   780
aatgttctta aagtttgacc tcaaatccag gtaggagtcc ccaacgccc               829

SEQ ID NO: 6              moltype = DNA   length = 30
FEATURE                   Location/Qualifiers
source                    1..30
                          mol_type = genomic DNA
                          organism = Saccharomyces cerevisiae
SEQUENCE: 6
gttcacataa atctctcttt ggacaactaa                                    30

SEQ ID NO: 7              moltype = AA   length = 14
FEATURE                   Location/Qualifiers
source                    1..14
                          mol_type = protein
                          organism = Saccharomyces cerevisiae
SEQUENCE: 7
RYRLYTFRKL AKRK                                                      14

SEQ ID NO: 8              moltype = AA   length = 9
FEATURE                   Location/Qualifiers
source                    1..9
                          mol_type = protein
                          organism = Saccharomyces cerevisiae
SEQUENCE: 8
VHINLSLDN                                                            9
```

The invention claimed is:

1. A method for the treatment of Parkinson's disease in a subject in need thereof, comprising administering to the subject a food composition containing an aldehyde dehydrogenase, wherein the aldehyde dehydrogenase is encoded by the gene comprising the nucleic acid sequence set forth in SEQ ID NO: 1.

2. The method for the treatment of Parkinson's disease according to claim 1, wherein the aldehyde dehydrogenase dehydrogenates an endogenous aldehyde.

3. The method for the treatment of Parkinson's disease according to claim 2, wherein the endogenous aldehyde is produced by the oxidation of alcohol.

4. The method for the treatment of Parkinson's disease according to claim 2, wherein the endogenous aldehyde is selected from the group consisting of formaldehyde, acetaldehyde, 4-hydroxy-2-nonenal, non-2-enal, 4-hydroxy-hexanal, 4-oxo-nonena, malondialdehyde (MDA), propionaldehyde, hexanal, palmitic aldehyde, succinic aldehyde, and acrylic aldehyde.

5. The method for the treatment of Parkinson's disease according to claim 1, wherein the aldehyde dehydrogenase is contained in lysate of one or more microorganisms selected from the group consisting of Saccharomyces cerevisiae KCTC13925BP, Saccharomyces cerevisiae KCTC14122BP, Saccharomyces cerevisiae KCTC14123BP, Saccharomyces cerevisiae KCTC14983BP, Saccharomyces cerevisiae KCTC14984BP, and Saccharomyces cerevisiae KCTC14985BP.

* * * * *